(12) United States Patent
Markowitz et al.

(10) Patent No.: US 9,801,863 B2
(45) Date of Patent: Oct. 31, 2017

(54) INHIBITORS OF SHORT-CHAIN DEHYDROGENASE ACTIVITY FOR MODULATING HEMATOPOIETIC STEM CELLS AND HEMATOPOIESIS

(71) Applicants: CASE WESTERN RESERVE UNIVERSITY, Cleveland, OH (US); Board of Regents of the University of Texas System, Austin, TX (US)

(72) Inventors: Sanford Markowitz, Cleveland, OH (US); Amar Desai, Cleveland, OH (US); Stanton Gerson, Cleveland, OH (US); Joseph Ready, Austin, TX (US)

(73) Assignees: Case Western Reserve University, Cleveland, OH (US); Board of Regents of the Univeristy of Texas System, Austin, TX (US)

( * ) Notice: Subject to any disclaimer, the term of this patent is extended or adjusted under 35 U.S.C. 154(b) by 0 days.

(21) Appl. No.: 15/347,587

(22) Filed: Nov. 9, 2016

(65) Prior Publication Data

US 2017/0216265 A1 Aug. 3, 2017

Related U.S. Application Data

(63) Continuation-in-part of application No. 14/395,021, filed as application No. PCT/US2013/036790 on Apr. 16, 2013, and a continuation-in-part of application No. 15/029,943, filed as application No. PCT/US2014/060761 on Oct. 15, 2014, application No. 15/347,587, which is a continuation-in-part of application No. PCT/US2016/027549, filed on Apr. 14, 2016, application No. 15/347,587, which is a continuation-in-part of application No. PCT/US2016/021374, filed on Mar. 8, 2016.

(60) Provisional application No. 61/891,260, filed on Oct. 15, 2013, provisional application No. 61/954,202, filed on Mar. 17, 2014, provisional application No. 62/019,597, filed on Jul. 1, 2014, provisional application No. 62/043,694, filed on Aug. 29, 2014, provisional application No. 62/147,305, filed on Apr. 14, 2015, provisional application No. 62/252,973, filed on Nov. 9, 2015, provisional application No. 61/624,670, filed on Apr. 16, 2012, provisional application No. 62/129,885, filed on Mar. 8, 2015.

(51) Int. Cl.
*A61K 31/4365* (2006.01)
*A61K 38/19* (2006.01)
*A61K 31/495* (2006.01)

(52) U.S. Cl.
CPC ........ *A61K 31/4365* (2013.01); *A61K 31/495* (2013.01); *A61K 38/193* (2013.01)

(58) Field of Classification Search
CPC ................................................. A61K 31/4365

USPC ........................................................ 514/233.8
See application file for complete search history.

(56) References Cited

U.S. PATENT DOCUMENTS

| | | | |
|---|---|---|---|
| 4,966,974 | A | 10/1990 | Klausener et al. |
| 7,091,216 | B2 | 8/2006 | Toupence et al. |
| 7,131,958 | B2 | 11/2006 | Deverre |
| 7,147,626 | B2 | 12/2006 | Goodman et al. |
| 7,320,967 | B2 | 1/2008 | Michelet et al. |
| 7,396,525 | B2 | 7/2008 | Rozot et al. |
| 8,202,882 | B2 | 6/2012 | Hoelzemann et al. |
| 2004/0087593 | A1 | 5/2004 | Clark et al. |
| 2006/0034786 | A1 | 2/2006 | Michelet et al. |
| 2007/0071699 | A1 | 3/2007 | Boulle et al. |
| 2007/0078175 | A1 | 4/2007 | Boulle et al. |
| 2008/0206320 | A1 | 8/2008 | Michelet et al. |
| 2008/0249117 | A1 | 10/2008 | Michelet et al. |
| 2010/0022521 | A1 | 1/2010 | Nogradi et al. |
| 2011/0014250 | A1 | 1/2011 | Michelet et al. |
| 2011/0142816 | A1 | 6/2011 | Landry et al. |
| 2011/0269954 | A1 | 11/2011 | Cho et al. |

FOREIGN PATENT DOCUMENTS

| | | |
|---|---|---|
| FR | 2838641 A1 | 4/2002 |
| KR | 2010137090 A | 12/2010 |
| KR | 20101374090 A | 12/2010 |
| KR | 2013103945 A | 9/2013 |
| WO | 2007/038519 A1 | 4/2007 |
| WO | 2011/042860 A2 | 4/2011 |
| WO | 2013082243 A1 | 6/2013 |
| WO | 2013/158649 A1 | 10/2013 |

OTHER PUBLICATIONS

Supplementary European Search Report for Application No. 14859042.5-1462 / 3057973 dated Mar. 6, 2017.
A. Archelas et al: "Absolute Configuration of [alpha]-Methylstyrene Oxide: The Correct Absolute Configuration/Optical Rotation Correlation", The Journal of Organic Chemistry, vol. 64, No. 16, Aug. 1, 1999 (Aug. 1, 1999), pp. 6112-6114.
Frank H. Niesen et al: "High-Affinity Inhibitors of Human NAD+-Dependent 15-Hydroxyprostaglandin Dehydrogenase: Mechanisms of Inhibition and Structure-Activity Relationships", PLOS ONE, vol. 5, No. 11, Nov. 2, 2010 (Nov. 2, 2010), p. e13719.
Japanese Office action for Application No. 2015-507115, dated Jan. 31, 2017.

(Continued)

*Primary Examiner* — Taofiq A Solola

(74) *Attorney, Agent, or Firm* — Tarolli, Sundheim, Covell & Tummino LLP

(57) ABSTRACT

A method of modulating hematopoietic stem cells and hematopoiesis includes administering to a subject in need thereof a 15-PGDH inhibitor.

21 Claims, 38 Drawing Sheets

(56) References Cited

OTHER PUBLICATIONS

Baker, Michael E., Licorice and enzymes other than 1 I β-hydroxysteroid dehydrogenase: An evolutionary perspective, Department of Medicine, University of California, Steroids, Feb. 1994. vol. 59, p. 136-141.

Tatsuwaki, Hiroshi, et al., Reduction of 15-hydroxyprostaglandin dehydrogenase expression is an independent dehydrogenase expression is an independent predictor of poor survival associated with enhanced cell proliferation in gastric adenocarcinoma, Cancer Science, Feb. 2010, vol. 100, No. 2, p. 550-558.

Wu, Ying, et al., "Synthesis and Biological Evaluation of Novel Thiazolidinedione Analogues as 15-Hydroxyprostaglandin Dehydrogenase Inhibitors", J Med Chem, Apr. 5, 2011, 54, 5260-5264.

International Search Report for Application No. PCT/US2013/036790, dated Jul. 29, 2011.

Obeid, J., et al., "Tyr-179 and Lys-183 are essential for enzymatic activity of 11 beta-hydroxysteroid dehydroxysteroid dehydrogenase", Biochem Biophys Res Commun. Oct. 15, 1992;188(1):222-7.

Ensor, CM, et al., "Site-directed mutagenesis of the conversed tyrosine 151 of human placental NAD(+)-dependent 15-hydroxyprostaglandin dehydrogenase yields a catalytically inactive enzyme", Biochem Biophys Res Commun. Apr. 30, 1991;176(2):840-5.

Tanaka, N., et al., "Crystal Structures of the binary and ternary complexes of 7 alpha-hydroxysteroid dehydrogenase from *Escherichia coli.*", Biochemistry Jun. 18, 1996;35(24):7715-30.

Duveau, DY, et al., "Structure-activity relationship studies and biological characterization of human NAO(+)-dependent 15 hydroxyprostaglandin dehydrogenase", Bioorg Med Chem Lett. Jan. 15, 2014;24(2):630-5.

Piao, Yu Lan, et al., Wound healing effects of new 15-hydroxyprostaglandin dehydrogenase inhibitors, Prostaglandins, Leukotrienes and Essential Fatty Acids 91 (2014)325-332.

Bray, James E., et al. "The human short-chain dehydrogenase/reductase (SOR) superfamily: A bioinformatics Summary", Chemico-Biological Interactions 178(2009) 99-109.

Markowitz, Sanford, et al., "Molecular Basis of Colorectal Cancer", N. Engl J Med 2009;361 :2449-60.

Yan, Min, et al., "15-Hydroxyprostaglandin dehydrogenase, a COX-2 oncogene antagonist, is a TGF-β-induced suppressor of human gastrointestinal cancers", PNAS, Dec. 14, 2004, vol. 101, No. 50, 17468-17473.

Ensor, Charles Mark, et al., "Bacterial expression and site-directed mutagenesis of two critical residues ( tyrosine-151 and lysine-155) of human placental NAO +-dependent 15-hydroxyprostaglandin dehydrogenase", Biochimica et Biophysica Acta 1208 (1994) 151-156.

Yan, Min, et al, "15-Hydroxyprostaglandin dehydrogenase inactivation as a mechanism of resistance to celecoxib chemoprevention of colon tumors", PNAS, Jun. 9, 2009, vol. 106, No. 23, 9409-9413.

Tai, Hsin-Hsiung, et al., "Prostaglandin catabolizing enzymes", Prostaglandins & other Lipid Mediators 68-69 (2002) 483-493.

Choi, Dubok, et al., "Control of the intracellular levels of prostaglandin E2 through inhibition of the 15-hydroxyprostaglandin dehydrogenase for wound healing", Choi, D.; et al. Bioorg. Med. Chem. (2013), http://dx.doi.org/10.1016/j.bmc.2013.05.049.

Myung, Seung-Jae, et al., "15-Hydroxyprostaglandin dehydrogenase is an in vivo suppressor of colon tumorigenesis" PNAS, Aug. 8, 2006, vol. 103, No. 32, 12098-12102.

Otani, Taisuke, et al., "Levels of NAD+-dependent 15-hydroxyprostaglandin dehydrogenase are reduced in inflammatory bowel disease: evidence for involvement of TNF-a", Am J Physiol Gastrointest Liver Physiol 290: G361-G368, 2006.

Cho, Hoon, et al., "Role of glutamine 148 of human 15-hydroxyprostaglandin dehydrogenase in catalytic oxidation of prostaglandin E2", Bioorganic & Medicinal Chemistry 14 (2006) 6486-6491.

Clifford, P.C., et al., "Treatment of Vasospastic disease with prostaglandin E1", British Medical Journal vol. 281, Oct. 18, 1980, pp. 1031-1034.

Jadhav, Ajit, et al., "Potent and Selective Inhibitors of NAD+-dependent 15-hydroxyprostaglandin dehydrogenase (HPGD)", Probe Report 2011.

Markowitz, Sanford, et al., "Aspirin and Colon Cancer—Targeting Prevention", N Engl J med 256;21, May 27, 2007.

North, Trista E., "PGE2-regulated wnt signaling and N-acetylcysteine are synergistically hepatoprotective in zebrafish acetaminophen injury", PNAS, Oct. 5, 2010, vol. 107, No. 40, pp. 17315-17320.

Cho, et al., "Inhibition of NAD+-dependent 15-hydroxyprostaglandin dehydrogenase (15-PGDH) by cyclooxygenase inhibitors and chemopreventive agents", Prostaglandins, Leukotrienes and Essential FattyAcids (2002) 67(6), 461-465.

Hamza, Adel, et al., "Understanding human 15-hydroxyprostaglandin dehydrogenase binding with NAO+ and PGE2 by homology modeling, docking and molecular dynamics simulation", Bioorganic & Medicinal Chemistry 13 (2005) 1544-4551.

Berg, Daniel J., et al. "Rapid Development of Colitis in NSAID-Treated IL-10-Deficient Mice", Gastroenterology 2002; 123: 1527-1542.

Kabashima, Kenji, et al., "The prostaglandin receptor EP4 suppresses colitis, mucosal damage and CD4 cell activation in the gut", J_Clin. Invest. 109:883-893 (2002).

Berk, L.B., et al., "16, 16-Dimethyl Prostaglandin E2 and/or Syngeneic Bone Marrow Transplantation Increase Mouse Survival After Supra-Lethal Total Body Irradiation", Int. J Radiation Oncology Biol. Phys .. vol. 18. pp. 1387-1392.

Goessling, Wolfram, et al., "Prostaglandin E2 Enhances Human Cord Blood Stem Cell Xenotransplants and Shows Long-Term Safety in Preclinical Nonhuman Primate Transplant Models", Cell Stem Cell 8, 445-458, Apr. 8, 2011.

Porter, Rebecca L., et al., "Prostaglandin E2 Increases Hematopoietic Stem Cell Survival and Accelerates Hematopoietic Recovery After Radiation Injury", Stem Cells 2013;31:372-383.

Kurland, JI, et al., "prostaglandin E in the positive and negative feedback control of myeloid Role for monocyte-macrophage-derived colony-stimulating factor and stem cell proliferation" Blood 1978 52: 388-407.

Hoffman, Corey M., et al., "Minireview: Complexity of Hematopoietic Stem Cell Regulation in the Bone Marrow Microenvironmenl", Mol Endocrinol, 2014.

Hoggatt, Jonathan, et al., "Prostaglandin E2 enhances long-term repopulation but does not permanently alter inherent stem cell competitiveness," Blood 2013 122:2997-3000.

Frisch, Benjamin J., et al., "In vivo prostaglandin E2 treatment alters the bone marrow stem cells microenvironment and preferentially expands short-term hematopoietic", Blood 2009 114: 4054-4063.

Gentile, P., et al., "In vivo modulation of murine myelopoiesis following intravenous administration of prostaglandin E2", Blood 1983 62: 1100-1107.

Speth, Jennifer, et al., "Pharmacologic increase in HIF1a enhances hematopoietic stem and progenitor homing and engraftmenl", Blood 2014 123: 203-207.

Hoggatt, Jonathan, et al., "Prostaglandin E2 enhances hematopoietic stem cell homing, survival, and proliferation", Blood 2009 113: 5444-5455.

Hoggatt, Jonathan, et al., "Recovery from hematopoietic injury by modulating prostaglandin E2 signaling post-irradiation", Blood Cells, Molecules and Diseases 50 (2013) 147-153.

Pelus, Louis, M., et al., Pleiotropic effects of prostaglandin E2 in hematopoiesis; prostaglandin E2 and other eicosanoids regulate hematopoietic stem and progenitor cell function, Prostaglandins & other Lipid Mediators 96 (2011) 3-9.

Pelus, L.M., et al., "Pulse exposure of haematopoietic grafts to prostaglandin E2 in vitro facilitates engraftment and recovery", Cell Prolif., 2011, 44 (Suppl. 1) , 22-29.

(56) References Cited

OTHER PUBLICATIONS

Hoggatt, Jonathan, et al., "Differential stem- and progenitor-cell trafficking by prostaglandin E2", Nature, 2011.

Sasaki, S., et al., "Prostaglandin E2 Inhibits Lesion Formation in Dextran Sodium Sulphate-Induced Colitis in Rats and Reduces the Levels of Mucosal Inflammatory Cytokines", Scand. J_Immunol. 51, 23-28, 2000.

Tessner, Teresa, G., et al., "Prostaglandins Prevent Decreased Epithelial Cell Proliferation Associated With Dextran Sodium Sulfate Injury in Mice", Gastroenterology 1998;115:874-882.

Cutler, Corey, et al., "Prostaglandin-modulated umbilical cord blood hematopoietic stem cell transplantation" Blood, 2013.

Geossling, Wolfram, et al., "Genetic Interaction of PGE2 and Wnt Signaling Regulates Developmental Specification of Stem Cells and Regeneration", Cell 136, 1136-1147, Mar. 20, 2009.

Hagedorn, Elliott J., et al., "Getting more for your marrow: Boosting hematopoietic stem cell numbers with PGE2", BoostinghematopoieticstemcellnumberswithPGE2, Exp Cell Res (2014), http://dx.doi.org/10.1016/j.yexcr.2014.07.030.

North, Trista E., et al., "Prostaglandin E2 regulates vertebrate haematopoietic stem cell homeostasis", vol. 447, Jun. 21, 2007.

Karna, Sandeep,et al., "Novel Potent 15-Hydroxyprostaglandin Dehydrogenase Inhibitors", J_of Advanced Engineering and Technology, vol. 3, No. 3 (2010) pp. 301-304.

Castellone, Maria Domenica, et al., "Prostaglandin E2 Promotes Colon Cancer Cell Growth Through a Gs-Axin-II-Catenin Signaling Axis", Science, vol. 310, Dec. 2, 2005.

Zhang, Youngyou, et al. "Inhibition of the Prostaglandin Degrading Enzyme 15-PGDH Potentiates Tissue Regeneration" Science. Jun. 12, 2015; 348(6240): aaa2340. doi:10.1126/science.aaa2340.

Online"http://web.archive.org/web/20071219115313/http://www.akosgmbh.de/AKosSamples/index.html" 2011, accessed Oct. 10, 2015.

Frisch, Benjamin, et al., "In vivo prostaglandin E2 treatment alters the bone marrow microenvironment and preferentially expands short-term hematopoietic stem cells", Blood, Nov. 5, 2009 z vol. 114, No. 19, pp. 4054-4063.

Hoggati, Jonathan, et al., "Prostaglandin E2 enhances long-term repopulation but does not permanently alter inherent stem cell competitiveness", Blood, Oct. 24, 2013 x vol. 122, No. 17, pp. 2997-3000.

Jung, Peter, et al., "Isolation and in vitro expansion of human colonic stem cells", Nature Medicine 17, 1225-1227 (2011).

Brown, Jr, et al., "COX-2: a molecular target for colorectal cancer prevention", J_Clin Oneal. Apr. 20, 2005;23 (12):2840-55.

Kalugin "Functionalized sulfurcontaining compounds. 13.* Synthesis of substituted 3amino2(organylsulfinyl) and (organylsulfonyl)thieno[2,3b]pyridines." Russian Chemical Bulletin, International Edition, vol. 55, No. 3, pp. 529-534, Mar. 2006.

Pubchem Database compound CID 3337991, 2-butylsulfonyl-4-phenyl-6-thiophen-2-ylthieno[2,3-b]pyridin-3-amine, entered into the database on Sep. 7, 2005, Online "http://pubchem.ncbi.nlm.nih.gov/compound/3337991#section=Top" accessed Oct. 10, 2015.

PubChem Substance summary for CID 52943190 Deposit dale Jun. 16, 2011 (Jun. 16, 2011) p. 1.

PubChem Substance summary for CID 3337839 Deposit dale Sep. 7, 2005 (Sep. 7, 2005) p. 1.

A  In Vivo Exposure of a Bone Marrow Transplant Recipient to SW033291 Increases Survival

A

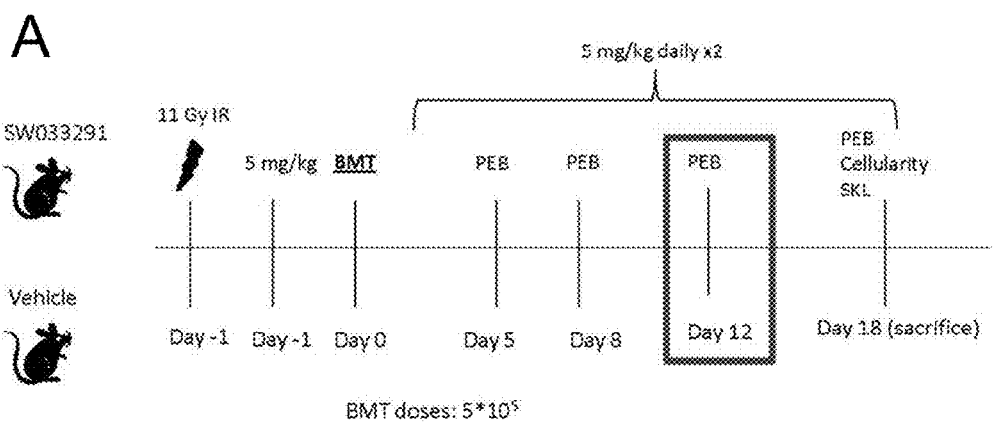
Fig. 8A
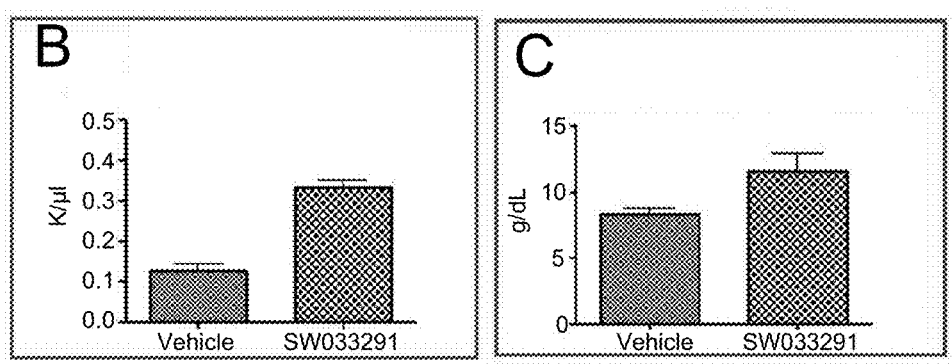
Figs. 8B-C
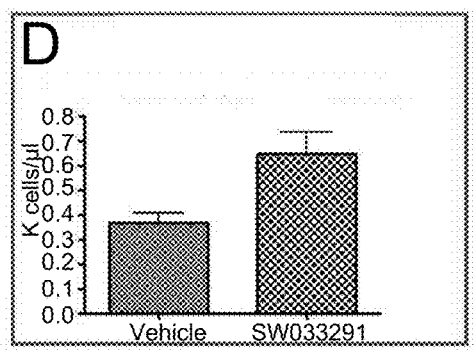
Figs. 8D

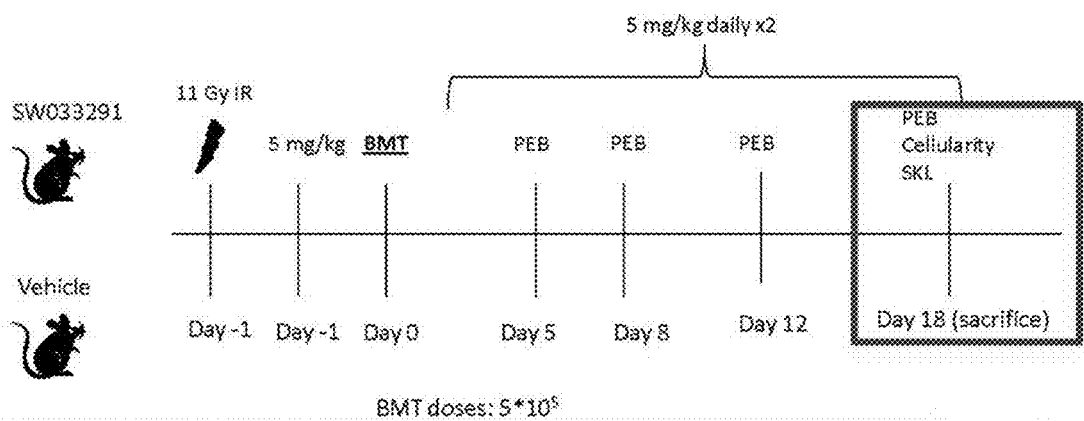
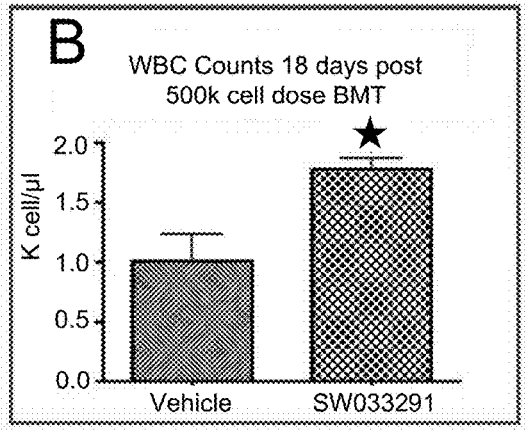
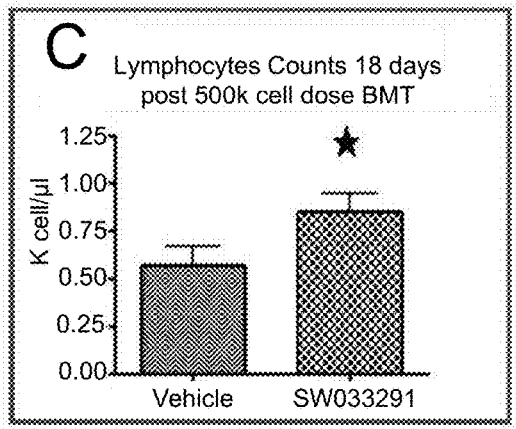
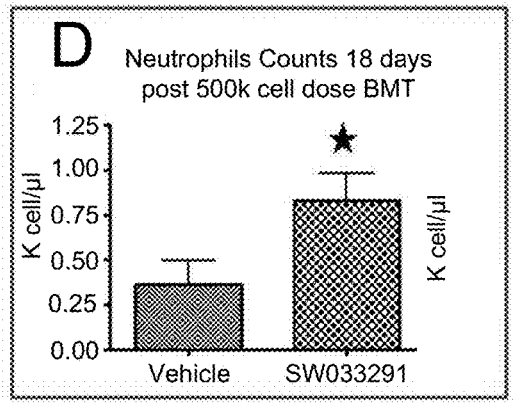
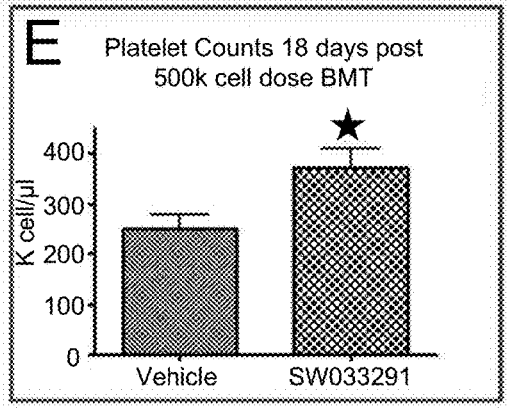
Figs. 9A-E

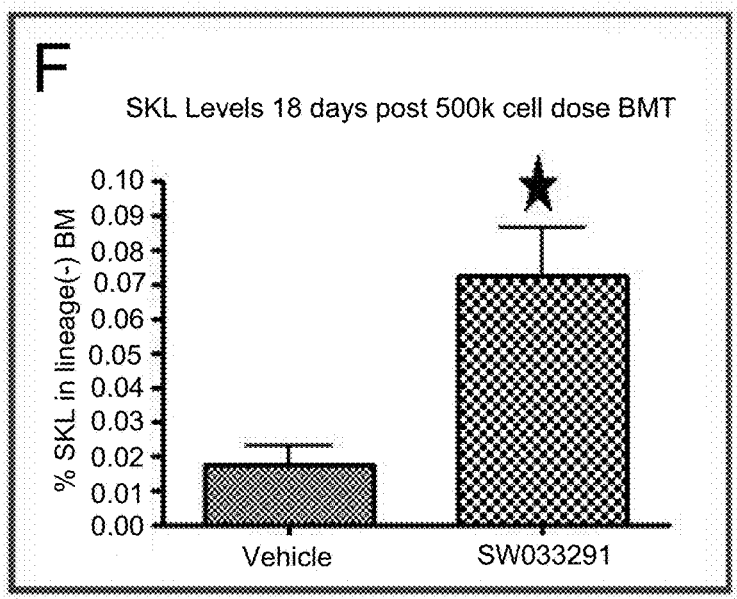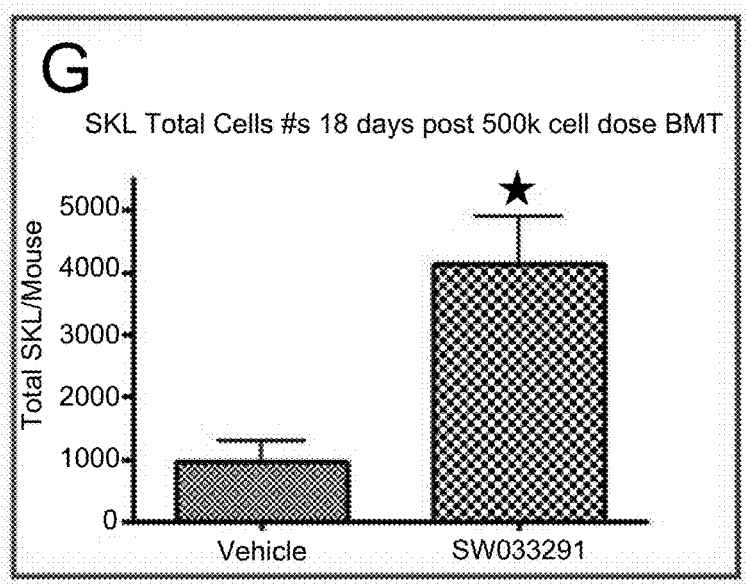
Figs. 9F-G

SW033291 Induction of PGE2 in Mouse Tissues
A. SW033291 (10mg/kg IP) Treated Mice
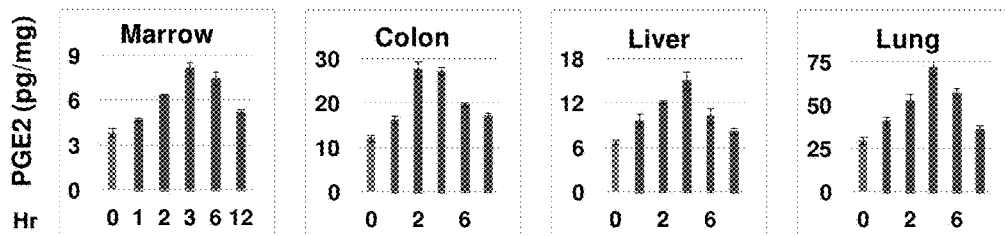
B. Vehicle Control Treated Mice
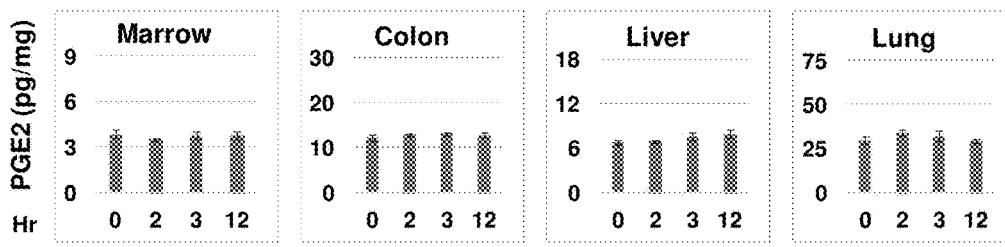
Figs. 10A-B
Hematopoietic Stem Cell Homing Assay
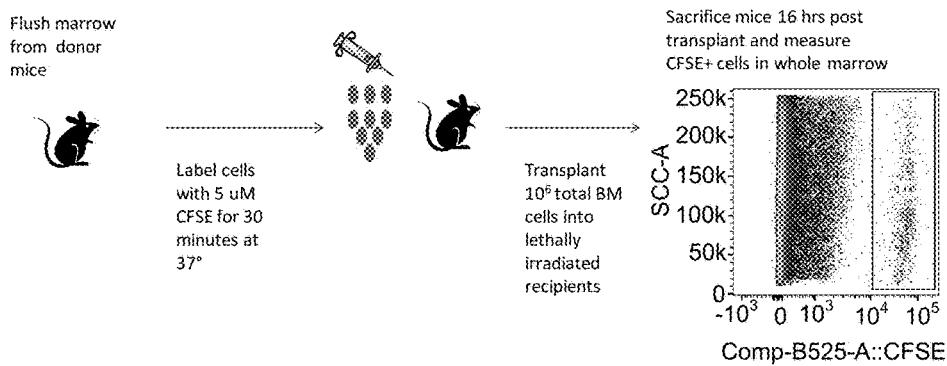
Mice receive either 10mg/kg SW033291, vehicle, or 5mg/kg Indomethacin + 10 mg/kg SW033291 immediately following lethal IR and BMT, and again 8 hours following BMT
Fig. 11

Hematopoietic Stem Cell Homing Assay-
16 hrs Post Transplant
(N=9 mice per group)

4 Groups:
-Vehicle
-10mg/kg SW033291
-10 ug/mouse EP2 Antagonist (PF-04418948) + SW033291
-10 ug/mouse EP4 Antagonist in( L-161,982)+ SW033291

Hematopoietic Stem Cell Homing Assay with
EP Receptor Antagonists
16 hrs Post Transplant
(N=9 mice per group)

N=3 Replicates

Gene Expression from Sorted SKL and Bone Marrow Stromal Cells after SW033291 Treatment
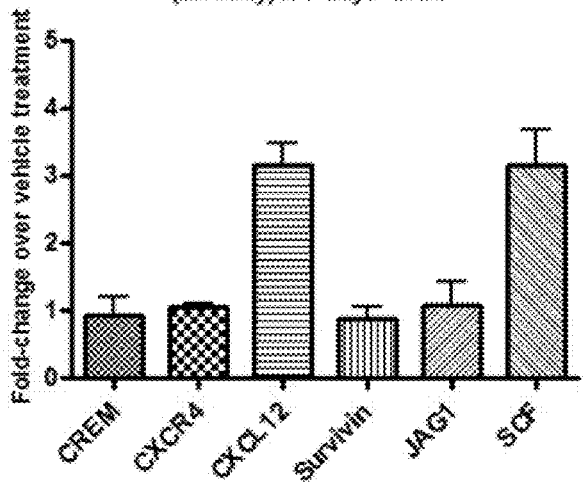
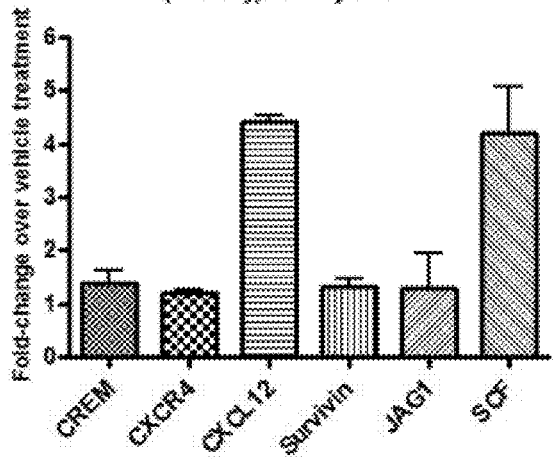
N = 3 replicates (9 mince per group)
Fig. 15

Hematopoietic Stem Cell Homing Assay with Human Umbilical Cord Blood

Mice receive either 10mg/kg SW033291 or vehicle immediately following sublethal IR and UCB transplant, and again 8 hours following UCB transplant

UCB Samples #1-3
Hematopoietic Stem Cell Homing Assay
16 hrs Post Transplant
(3 mice used for each of 3 human UCB samples)

P=.0334

Effects of GCSF + 415(+) on Steady State Hematopoiesis
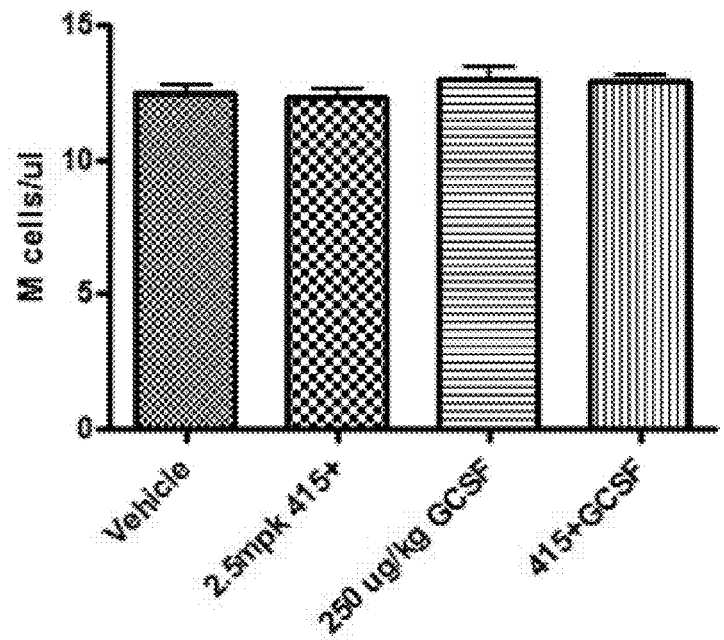
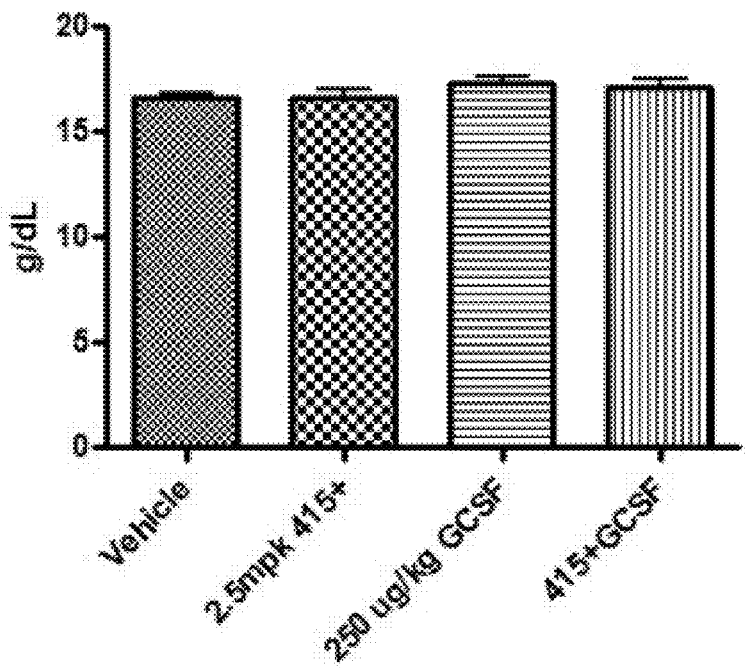
Fig. 20

Effects of GCSF + 415(+) on Steady State Hematopoiesis
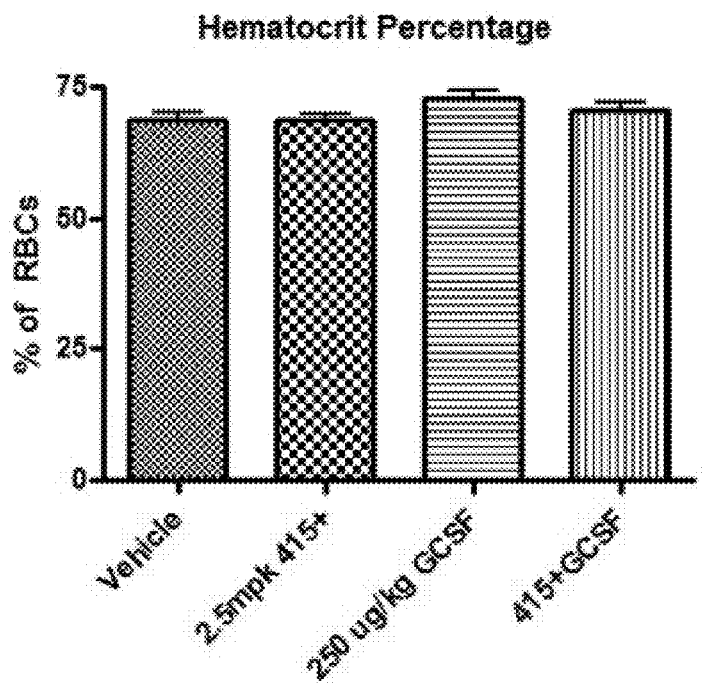
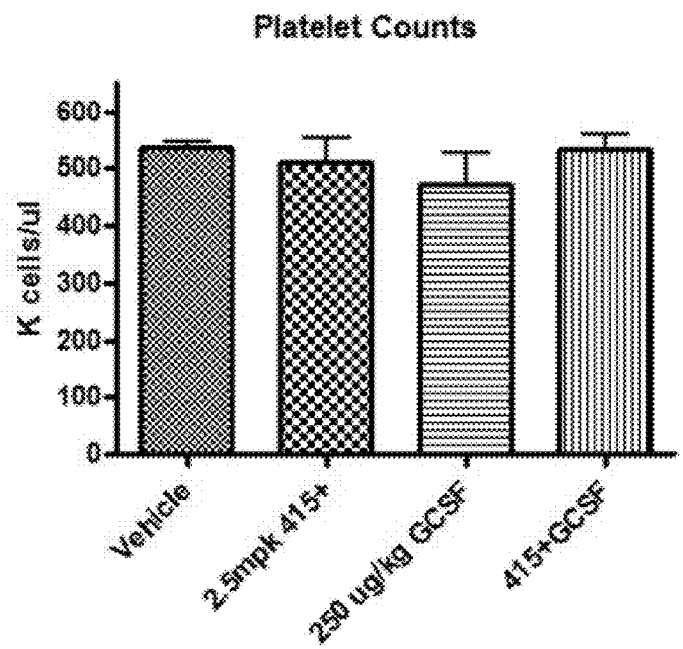
Fig. 20 (Continued)

SKL Frequency in Bone Marrow
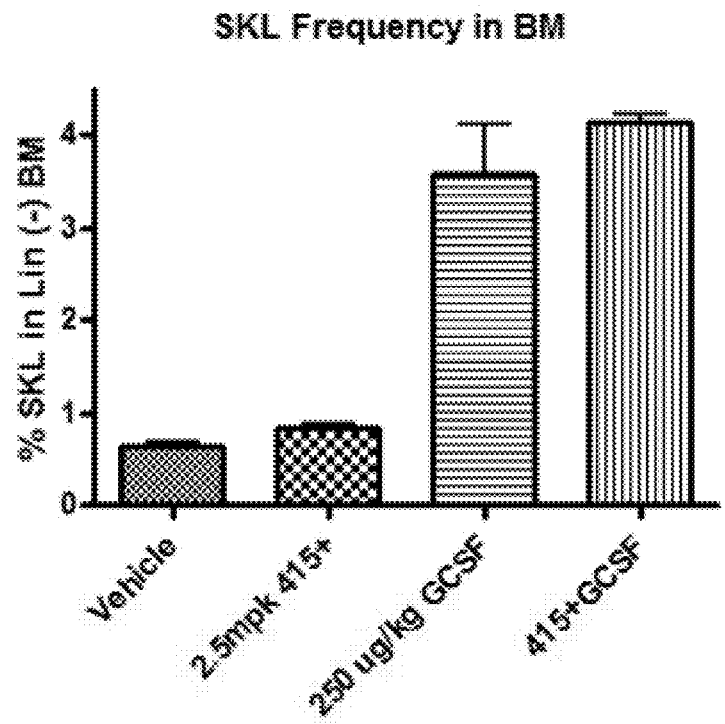
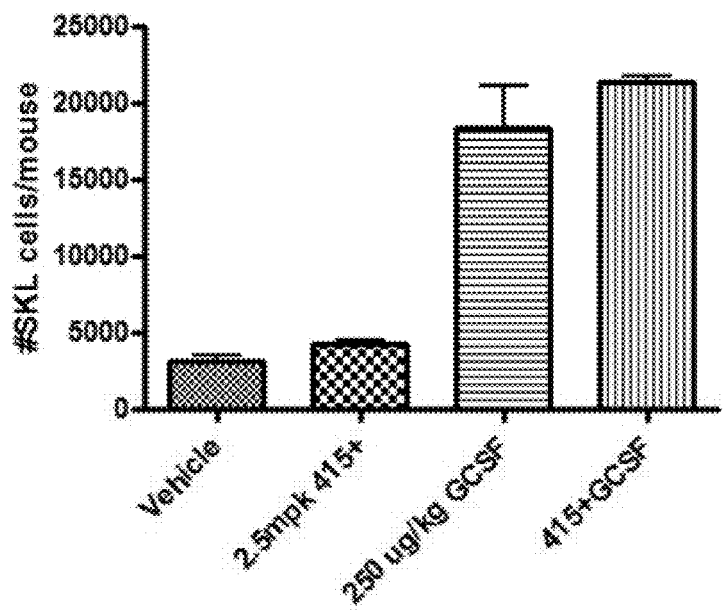
Fig. 22 (Continued)

INHIBITORS OF SHORT-CHAIN DEHYDROGENASE ACTIVITY FOR MODULATING HEMATOPOIETIC STEM CELLS AND HEMATOPOIESIS

RELATED APPLICATION

This application is a Continuation-in-part of U.S. patent application Ser. No. 14/395,021, filed Oct. 16, 2014, which is a National Phase Filing of PCT/US2013/036790, filed Apr. 16, 2013, which claims priority to U.S. Provisional Application Ser. No. 61/624,670, filed Apr. 16, 2012, this application is also a Continuation-in-Part of U.S. Ser. No. 15/029,943, filed Apr. 15, 2016, which is a National Phase Filing of PCT/US2014/060761, filed Oct. 16, 2014, which claims priority to U.S. Provisional Application Nos. 61/891,260, filed Oct. 15, 2013, 61/954,202, filed Mar. 17, 2014, 62/019,597, filed Jul. 1, 2014, and 62/043,694, filed Aug. 29, 2014, this application also claims priority to PCT/US2016/027549, filed Apr. 14, 2016, which claims priority to U.S. Provisional Application No. 62/129,885, filed Mar. 8, 2015, and this application also claims priority from U.S. Provisional Application No. 62/252,973, filed Nov. 9, 2015, the subject matter of which is incorporated herein by reference in its entirety.

GOVERNMENT FUNDING

This invention was made with government support under Grant No. R01CA127306, R01CA127306-0351, 1P01CA95471-10, AND 5P50CA150964 awarded by The National Institutes of Health. The United States government has certain rights in the invention.

BACKGROUND

Short-chain dehydrogenases (SCDs) are a family of dehydrogenases that share only 15% to 30% sequence identity, with similarity predominantly in the coenzyme binding domain and the substrate binding domain. In addition to their role in detoxification of ethanol, SCDs are involved in synthesis and degradation of fatty acids, steroids, and some prostaglandins, and are therefore implicated in a variety of disorders, such as lipid storage disease, myopathy, SCD deficiency, and certain genetic disorders.

The SCD, 15-hydroxy-prostaglandin dehydrogenase (15-PGDH), (hydroxyprostaglandin dehydrogenase 15-(nicotinamide adeninedinucleotide); 15-PGDH; Enzyme Commission number 1.1.1.141; encoded by the HPGD gene), represents the key enzyme in the inactivation of a number of active prostaglandins, leukotrienes and hydroxyeicosatetraenoic acids (HETEs) (e.g., by catalyzing oxidation of $PGE_2$ to 15-keto-prostaglandin E2, 15k-PGE). The human enzyme is encoded by the HPGD gene and consists of a homodimer with subunits of a size of 29 kDa. The enzyme belongs to the evolutionarily conserved superfamily of short-chain dehydrogenase/reductase enzymes (SDRs), and according to the recently approved nomenclature for human enzymes, it is named SDR36C1. Thus far, two forms of 15-PGDH enzyme activity have been identified, NAD+-dependent type I 15-PGDH that is encoded by the HPGD gene, and the type II NADP-dependent 15-PGDH, also known as carbonyl reductase 1 (CBR1, SDR21C1). However, the preference of CBR1 for NADP and the high Km values of CBR1 for most prostaglandin suggest that the majority of the in vivo activity can be attributed to type I 15-PGDH encoded by the HPGD gene, that hereafter, and throughout all following text, simply denoted as 15-PGDH.

SUMMARY

Embodiments described herein relate to compositions and methods for modulating hematopoietic stem cells and hematopoiesis. As described in the Examples below, it was found that that inhibitors of short-chain dehydrogenase activity, such as 15-PGDH inhibitors, can be administered to a subject in need thereof, cells of the subject, and/or tissue of the subject alone or in combination with a cytokine to increase and/or mobilize hematopoietic stem cells and/or neutrophils in the blood, marrow, and/or tissue of the subject.

In some embodiments, the administration of a 15-PGDH inhibitor alone or in combination with a cytokine, hematopoietic cytokine, and/or cell mobilization agent to a subject in need thereof, cells of the subject, and/or tissue of the subject can be used for the purpose of increasing neutrophils in the subject. For example, the hematopoietic cytokine or cell mobilization agent can include at least one of G-CSF or Plerixafor.

In other embodiments, the administration of a 15-PGDH inhibitor alone or in combination with a cytokine, hematopoietic cytokine, and/or cell mobilization agent to a subject in need thereof, cells of the subject, and/or tissue of the subject can be used for the purpose of increasing numbers of and/or of mobilizing peripheral blood hematopoietic stem cells in the subject. For example, the hematopoietic cytokine or cell mobilization agent can include at least one of G-CSF or Plerixafor.

In still other embodiments, the administration of a 15-PGDH inhibitor alone or in combination with a cytokine, hematopoietic cytokine, and/or cell mobilization agent to a subject in need thereof, cells of the subject, and/or tissue of the subject can be used for the purpose of increasing numbers of hematopoietic stem cells in blood or bone marrow of the subject. For example, the hematopoietic cytokine or cell mobilization agent can include at least one of G-CSF or Plerixafor.

In other embodiments, the 15-PGDH inhibitor can be administered to a subject and/or tissue of the subject to increase tissue stem cells. For example, the 15-PGDH inhibitor can be administered to bone marrow of a subject to increase stem cells in the subject.

In still other embodiments, the 15-PGDH inhibitor can be administered to a tissue graft donor, bone marrow graft donor, and/or a hematopoietic stem cell donor, and/or a tissue graft, and/or a bone marrow graft, and/or a hematopoietic stem cell graft, to increase the fitness of a donor tissue graft, a donor bone marrow graft, and/or a donor hematopoietic stem cell graft. For example, the 15-PGDH inhibitor can be administered to a subject, and/or bone marrow of a subject to increase the fitness of the marrow as a donor graft, and/or to a preparation of hematopoietic stem cells of a subject to increase the fitness of the stem cell preparation as a donor graft, and/or to a preparation of peripheral blood hematopoietic stem cells of a subject to increase the fitness of the stem cell preparation as a donor graft, and/or to a preparation of umbilical cord blood stem cells to increase the fitness of the stem cell preparation as a donor graft, and/or to a preparation of umbilical cord blood stem cells to decrease the number of units of umbilical cord blood required for transplantation.

In other embodiments, the 15-PGDH inhibitor can be administered to a recipient of a tissue graft transplant, bone marrow transplant, hematopoietic stem cell transplant, and/ or of an umbilical cord stem cell transplant, in order to decrease the administration of other treatments or growth factors.

In still other embodiments, the 15-PGDH inhibitor can be administered to a subject to increase neutrophil counts following a hematopoietic cell transplant with bone marrow, hematopoietic stem cells, or umbilical cord blood, to increase neutrophil counts in a subject with neutropenia following chemotherapy administration or radiation therapy, to increase neutrophil counts in a subject with aplastic anemia, myelodysplasia, myelofibrosis, neutropenia due to other bone marrow diseases, drug induced neutropenia, autoimmune neutropenia, idiopathic neutropenia, or neutropenia following viral infections, to increase neutrophil counts in a subject with neutropenia, to increase platelet counts following a hematopoietic cell transplant with bone marrow, hematopoietic stem cells, or umbilical cord blood, to increase platelet counts in a subject with thrombocytopenia following chemotherapy administration or radiation therapy, to increase platelet counts in a subject with aplastic anemia, myelodysplasia, myelofibrosis, thrombocytopenia due to other bone marrow diseases, drug induced thrombocytopenia, autoimmune thrombocytopenia, idiopathic thrombocytopenic purpura, idiopathic thrombocytopenia, or thrombocytopenia following viral infections, to increase platelet counts in a subject with thrombocytopenia, to increase red blood cell counts, or hematocrit, or hemoglobin level, following a hematopoietic cell transplant with bone marrow, hematopoietic stem cells, or umbilical cord blood, to increase red blood cell counts, or hematocrit, or hemoglobin level in a subject with anemia following chemotherapy administration or radiation therapy, to increase red blood cell counts, or hematocrit, or hemoglobin level counts in a subject with aplastic anemia, myelodysplasia, myelofibrosis, anemia due to other disorder of bone marrow, drug induced anemia, immune mediated anemias, anemia of chronic disease, anemia following viral infections, or anemia of unknown cause, to increase red blood cell counts, or hematocrit, or hemoglobin level in a subject with anemia, to increase bone marrow stem cells, following a hematopoietic cell transplant with bone marrow, hematopoietic stem cells, or umbilical cord blood, to increase bone marrow stem cells in a subject following chemotherapy administration or radiation therapy, and/or to increase bone marrow stem cells in a subject with aplastic anemia, myelodysplasia, myelofibrosis, other disorder of bone marrow, drug induced cytopenias, immune cytopenias, cytopenias following viral infections, or cytopenias.

In other embodiments, the 15-PGDH inhibitor can be administered to a subject having or at risk of presence of cytopenia, neutropenia, thrombocytopenia, lymphocytopenia and anemia to increase responsiveness and/or potentiate cytokines, such as hematopoietic cytokines. The cytokines can include, for example, G-CSF, GM-CSF, EPO, IL-3, IL-6, TPO, TPO-RA (thrombopoietin receptor agonist), and SCF.

In some embodiments, the subject has received a hematopoietic stem cell transplant, bone marrow transplant, chemotherapy, a myelosuppressive therapy, radiation therapy, or viral therapy and/or has a bone marrow disease, cancer, viral infection, aplastic anemia, myelodysplasia, and/or myelofibrosis.

Other embodiments relate to a method of treating at least one of neutropenia, thrombocytopenia, anemia, or cytopenia in a subject in need thereof by administering to the subject a therapeutically effective amount of a15-PGDH inhibitor.

The 15-PGDH inhibitor can be administered alone or in combination with a cytokine, hematopoietic cytokine, and/ or cell mobilization agent to the subject, cells of the subject, and/or tissue of the subject.

In some embodiments, the 15-PGDH inhibitor can be administered to a blood, bone marrow, and/or tissue of a subject at an amount effective to increase prostaglandin levels in the subject. The 15-PGDH inhibitor can include a compound having formula (I):

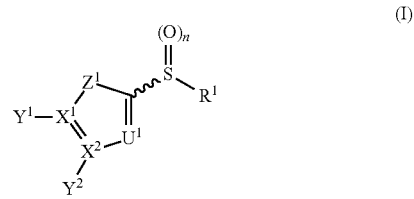

wherein n is 0-2;

$Y^1$, $Y^2$, and $R^1$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$ =C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof, and wherein $Y^1$ and $Y^2$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—NR$^3$R$^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

$X^1$ and $X^2$ are independently N or C, and wherein when $X^1$ and/or $X^2$ are N, $Y^1$ and/or $Y^2$, respectively, are absent;

$Z^1$ is O, S, CR$^a$R$^b$ or NR$^a$, wherein R$^a$ and R$^b$ are independently H or a C$_{1-8}$ alkyl, which is linear, branched, or cyclic, and which is unsubstituted or substituted;

and pharmaceutically acceptable salts thereof.

In other embodiments, the 15-PGDH inhibitor can include a compound having the following formula (V):

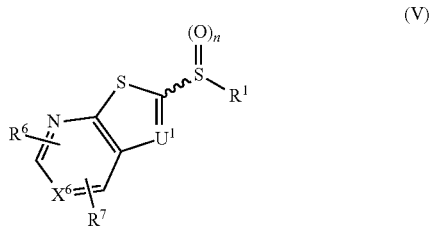

wherein n is 0-2

$X^6$ is independently is N or CR$^c$ $R^1$, $R^6$, $R^7$, and $R^c$ are each independently selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH2, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—R$^2$, or C—NR$^3$R$^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

and pharmaceutically acceptable salts thereof.

In some embodiments, $R^1$ is selected from the group consisting of branched or linear alkyl including —(CH$_2$)$_{n1}$CH$_3$ (n$_1$=0-7),

wherein n$_2$=0-6 and X is any of the following: CF$_y$H$_z$ (y+z=3), CCl$_y$H$_z$ (y+z=3), OH, OAc, OMe, R$^{71}$, OR$^{72}$, CN, N(R$^{73}$)$_2$,

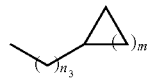

(n$_3$=0-5, m=1-5), and

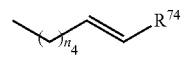

(n$_4$=0-5).

In other embodiments, $R^6$ and $R^7$ can each independently be one of the following:

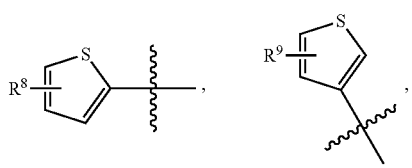

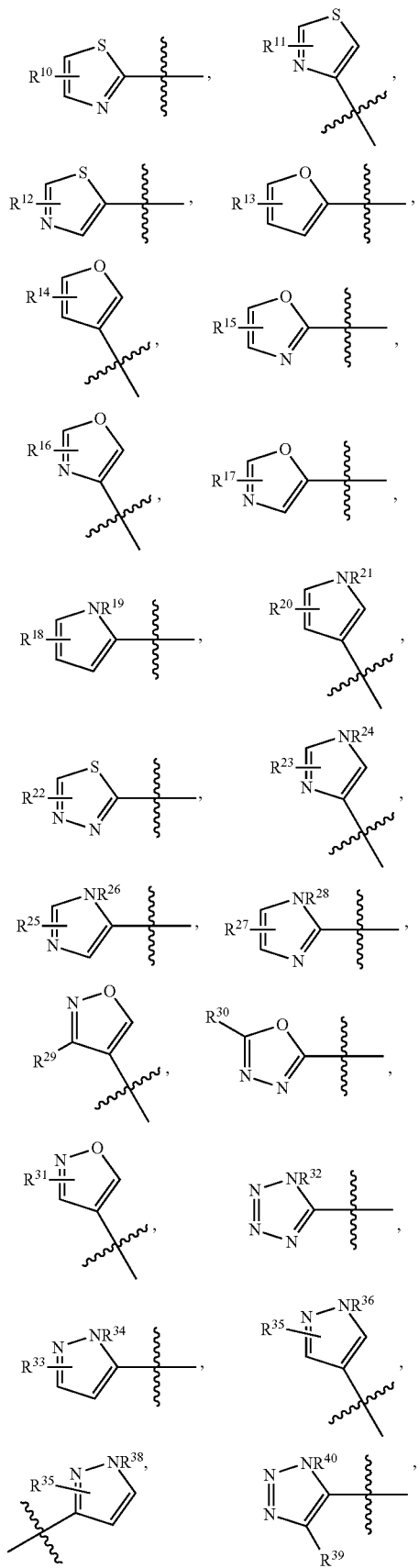
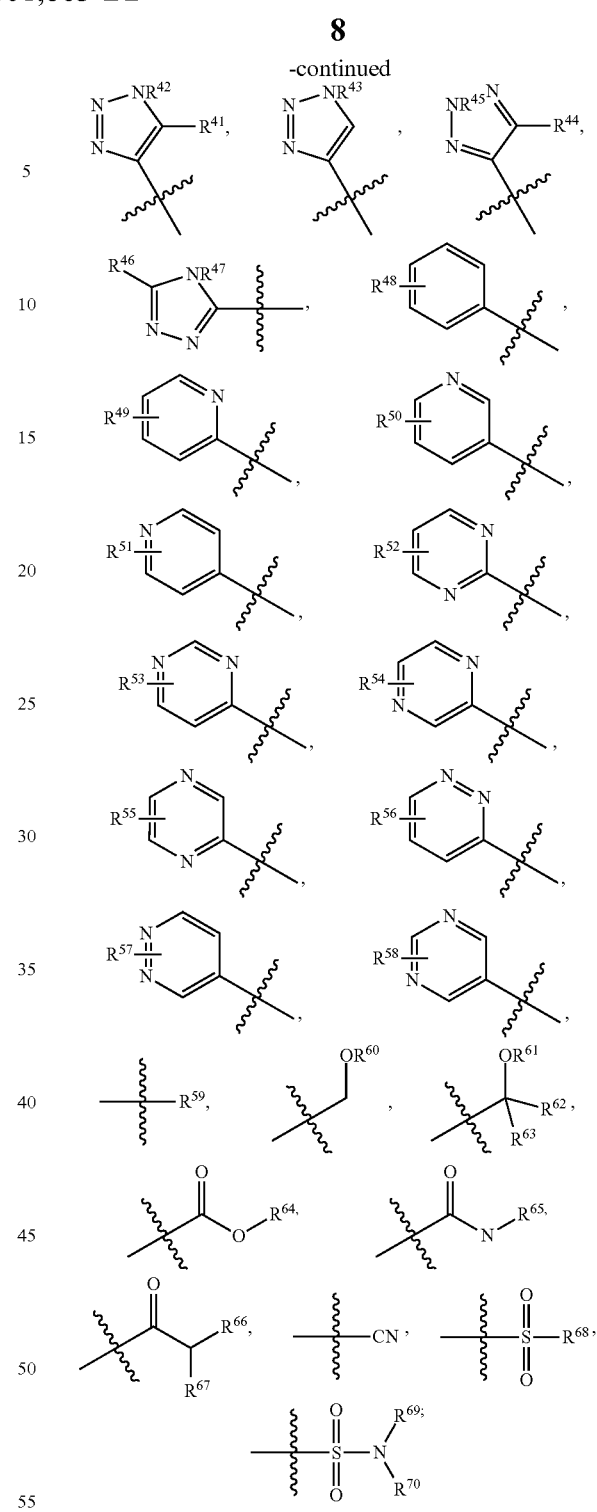

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C⁻), cyanato (—O—CN), isocyanato (—O—N$^+$=C⁻), isothiocyanato (—S—CN), azido (—N=N$^+$=N⁻), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O⁻)$_2$), phosphinato (—P(O)(O⁻)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In some embodiments, the 15-PGDH inhibitor can inhibit the enzymatic activity of recombinant 15-PGDH at an IC$_{50}$ of less than 1 µM, or preferably at an IC$_{50}$ of less than 250 nM, or more preferably at an IC$_{50}$ of less than 50 nM, or more preferably at an IC$_{50}$ of less than 10 nM, or more preferably at an IC$_{50}$ of less than 5 nM at a recombinant 15-PGDH concentration of about 5 nM to about 10 nM.

BRIEF DESCRIPTION OF THE DRAWINGS

FIGS. 8(A-D) illustrate: (A) a schematic illustration showing measurements on blood and bone marrow on day 12 after transplant; (B) a graph showing that SW033291 treated mice have significantly higher neutrophil counts, with drug treated mice having 332 neutrophils compared to control mice having 125 neutrophils; and (C) a graph showing that on day 12 after transplant, SW033291 treated mice have significantly higher hemoglobin count than controls, with drug treated mice having hemoglobin level of 11.58 and control mice having hemoglobin level of 8.3; and D) a graph showing that SW033291 treated mice have significantly higher total white counts compared to control mice. The star symbol denotes $P<0.05$.

FIGS. 9(A-G) illustrate: (A) a schematic illustration showing measurements on blood and bone marrow on day 18 after transplant; (B-D) graphs showing SW033291 treated mice have significantly higher total white count (FIG. 85B), lymphocyte count (FIG. 85C), and neutrophil count (FIG. 85D), with drug treated mice having 835 neutrophils and control mice having 365 neutrophils (FIG. 85D); (E) a graph showing that on day 18 drug treated mice have significantly higher platelet counts than control mice; and (F-G) graphs showing drug treated mice have nearly 4-fold increased percentage (FIG. 85F) and total numbers (FIG. 85G) of SKL marked bone marrow stem cells than do control mice. The star symbol denotes $P<0.05$.

FIGS. 10(A-B) illustrate graphs showing (A) measurement of PGE2 (pg of PGE2/mg tissue protein) in 4 different mouse tissues (colon, bone marrow, liver, lung) across time following IP injection of SW033291 at 10 mg/kg; and (B) time course of PGE2 in control mice injected with vehicle only.

FIG. 11 is a schematic illustration showing an experiment in which mice are lethally irradiated (IR) and 12 hours later receive a transplant (BMT) with CFSE dye labeled bone marrow cells (BM), and the number of transplanted cells that home and survive in the bone marrow of the recipient mice are then determined by FACS at 16 hours post-transplant.

FIGS. 15(A-B) illustrate graphs showing induction of gene expression in (A) bone marrow SKL cells and (B) bone marrow stromal cells of mice injected with SW033291 twice daily IP at 10 mg/kg for 3 days.

FIG. 20 illustrates graphs showing total counts of red blood cells, hematocrit, hemoglobin, and platelets of mice administered 15-PGDH inhibitor (+) SW209415 and/or G-CSF as described in FIG. 18.

DETAILED DESCRIPTION

Figure 1:
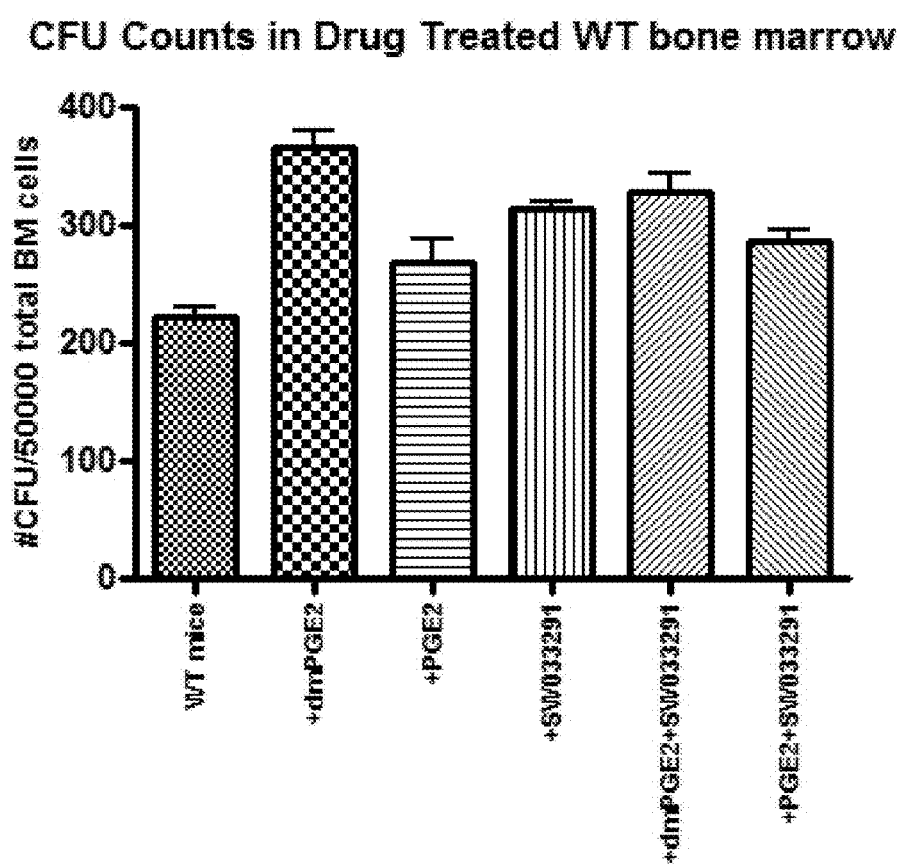
FIG. 1 illustrates a graph showing CFU counts in wild type bone marrow treated with SW033291 and PGE-2.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n-1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same.

"Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Non-limiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano(-CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

The term "nucleic acid" refers to polynucleotides such as deoxyribonucleic acid (DNA), and, where appropriate, ribonucleic acid (RNA). The term should also be understood to include analogues of either RNA or DNA made from nucleotide analogues, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

Embodiments described herein relate to compositions and methods for modulating hematopoietic stem cells and hematopoiesis. As described in the Examples below, it was found that that inhibitors of short-chain dehydrogenase activity, such as 15-PGDH inhibitors, can be administered to a subject in need thereof, cells of the subject, and/or tissue of the subject alone or in combination with a cytokine to increase and/or mobilize hematopoietic stem cells and/or neutrophils in the blood, marrow, and/or tissue of the subject.

In some embodiments, the 15-PGDH inhibitor can be administered to the subject or a preparation of hematopoietic stem cells, such as peripheral blood hematopoietic stem cells or umbilical cord stem cells of the subject, to increase the fitness of the stem cell preparation as a donor graft or to decrease the number of units of umbilical cord blood required for transplantation.

Hematopoietic stem cells are multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al, U.S. Pat. No. 5,635,387; McGlave, et al, U.S. Pat. No. 5,460,964; Simmons, P., et al, U.S. Pat. No. 5,677,136; Tsukamoto, et al, U.S. Pat. No. 5,750,397; Schwartz, et al, U.S. Pat. No. 5,759,793; DiGuisto, et al, U.S. Pat. No. 5,681,599; Tsukamoto, et al, U.S. Pat. No. 5,716,827). Hematopoietic stem cells (HSCs) give rise to committed hematopoietic progenitor cells (HPCs) that are capable of generating the entire repertoire of mature blood cells over the lifetime of an organism.

Hematopoietic stem cells and hematopoietic progenitor cells are described herein generally as hematopoietic stem cells unless noted otherwise and can refer to cells or populations identified by the presence of the antigenic marker CD34 ($CD34^+$). In some embodiments, the hematopoietic stem cells can be identified by the presence of the antigenic marker CD34 and the absence of lineage (lin) markers and are therefore characterized as $CD34^+/lin^-$ cells.

The hematopoietic stem cells used in the methods described herein may be obtained from any suitable source of hematopoietic stem and progenitor cells and can be provided as a high purified population of hematopoietic stem cells or as composition that includes about 0.01% to about 100% of hematopoietic stem cells. For example, hematopoietic stem cells may be provided in compositions, such as unfractionated bone marrow (where the hematopoietic stem cells comprise less than about 1% of the bone marrow cell population), umbilical cord blood, placental blood, placenta, fetal blood, fetal liver, fetal spleen, Wharton's jelly, or mobilized peripheral blood.

Suitable sources of hematopoietic stem cells can be isolated or obtained from an organ of the body containing cells of hematopoietic origin. The isolated cells can include cells that are removed from their original environment. For example, a cell is isolated if it is separated from some or all of the components that normally accompany it in its native state. For example, an "isolated population of cells," an "isolated source of cells," or "isolated hematopoietic stem cells" and the like, as used herein, refer to in vitro or ex vivo separation of one or more cells from their natural cellular environment, and from association with other components of the tissue or organ, i.e., it is not significantly associated with in vivo substances.

Hematopoietic stem cells can be obtained or isolated from bone marrow of adults, which includes femurs, hip, ribs, sternum, and other bones. Bone marrow aspirates containing hematopoietic stem cells can be obtained or isolated directly from the hip using a needle and syringe. Other sources of hematopoietic stem cells include umbilical cord blood, placental blood, mobilized peripheral blood, Wharton's jelly, placenta, fetal blood, fetal liver, or fetal spleen. In particular embodiments, harvesting a sufficient quantity of hematopoietic stem cells for use in therapeutic applications may require mobilizing the stem and progenitor cells in the donor.

"Hematopoietic stem cell mobilization" refers to the release of stem cells from the bone marrow into the peripheral blood circulation for the purpose of leukapheresis, prior to stem cell transplantation. By increasing the number of stem cells harvested from the donor, the number of stem cells available for therapeutic applications can be significantly improved. Hematopoietic growth factors, e.g., granulocyte colony stimulating factor (G-CSF) or chemotherapeutic agents often are used to stimulate the mobilization. Commercial cell mobilization agents exist and can be used in combination with G-CSF to mobilize sufficient quantities of hematopoietic stem and progenitor cells for transplantation into a subject. For example, G-CSF and MOZOBIL (Plerixafor, Genzyme Corporation) can be administered to a donor in order to harvest a sufficient number of hematopoietic cells for transplantation. Other methods of mobilizing hematopoietic stem cells would be apparent to one having skill in the art.

In some embodiments, hematopoietic stem cells are obtained from umbilical cord blood. Cord blood can be harvested according to techniques known in the art (see, e.g., U.S. Pat. Nos. 7,147,626 and 7,131,958, herein incorporated by reference for such methodologies).

In one embodiment, hematopoietic stem cells can be obtained from pluripotent stem cell sources, e.g., induced pluripotent stem cells (iPSCs) and embryonic stem cells (ESCs). As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell. As used herein, the term "reprogramming" refers to a method of increasing the potency of a cell to a less differentiated state. As used herein, the term "programming" refers to a method of decreasing the potency of a cell or differentiating the cell to a more differentiated state.

In some embodiments, the 15-PGDH inhibitor can be administered to the subject or to hematopoietic stem cells, which can be administered or contacted ex vivo with one or more 15-PGDH inhibitors described herein to provide a therapeutic composition. In one embodiment, the therapeutic compositions or preparations can include the 15-PGDH inhibitor or a population of hematopoietic stem cells treated ex vivo with a one or more 15-PGDH inhibitor. In certain embodiments, the therapeutic composition including the enhanced hematopoietic stem cells can include whole bone marrow, umbilical cord blood, or mobilized peripheral blood.

In particular embodiments, the therapeutic composition includes a population of cells, wherein the population of cells is about 95% to about 100% hematopoietic stem cells. The use of therapeutic compositions of highly purified hematopoietic stem cells, e.g., a composition comprising a population of cells wherein the cells comprise about 95% hematopoietic stem cells, may improve the efficiency of stem cell therapies. Currently practiced methods of transplantations typically use unfractionated mixtures of cells where hematopoietic stem cells comprise less than 1% of the total cell population.

In some embodiments, the therapeutic composition comprises a population of cells, wherein the population of cells comprises less than about 0.1%, 0.5%, 1%, 2%, 5%, 10%, 15%, 20%, 25%, or 30% hematopoietic stem cells. The population of cells in other embodiments comprises more than about 0.1%, 0.5%, 1%, 2%, 5%, 10%, 15%, 20%, 25%, or 30% hematopoietic stem cells. In still other embodiments, the population of cells is about 0.1% to about 1%, about 1% to about 3%, about 3% to about 5%, about 10%-15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% hematopoietic stem cells.

Hematopoietic stem cells in the therapeutic compositions described herein can be autologous/autogeneic ("self") or non-autologous ("non-self," e.g., allogeneic, syngeneic or xenogeneic) relative to a subject to which the therapeutic composition is to be administered. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison.

Hematopoietic stem cells for use in the methods described herein may be depleted of mature hematopoietic cells, such as T cells, B cells, NK cells, dendritic cells, monocytes, granulocytes, erythroid cells, and their committed precursors from bone marrow aspirate, umbilical cord blood, or mobilized peripheral blood (mobilized leukapheresis product). Mature, lineage committed cells are depleted by immunodepletion, for example, by labeling solid substrates with antibodies that bind to a panel of so-called "lineage" antigens: CD2, CD3, CD11b, CD14, CD15, CD16, CD79, CD56, CD123, and CD235a. A subsequent step can be performed to further purify the population of cells, in which a substrate labeled with antibodies that bind to the $CD34^+$ antigen are used to isolate primitive hematopoietic stem cells. Kits are commercially available for purifying stem and progenitor cells from various cell sources and in particular embodiments, these kits are suitable for use with the methods described herein.

In one embodiment, the amount of hematopoietic stem cells in the therapeutic composition is at least $0.1 \times 10^5$ cells, at least $0.5 \times 10^5$ cells, at least $1 \times 10^5$ cells, at least $5 \times 10^5$ cells, at least $10 \times 10^5$ cells, at least $0.5 \times 10^6$ cells, at least $0.75 \times 10^6$ cells, at least $1 \times 10^6$ cells, at least $1.25 \times 10^6$ cells, at least $1.5 \times 10^6$ cells, at least $1.75 \times 10^6$ cells, at least $2 \times 10^6$ cells, at least $2.5 \times 10^6$ cells, at least $3 \times 10^6$ cells, at least $4 \times 10^6$ cells, at least $5 \times 10^6$ cells, at least $10 \times 10^6$ cells, at least $15 \times 10^6$ cells, at least $20 \times 10^6$ cells, at least $25 \times 10^6$ cells, or at least $30 \times 10^6$ cells.

In one embodiment, the amount of hematopoietic stem cells in the therapeutic composition is the amount of hematopoietic stem cells in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.5 \times 10^6$ cells/kg of bodyweight, at least $0.75 \times 10^6$ cells/kg of bodyweight, at least $1 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, or at least $30 \times 10^6$ cells/kg of bodyweight.

Preparations of the 15-PGDH inhibitor as well as hematopoietic stem cells administered one or more 15-PGDH inhibitors and/or therapeutic compositions that include hematopoietic stem cells and one or more 15-PGDH inhibitor can be used for improving hematopoietic stem cell transplants and in treating ischemia or ischemia-damaged tissue, and in reducing further damage to ischemic tissue and/or repairing damage to ischemic tissue through cell recruitment, improving vascularization in ischemic tissue, improving tissue regeneration at sites of ischemia, decreasing ischemic tissue necrosis or apoptosis, and/or increasing cell survival at sites of ischemia. In particular embodiments, the preparations of 15-PGDH inhibitor, 15-PGDH inhibitor treated hematopoietic stem cells, and/or therapeutic compositions of 15-PGDH inhibitors and hematopoietic stem cells are useful to subjects in need of hematopoietic reconstitution, such as subjects that have undergone or are scheduled to undergo myeloablative therapy.

Subjects, who can be treated with the preparations of 15-PGDH inhibitor, 15-PGDH inhibitor treated hematopoietic stem cells and/or therapeutic compositions of 15-PGDH inhibitors and hematopoietic stem cells, can include subjects that have or that have been diagnosed with various types of leukemias, anemias, lymphomas, myelomas, immune deficiency disorders, and solid tumors. A subject also includes a human who is a candidate for stem cell transplant or bone marrow transplantation, such as during the course of treatment for a malignant disease or a component of gene therapy. Subjects may also include individuals or animals that donate stem cells or bone marrow for allogeneic transplantation. In certain embodiments, a subject may have undergone myeloablative irradiation therapy or chemotherapy, or may have experienced an acute radiation or chemical insult resulting in myeloablation. In certain embodiments, a subject may have undergone irradiation therapy or chemotherapy, such as during various cancer treatments. Typical subjects include animals that exhibit aberrant amounts (lower or higher amounts than a "normal" or "healthy" subject) of one or more physiological activities that can be modulated by an agent or a stem cell or marrow transplant.

Subjects, which can be treated with the preparations of 15-PGDH inhibitors, 15-PGDH inhibitor treated hematopoietic stem cells and/or therapeutic compositions of 15-PGDH inhibitors and hematopoietic stem cells, can also include subjects undergoing chemotherapy or radiation therapy for cancer, as well as subjects suffering from (e.g., afflicted with) non malignant blood disorders, particularly immunodeficiencies (e.g. SCID, Fanconi's anemia, severe aplastic anemia, or congenital hemoglobinopathies, or metabolic storage diseases, such as Hurler's disease, Hunter's disease, mannosidosis, among others) or cancer, particularly hematological malignancies, such as acute leukemia, chronic leukemia (myeloid or lymphoid), lymphoma (Hodgkin's or non-Hodgkin's), multiple myeloma, myelodysplastic syndrome, or non-hematological cancers, such as solid tumors (including breast cancer, ovarian cancer, brain cancer, prostate cancer, lung cancer, colon cancer, skin cancer, liver cancer, or pancreatic cancer).

Subjects may also include subjects suffering from aplastic anemia, an immune disorder (severe combined immune deficiency syndrome or lupus), myelodysplasia, thalassemaia, sickle-cell disease or Wiskott-Aldrich syndrome. In some embodiments, the subject suffers from a disorder that is the result of an undesired side effect or complication of another primary treatment, such as radiation therapy, chemotherapy, or treatment with a bone marrow suppressive drug, such as zidovadine, chloramphenical or gangciclovir. Such disorders include neutropenias, anemias, thrombocytopenia, and immune dysfunction. Other subjects may have disorders caused by an infection (e.g., viral infection, bacterial infection or fungal infection) which causes damage to stem or progenitor cells of the bone marrow.

In addition, subjects suffering from the following conditions can also benefit from treatment using the preparations of 15-PGDH inhibitor, 15-PGDH inhibitor treated hematopoietic stem cells and/or therapeutic compositions of 15-PGDH inhibitors and hematopoietic stem cells: lymphocytopenia, lymphorrhea, lymphostasis, erythrocytopenia, erthrodegenerative disorders, erythroblastopenia, leukoerythroblastosis; erythroclasis, thalassemia, myelodysplasia, myelofibrosis, thrombocytopenia, disseminated intravascular coagulation (DIC), immune (autoimmune) thrombocytopenic purpura (ITP), HIV inducted ITP, myelodysplasia; thrombocytotic disease, thrombocytosis, congenital neutropenias (such as Kostmann's syndrome and Schwachman-Diamond syndrome), neoplastic associated neutropenias, childhood and adult cyclic neutropaenia; post-infective neutropaenia; myelodysplastic syndrome; neutropaenia associated with chemotherapy and radiotherapy; chronic granulomatous disease; mucopolysaccharidoses; Diamond Blackfan Anemia; Sickle cell disease; or Beta thalassemia major.

In other embodiments, the preparations of 15-PGDH inhibitor, 15-PGDH inhibitor treated hematopoietic stem cells, and/or therapeutic compositions or 15-PGDH inhibitors and hematopoietic stem cells can be used in cell-based therapy for treating ischemic tissue or treating or ameliorating one or more symptoms associated with tissue ischemia, including, but not limited to, impaired, or loss of, organ function (including without limitation impairments or loss of brain, kidney, or heart function), cramping, claudication, numbness, tingling, weakness, pain, reduced wound healing, inflammation, skin discoloration, and gangrene.

In one embodiment, the subject exhibits at least one symptom of an ischemic tissue or tissue damaged by ischemia. In particular embodiments, the subject is a human who is has or who is at risk of having an ischemic tissue or tissue damaged by ischemia, e.g., a subject that has diabetes, peripheral vascular disease, thromboangiitis obliterans, vasculitis, cardiovascular disease, coronary artery disease or heart failure, or cerebrovascular disease, cardiovascular disease, or cerebrovascular disease.

Illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia suitable for treatment or amelioration using the methods of the present invention, include, ischemia resulting from surgery, chemotherapy, radiation therapy, or cell, tissue, or organ transplant or graft.

In various embodiments, the methods are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In various embodiments, the preparations or therapeutic cell compositions disclosed herein can be used to treat an ischemic tissue in which it is desirable to increase the blood flow, oxygen supply, glucose supply, or supply of nutrients to the tissue.

In some embodiments, the 15-PGDH inhibitor can be administered to a preparation of tissue stem cells, such as neural stem stems, mesenchymal stem cells, or stem cells that can generate other tissues, and/or a preparation of pluripotent stem cells.

In other embodiments, the 15-PGDH inhibitor can be administered to a bone marrow graft donor or a hematopoietic stem cell donor to increase the fitness of a donor bone marrow graft or a donor hematopoietic stem cell graft.

In other embodiments, the 15-PGDH inhibitor can also be administered to bone marrow of a subject to increase stem cells in the subject or to increase the fitness of the marrow as a donor graft.

In yet other embodiments, the 15-PGDH inhibitor can be administered to a subject to mitigate bone marrow graft rejection, to enhance bone marrow graft engraftment, to enhance engraftment of a hematopoietic stem cell graft, or an umbilical cord blood stem cell graft, to enhance engraftment of a hematopoietic stem cell graft, or an umbilical cord stem cell graft, and/or to decrease the number of units of umbilical cord blood required for transplantation into the subject. The administration can be, for example, following treatment of the subject or the marrow of the subject with radiation therapy, chemotherapy, or immunosuppressive therapy.

In other embodiments, the 15-PGDH inhibitor can be administered to a recipient of a bone marrow transplant, of a hematopoietic stem cell transplant, or of an umbilical cord blood stem cell transplant, in order to decrease the administration of other treatments or growth factors.

In some embodiments, the 15-PGDH inhibitor can be administered to a subject to enhance recovery of neutrophils following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, neutropenias from other bone marrow diseases, drug induced neutropenia, immune neutropenias, idiopathic neutropenia, and following infections with viruses that include, but are not limited to, HIV, CMV, and parvovirus.

In other embodiments, the 15-PGDH inhibitor can be administered to a subject to enhance recovery of platelets following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, thrombocytopenias from other bone marrow diseases, drug induced thrombocytopenia, immune thrombocytopenia, idiopathic thrombocytopenic purpura, idiopathic thrombocytopenia, and following infections with viruses that include, but are not limited to, HIV, CMV, and parvovirus.

In still other embodiments, the 15-PGDH inhibitor can be administered to a subject to enhance recovery of hemoglobin following bone marrow transplantation, following umbilical cord blood transplantation, following transplantation with hematopoietic stem cells, following conventional chemotherapy, following radiation treatment, and in individuals with anemias from diseases that include but are not limited to aplastic anemia, myelodysplasia, myelofibrosis, anemia from other bone marrow diseases, drug induced anemia, immune mediated anemias, anemia of chronic disease, idiopathic anemia, and following infections with viruses that include, but are not limited to, HIV, CMV, and parvovirus.

In some embodiments, the 15-PGDH inhibitor can be administered to a subject to enhance numbers of bone marrow stem cell numbers following bone marrow transplantation, following umbilical cord blood transplantation, following transplantation with hematopoietic stem cells, following conventional chemotherapy, following radiation treatment, in individuals with other bone marrow diseases, in individuals with cytopenias following viral infections, and in individuals with cytopenias.

In other embodiments, the 15-PGDH inhibitor can be administered to a subject to enhance response to cytokines and/or cell mobilization agents administered to individuals with cytopenias that include but are not limited to neutropenia, thrombocytopenia, lymphocytopenia, and anemia. Cytokines whose responses may be enhanced by 15-PGDH inhibitors include, but are not limited to: G-CSF, GM-CSF, EPO, IL-3, IL-6, TPO, SCF, and TPO-RA (thrombopoietin receptor agonist).

In further embodiments, the 15-PGDH inhibitor can be administered to a subject or to a tissue graft of a subject to mitigate graft rejection, to enhance graft engraftment, to enhance graft engraftment following treatment of the subject or the marrow of the subject with radiation therapy, chemotherapy, or immunosuppressive therapy, to confer resistance to toxic or lethal effects of exposure to radiation, confer resistance to the toxic effect of Cytoxan, the toxic effect of fludarabine, the toxic effect of chemotherapy, or the toxic effect of immunosuppressive therapy, to decrease infection, and/or to decrease pulmonary toxicity from radiation.

In other embodiments, the 15-PGDH inhibitor can be administered to a recipient of a tissue stem cell transplant, including but not limited to a transplant with hematopoietic stem cells, neural stem stems, mesenchymal stem cells, or stem cells for other tissues, so as to accelerate tissue regeneration and repair following the transplant.

In some embodiments, the administration of a 15-PGDH inhibitor alone or in combination with a cytokine, hematopoietic cytokine, and/or cell mobilization agent to a subject in need thereof, cells of the subject, and/or tissue of the subject can be used for the purpose of increasing neutrophils in the subject. For example, the hematopoietic cytokine or cell mobilization agent can include at least one of G-CSF or Plerixafor.

In other embodiments, the administration of a 15-PGDH inhibitor alone or in combination with a cytokine, hematopoietic cytokine, and/or cell mobilization agent to a subject in need thereof, cells of the subject, and/or tissue of the subject can be used for the purpose of increasing numbers of and/or of mobilizing peripheral blood hematopoietic stem cells in the subject. For example, the hematopoietic cytokine or cell mobilization agent can include at least one of G-CSF or Plerixafor.

In still other embodiments, the administration of a 15-PGDH inhibitor alone or in combination with a cytokine, hematopoietic cytokine, and/or cell mobilization agent to a subject in need thereof, cells of the subject, and/or tissue of the subject can be used for the purpose of increasing numbers of hematopoietic stem cells in blood or bone marrow of the subject. For example, the hematopoietic cytokine or cell mobilization agent can include at least one of G-CSF or Plerixafor.

15-PGDH inhibitors can be identified using assays in which putative inhibitor compounds are applied to cells expressing 15-PGDH and then the functional effects on 15-PGDH activity are determined. Samples or assays comprising 15-PGDH that are treated with a potential inhibitor are compared to control samples without the inhibitor to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%.

Agents tested as inhibitors of SCD (e.g., 15-PGDH) can be any small chemical molecule or compound. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays).

In some embodiments, the 15-PGDH inhibitor can include a compound having the following formula (I):

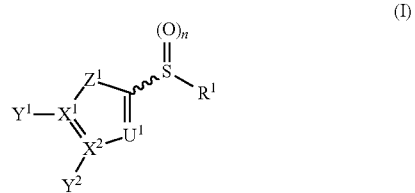

(I)

wherein n is 0-2;

$Y^1$, $Y^2$, and $R^1$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH2, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $Y^1$ and $Y^2$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—R$^2$, or C—NR$^3$R$^4$, wherein R$^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein R$^1$ and R$^2$ may be linked to form a cyclic or polycyclic ring, wherein R$^3$ and R$^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and R$^3$ or R$^4$ may be absent;

$X^1$ and $X^2$ are independently N or C, and wherein when $X^1$ and/or $X^2$ are N, $Y^1$ and/or $Y^2$, respectively, are absent;

$Z^1$ is O, S, CR$^a$R$^b$ or NR$^a$, wherein R$^a$ and R$^b$ are independently H or a $C_{1-8}$ alkyl, which is linear, branched, or cyclic, and which is unsubstituted or substituted;

and pharmaceutically acceptable salts thereof.

Examples of 15-PGDH inhibitors having formulas (I) include the following compounds:

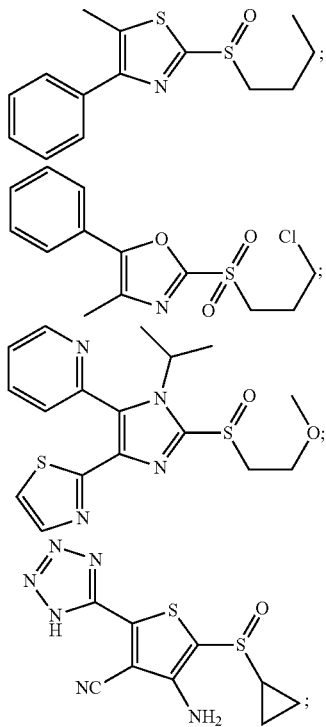

and pharmaceutically acceptable salts thereof.

In other embodiments, the 15-PGDH inhibitor can include a compound having the following formula (II):

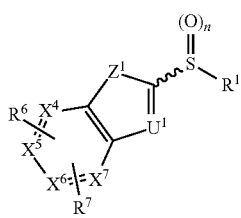

wherein n is 0-2

$X^4$, $X^5$, $X^6$, and $X^7$ are independently N or $CR^c$;

$R^1$, $R^6$, $R^7$, and $R^c$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH2, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

$Z^1$ is O, S, $CR^aR^b$ or $NR^a$, wherein $R^a$ and $R^b$ are independently H or a $C_{1-8}$ alkyl, which is linear, branched, or cyclic, and which is unsubstituted or substituted;

and pharmaceutically acceptable salts thereof.

Examples of 15-PGDH inhibitors having formulas (II) include the following compounds:

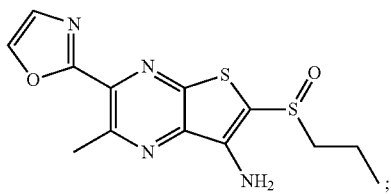

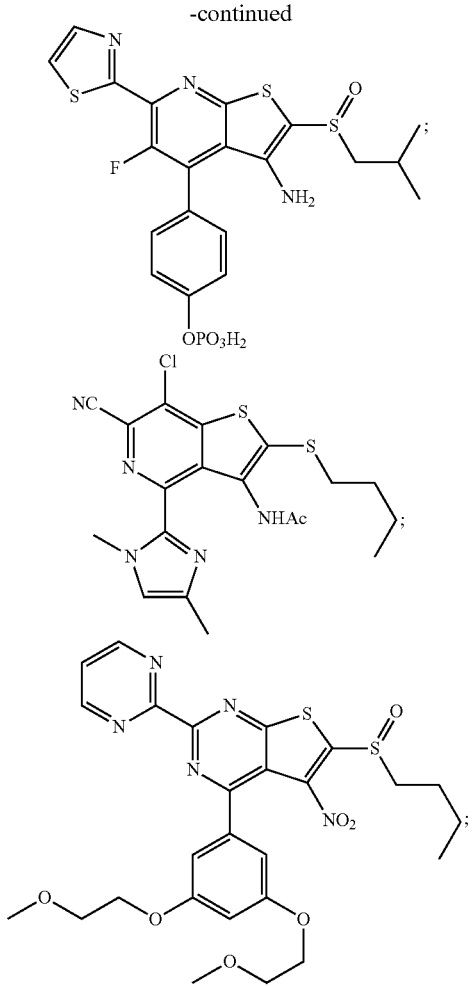

and pharmaceutically acceptable salts thereof.

In yet other embodiments, the 15-PGDH inhibitor can include a compound having the following formula (III) or (IV):

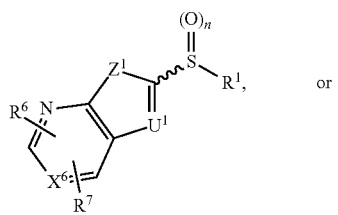 (III)

or

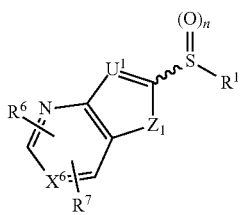 (IV)

wherein n is 0-2

$X^6$ is independently is N or $CR^c$;

$R^1$, $R^6$, $R^7$, and $R^c$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH2, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—NR$^3$R$^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

$Z^1$ is O, S, CR$^a$R$^b$ or NR$^a$, wherein $R^a$ and $R^b$ are independently H or a $C_{1-8}$ alkyl, which is linear, branched, or cyclic, and which is unsubstituted or substituted;

and pharmaceutically acceptable salts thereof.

In some embodiments, $R^1$ is selected from the group consisting of branched or linear alkyl including —(CH$_2$)$_{n1}$CH$_3$ ($n_1$=0-7),

wherein $n_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,
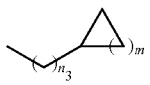
($n_3$=0-5, m=1-5), and
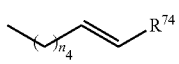
($n_4$=0-5).
In other embodiments, $R^6$ and $R^7$ can each independently be one of the following:
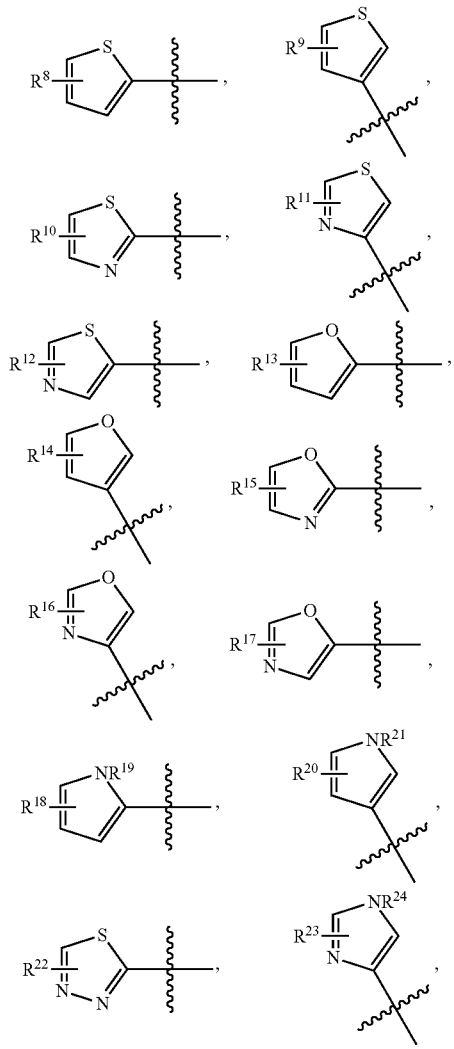
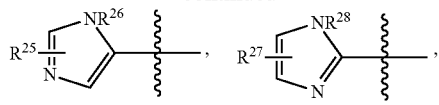
-continued
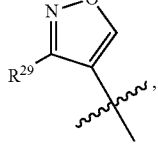 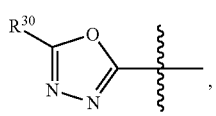
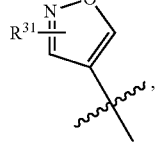 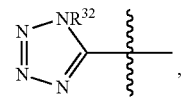
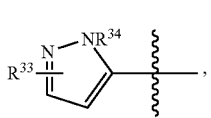 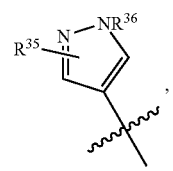
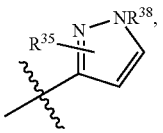 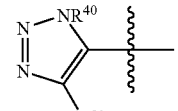
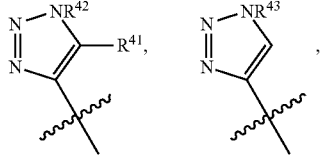
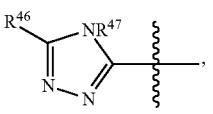 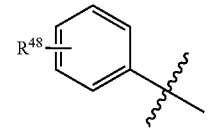
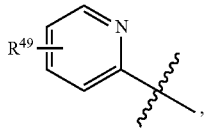 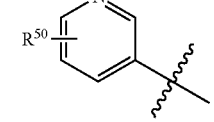
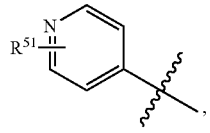 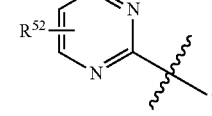
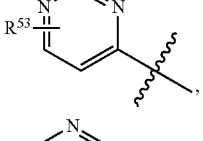 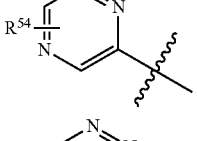
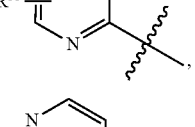 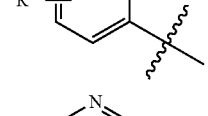
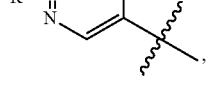 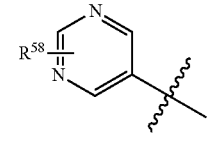

-continued

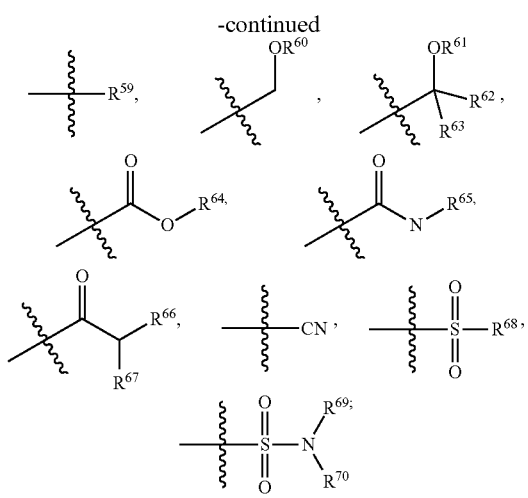

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In still other embodiments, $R^6$ and $R^7$ can independently be a group that improves aqueous solubility, for example, a phosphate ester (—OPO$_3$H$_2$), a phenyl ring linked to a phosphate ester (—OPO$_3$H$_2$), a phenyl ring substituted with one or more methoxyethoxy groups, or a morpholine, or an aryl or heteroaryl ring substituted with such a group.

Examples of 15-PGDH inhibitors having formulas (III) or (IV) include the following compounds:

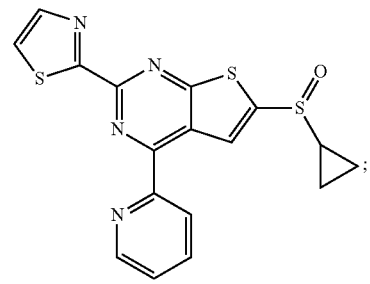

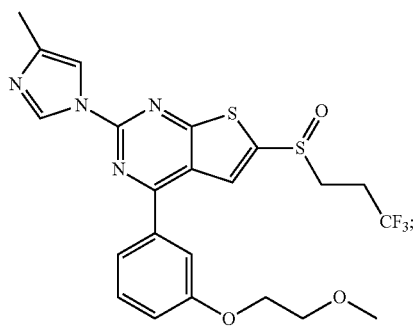

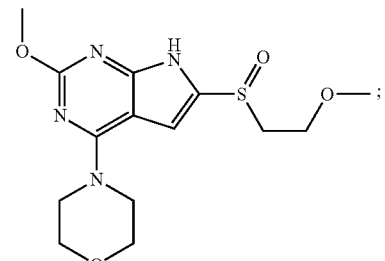

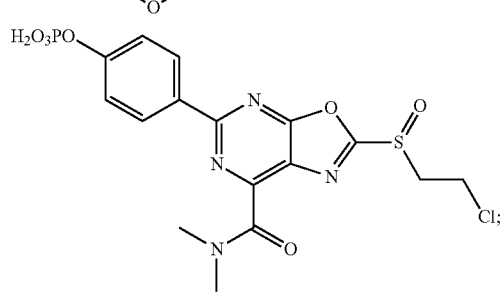

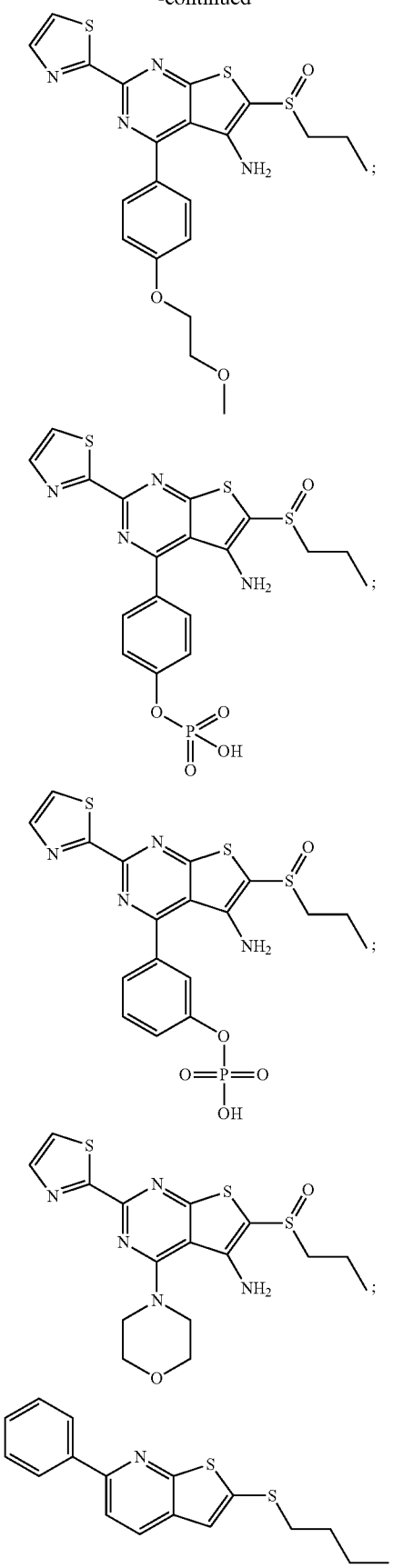
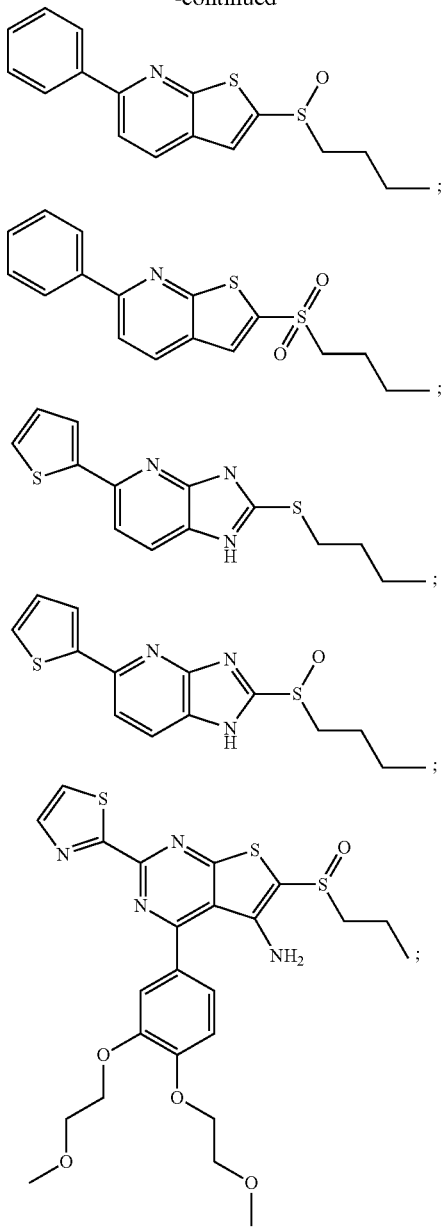
and pharmaceutically acceptable salts thereof.
In other embodiments, the 15-PGDH inhibitor can include a compound having the following formula (V):
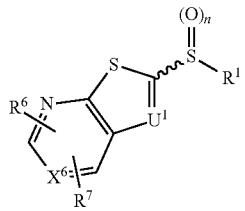
(V)
wherein n is 0-2
$X^6$ is independently is N or $CR^c$ $R^1$, $R^6$, $R^7$, and $R^c$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH2, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—NR$^3$R$^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

and pharmaceutically acceptable salts thereof.

In some embodiments, $R^1$ is selected from the group consisting of branched or linear alkyl including —(CH$_2$)n$_1$CH$_3$ (n$_1$=0-7),

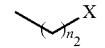

wherein n$_2$=0-6 and X is any of the following: CF$_y$H$_z$ (y+z=3), CCl$_y$H$_z$ (y+z=3), OH, OAc, OMe, $R^{71}$, OR$^{72}$, CN, N(R$^{73}$)$_2$,

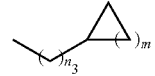

(n$_3$=0-5, m=1-5), and

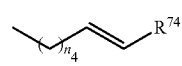

(n$_4$=0-5).

In other embodiments, $R^6$ and $R^7$ can each independently be one of the following:

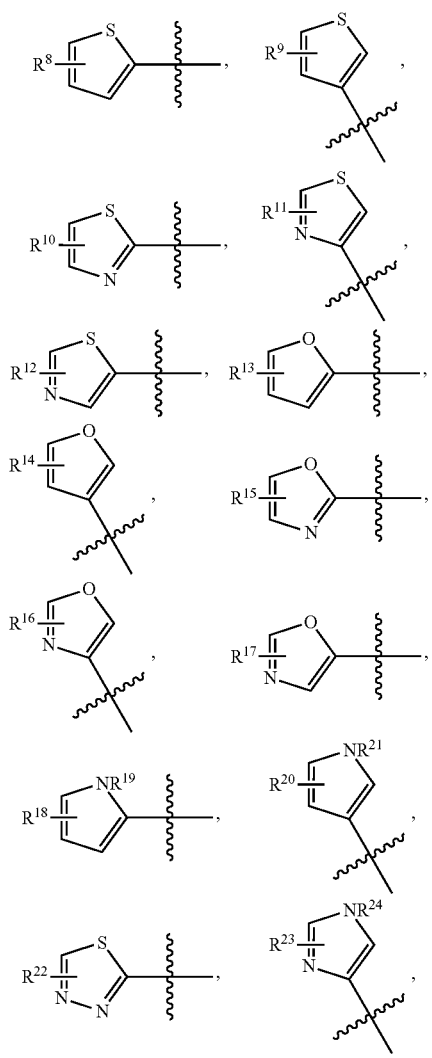

-continued

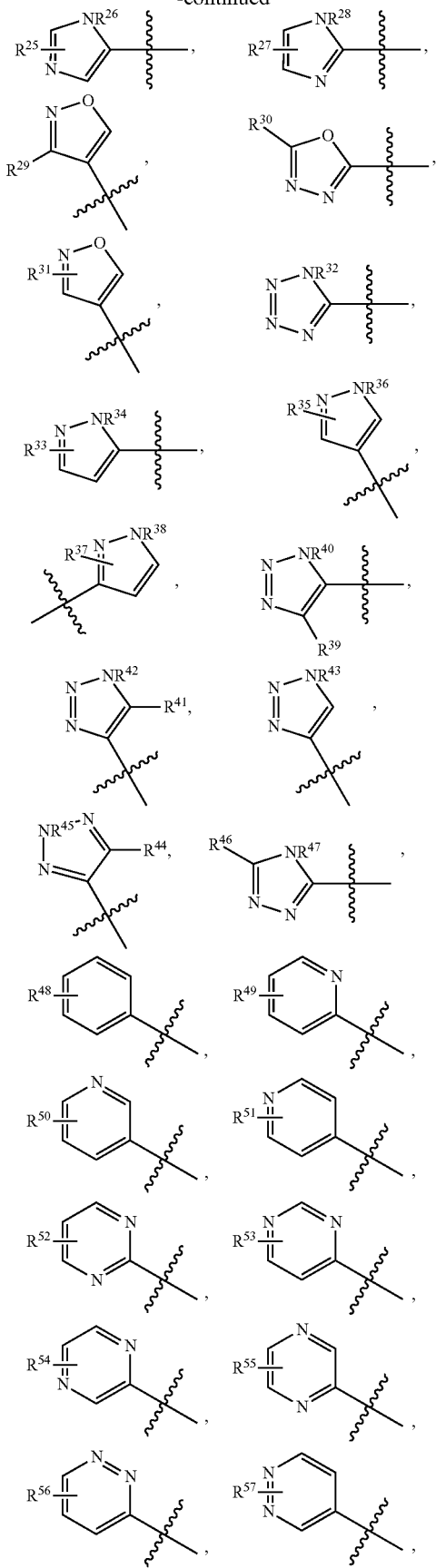

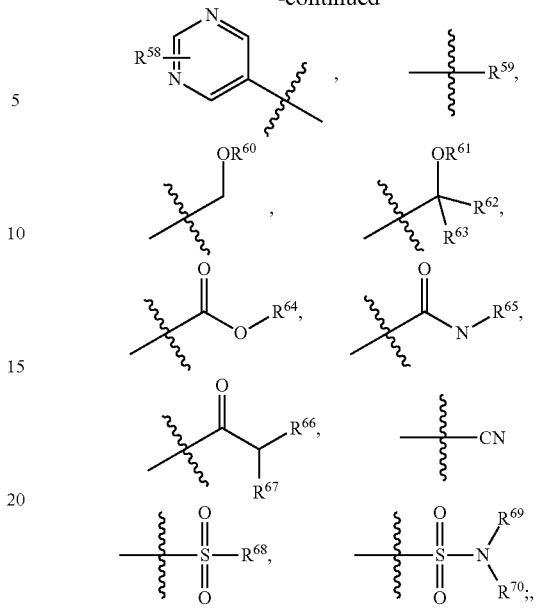

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In still other embodiments, $R^6$ and $R^7$ can independently be a group that improves aqueous solubility, for example, a phosphate ester (—OPO$_3$H$_2$), a phenyl ring linked to a phosphate ester (—OPO$_3$H$_2$), a phenyl ring substituted with one or more methoxyethoxy groups, or a morpholine, or an aryl or heteroaryl ring substituted with such a group.

In other embodiments, the 15-PGDH inhibitor can include a compound having the following formula (VI):

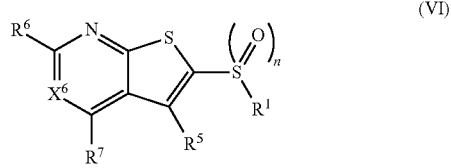

(VI)

wherein n=0-2;
$X^6$ is N or $CR^e$;
$R^1$ is selected from the group consisting of branched or linear alkyl including —(CH$_2$)n$_1$CH$_3$ (n$_1$=0-7),

wherein n$_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

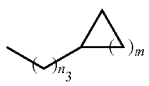

(n$_3$=0-5, m=1-5), and

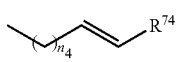

(n$_4$=0-5).
$R^5$ is selected from the group consisting of H, Cl, F, NH$_2$, and $N(R^{76})_2$;
$R^6$ and $R^7$ can each independently be one of the following:

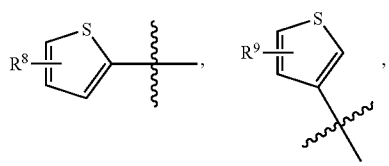

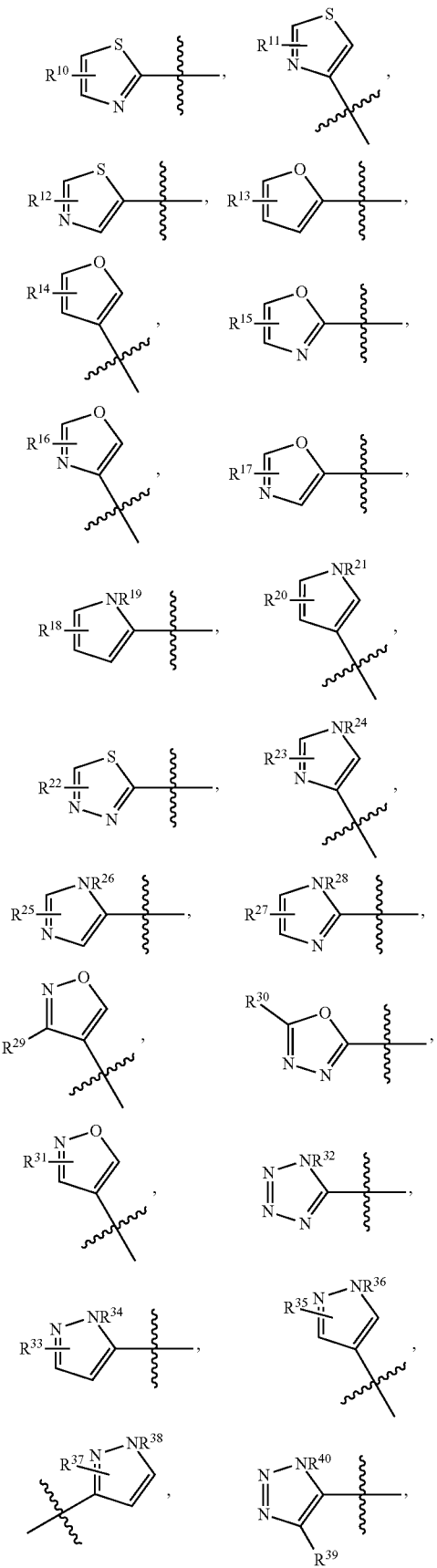

-continued

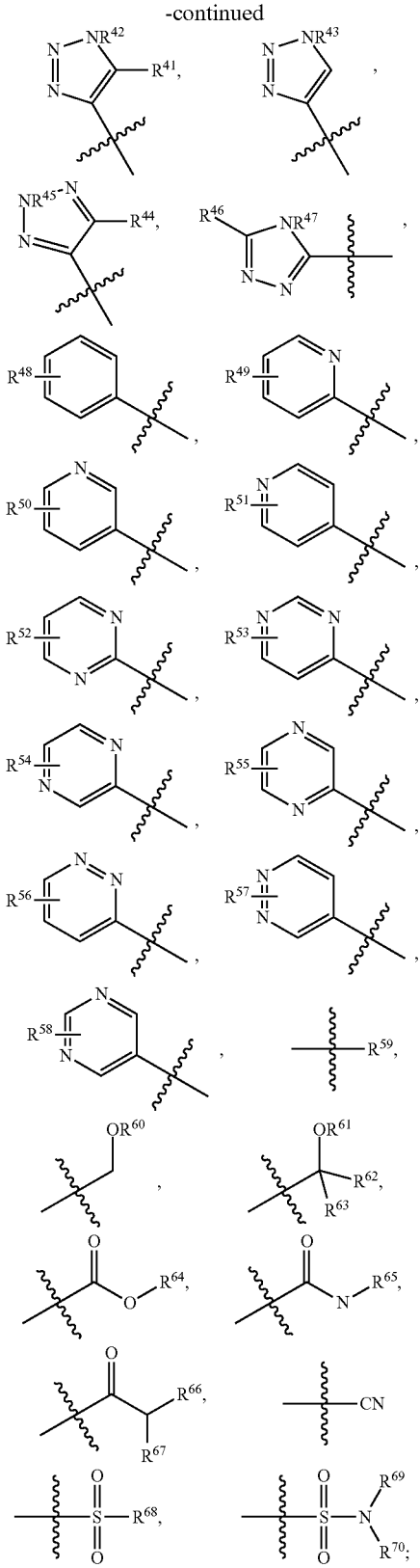

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{76}$, and $R^c$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkylcarbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In other embodiments, the 15-PGDH inhibitor can include a compound having the following formula (VII):

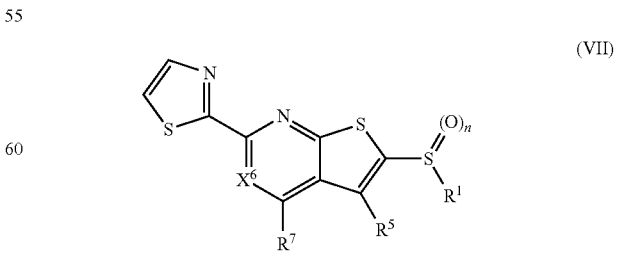

(VII)

wherein n=0-2;
$X^6$ is N or CR$^c$;

$R^1$ is selected from the group consisting of branched or linear alkyl including —(CH$_2$)n$_1$CH$_3$ (n$_1$=0-7),
wherein n$_2$=0-6 and X is any of the following: CF$_y$H$_z$ (y+z=3), CCl$_y$H$_z$ (y+z=3), OH, OAc, OMe, R$^{71}$, OR$^{72}$, CN, N(R$^{73}$)$_2$,
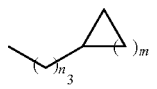
(n$_3$=0-5, m=1-5), and
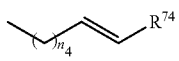
(n$_4$=0-5).
$R^5$ is selected from the group consisting of H, Cl, F, NH$_2$, and N(R$^{76}$)$_2$;
$R^7$ can each independently be one of the following:
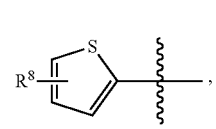, 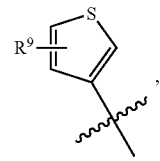,
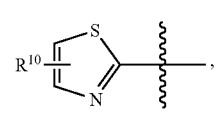, 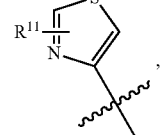,
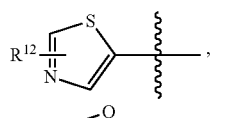, 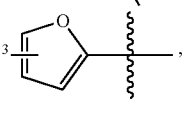,
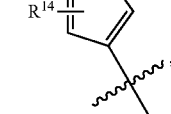, 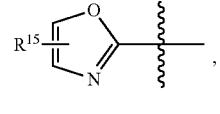,
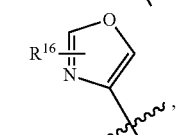, 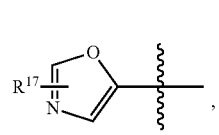,
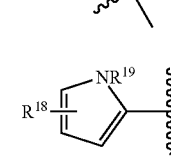, 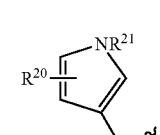,
-continued
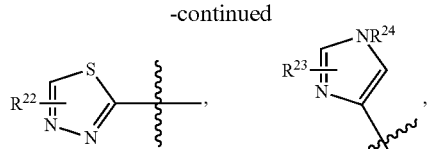,
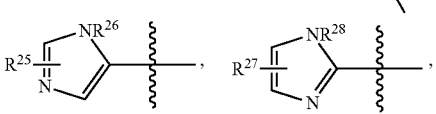,
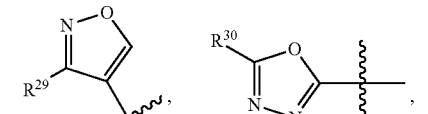,
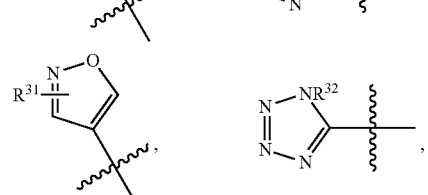,
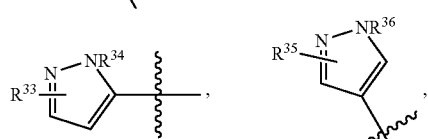,
,
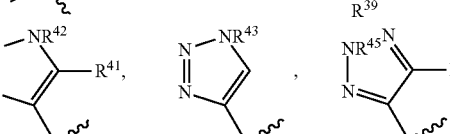,
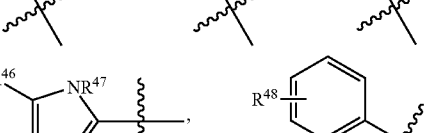,
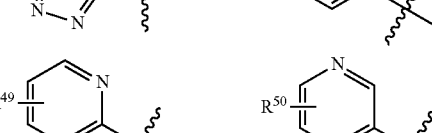,
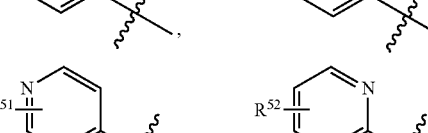,
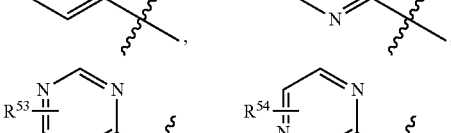,
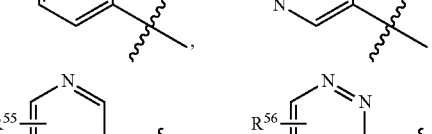,
, -continued

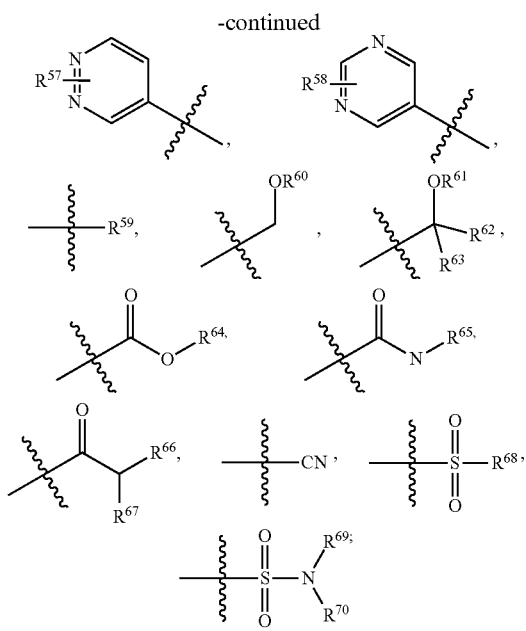

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{76}$, and $R^c$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkylcarbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

Examples of compounds having formulas (V), (VI), or (VII) are selected from the group consisting of:

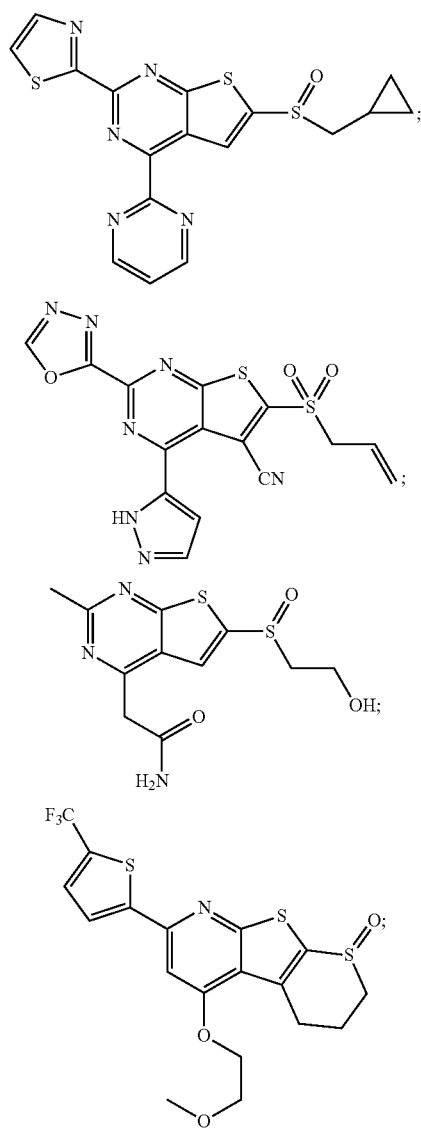

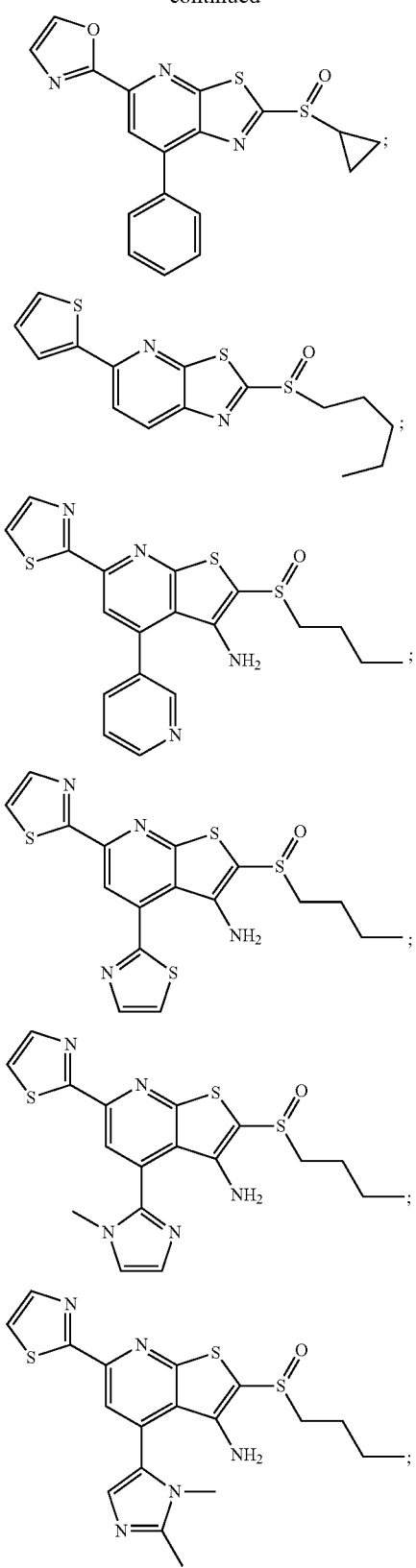
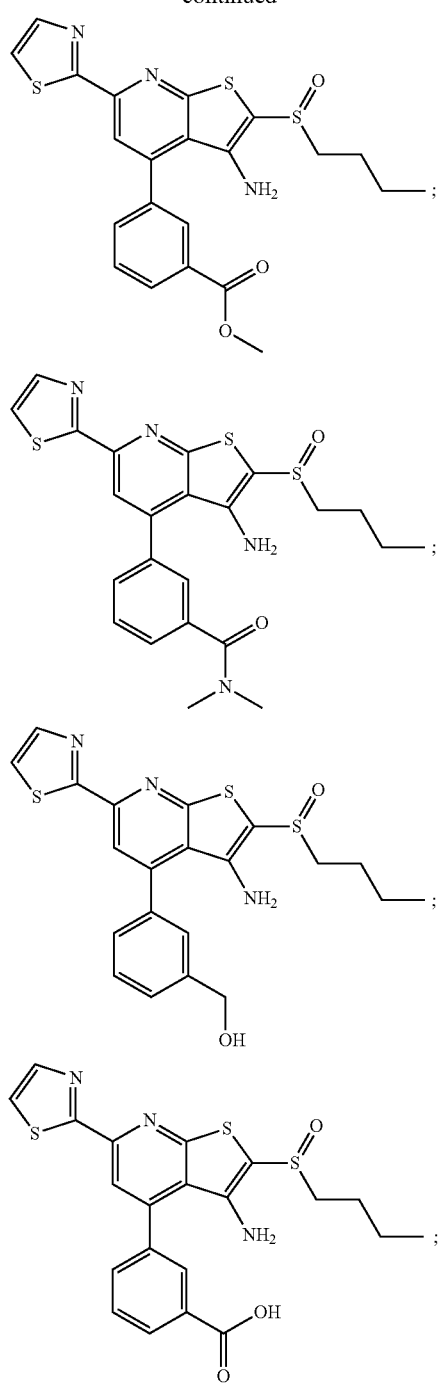

57
-continued
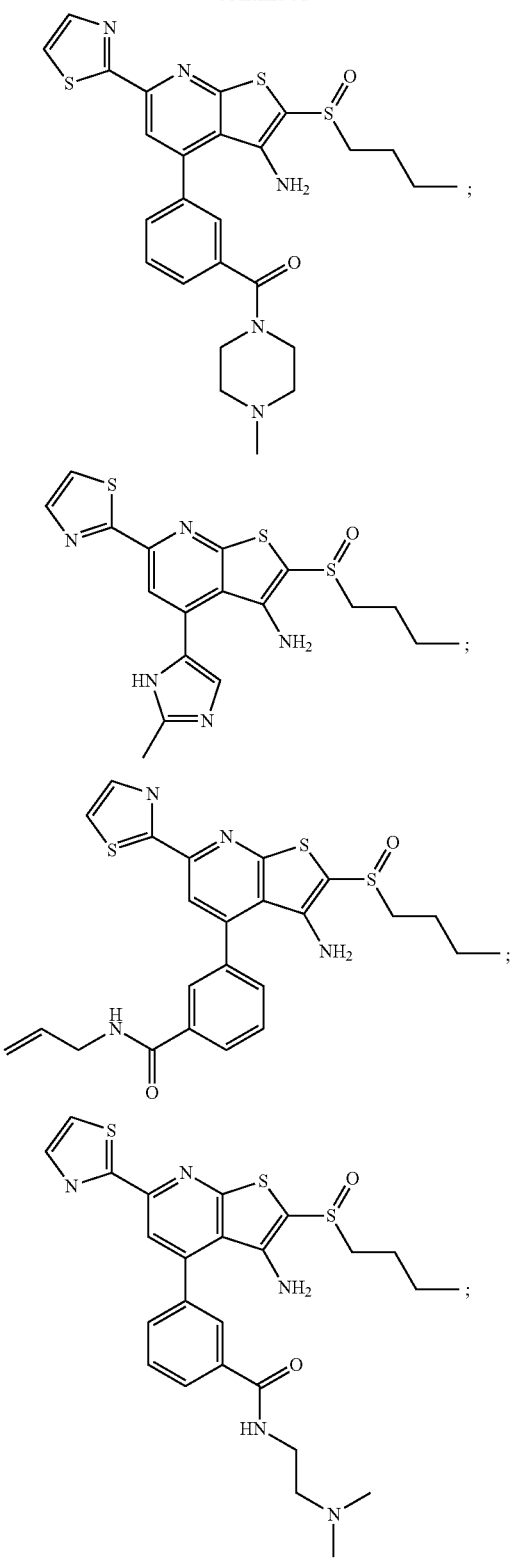
58
-continued
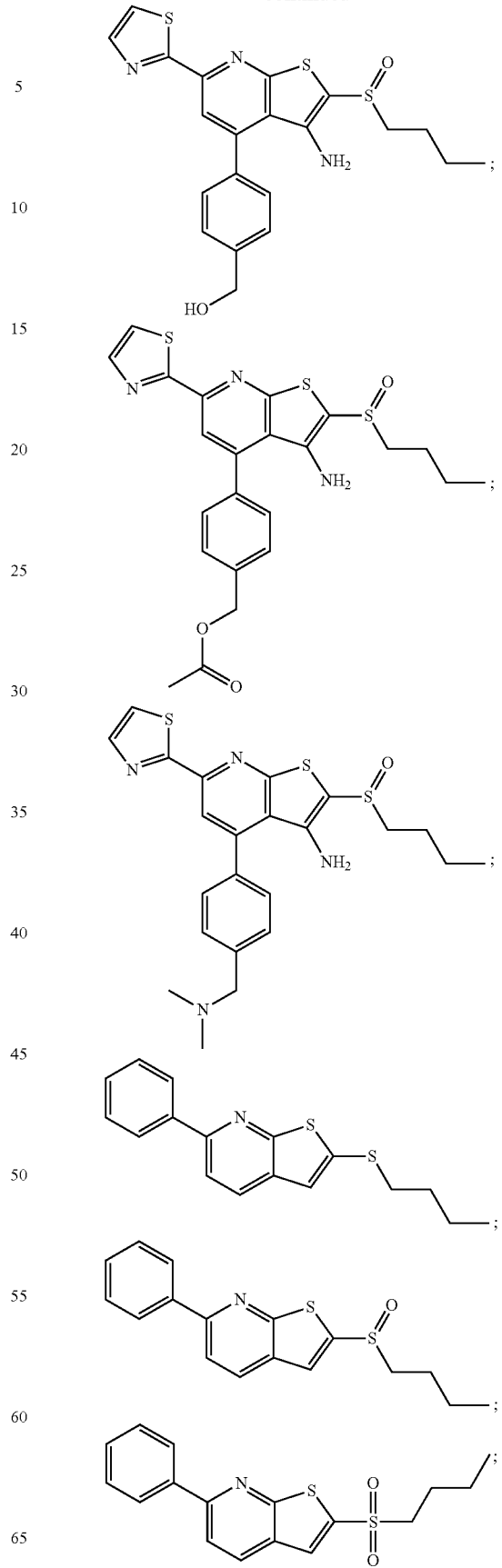

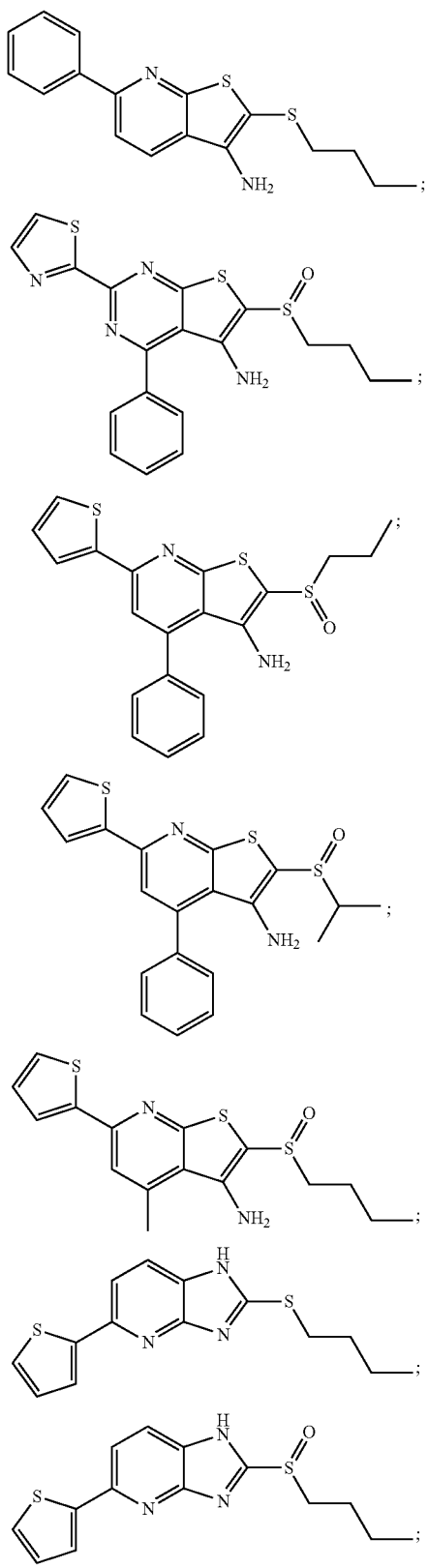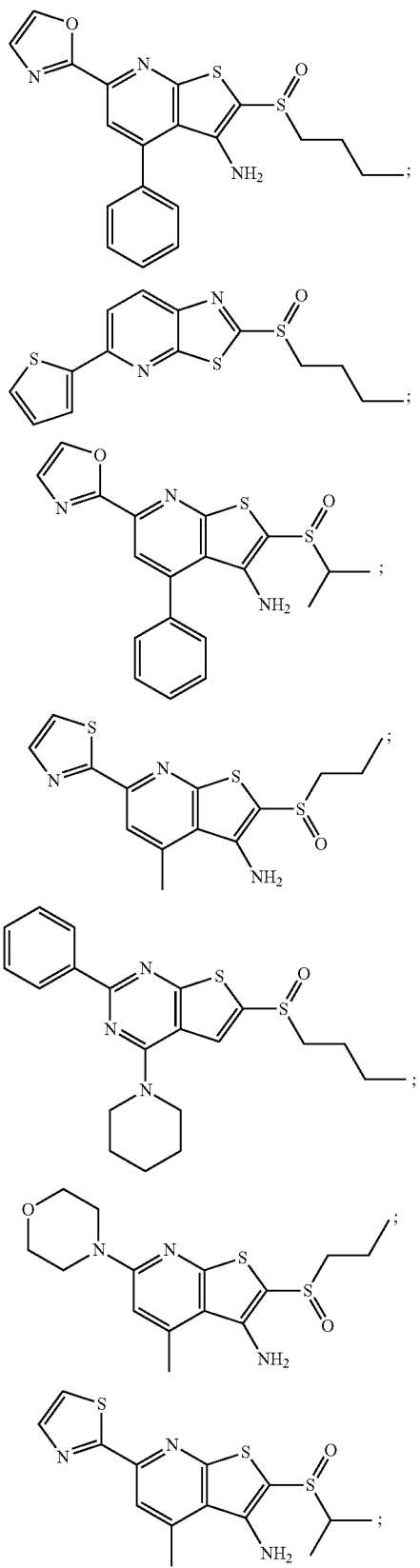

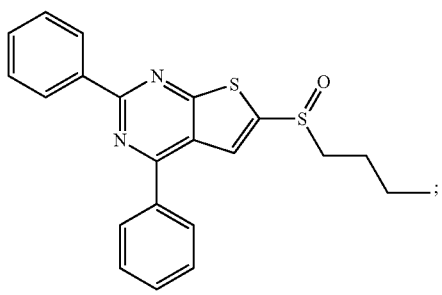
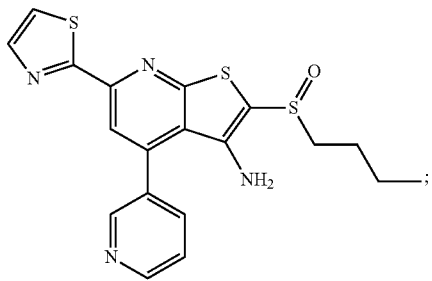
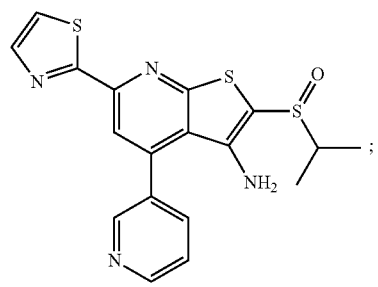
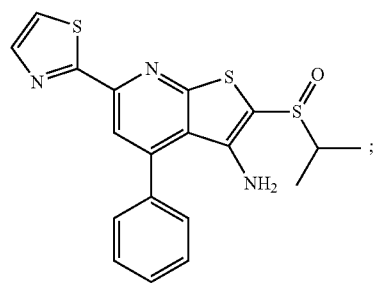
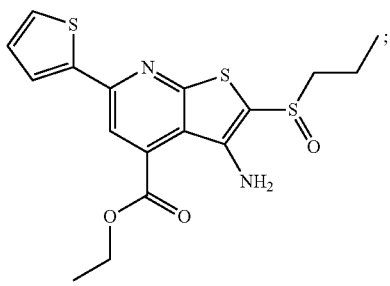
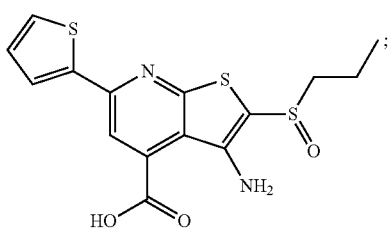
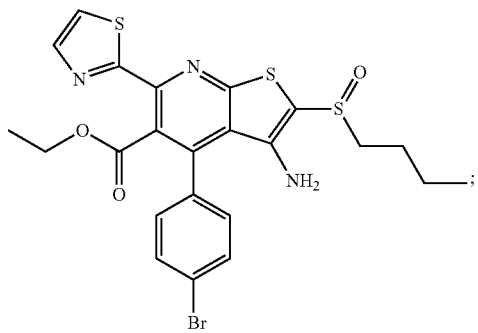
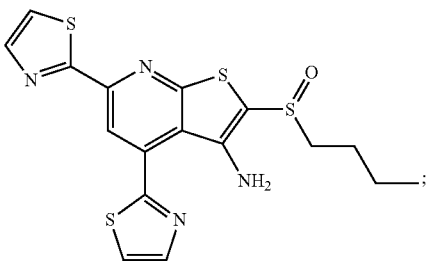
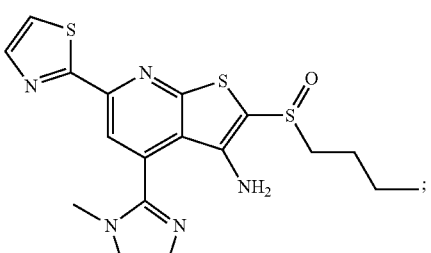
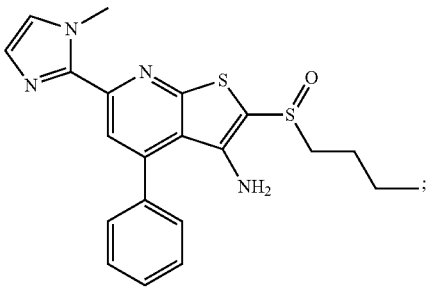
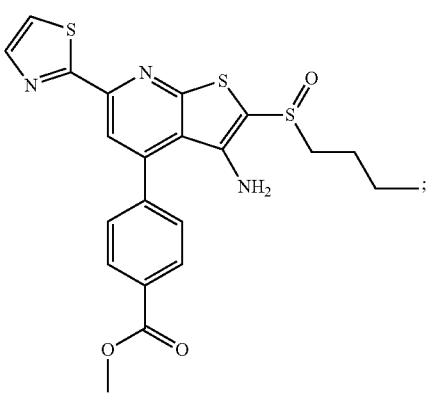

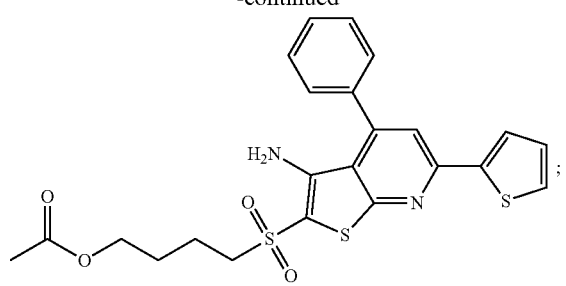
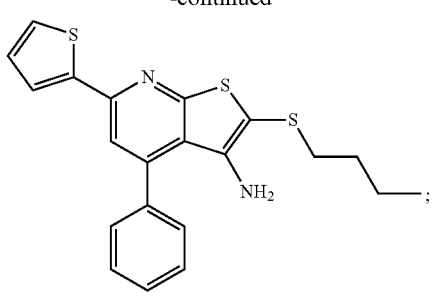
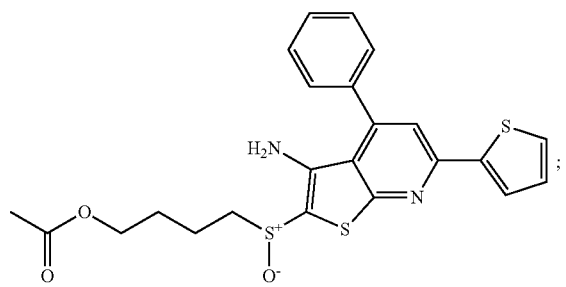
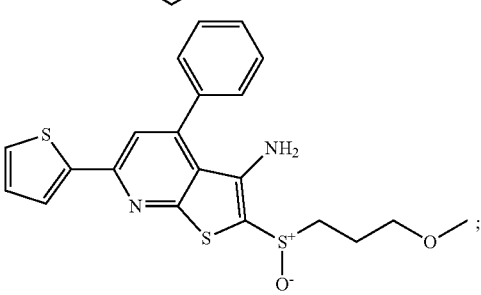
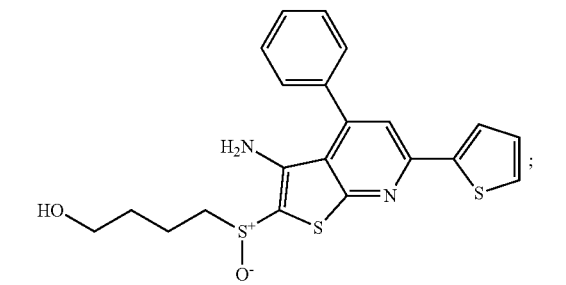
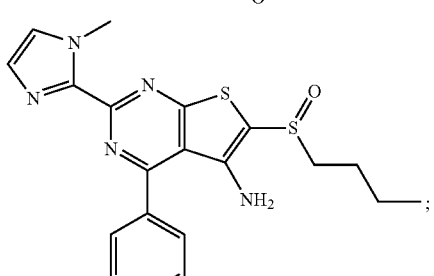
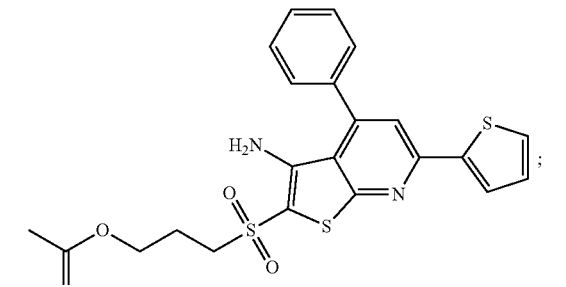
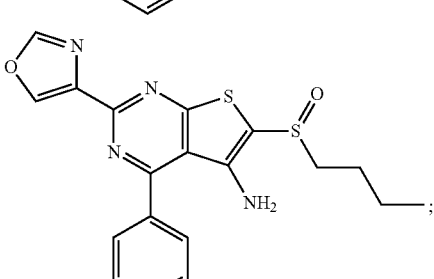
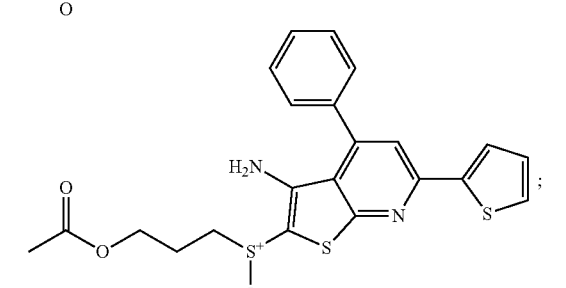
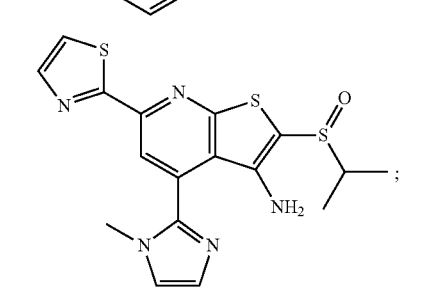
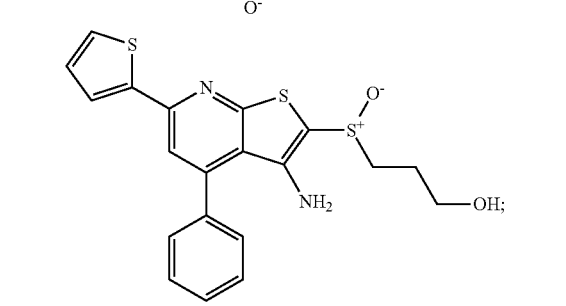
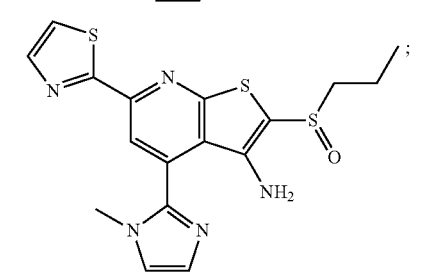

65
-continued
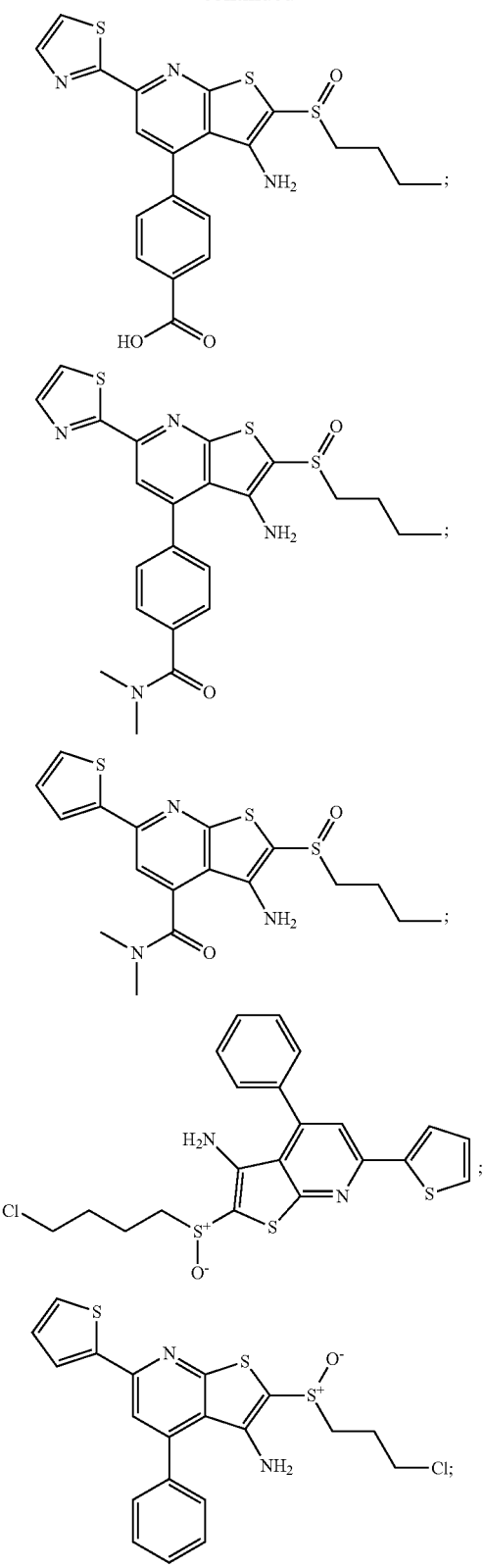
66
-continued
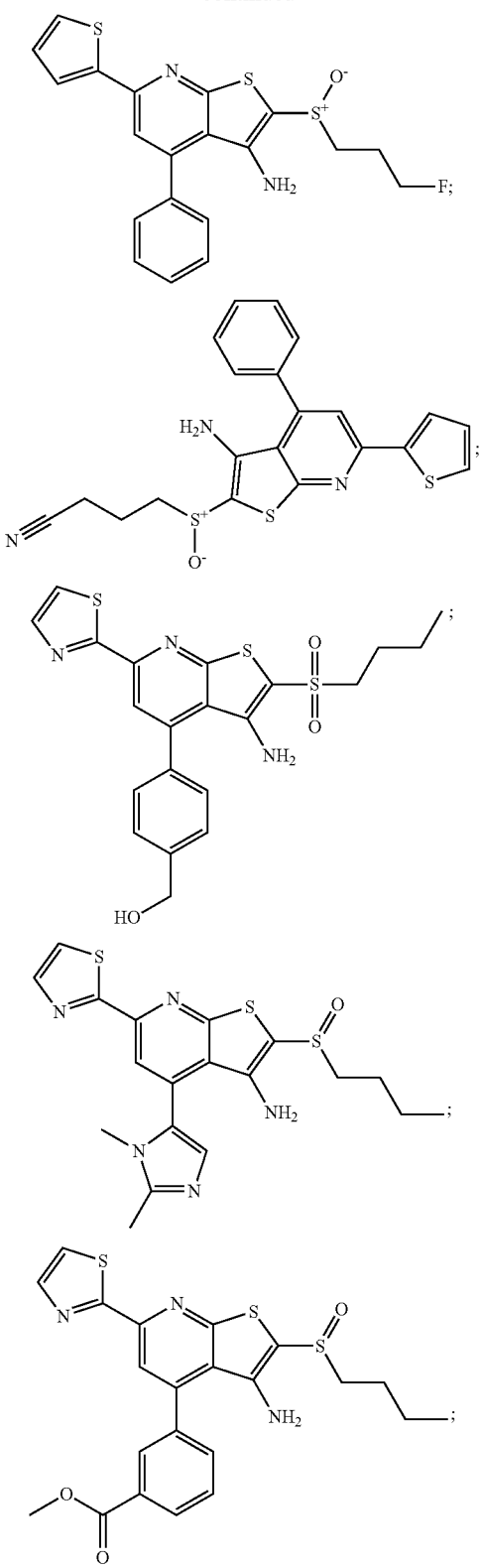

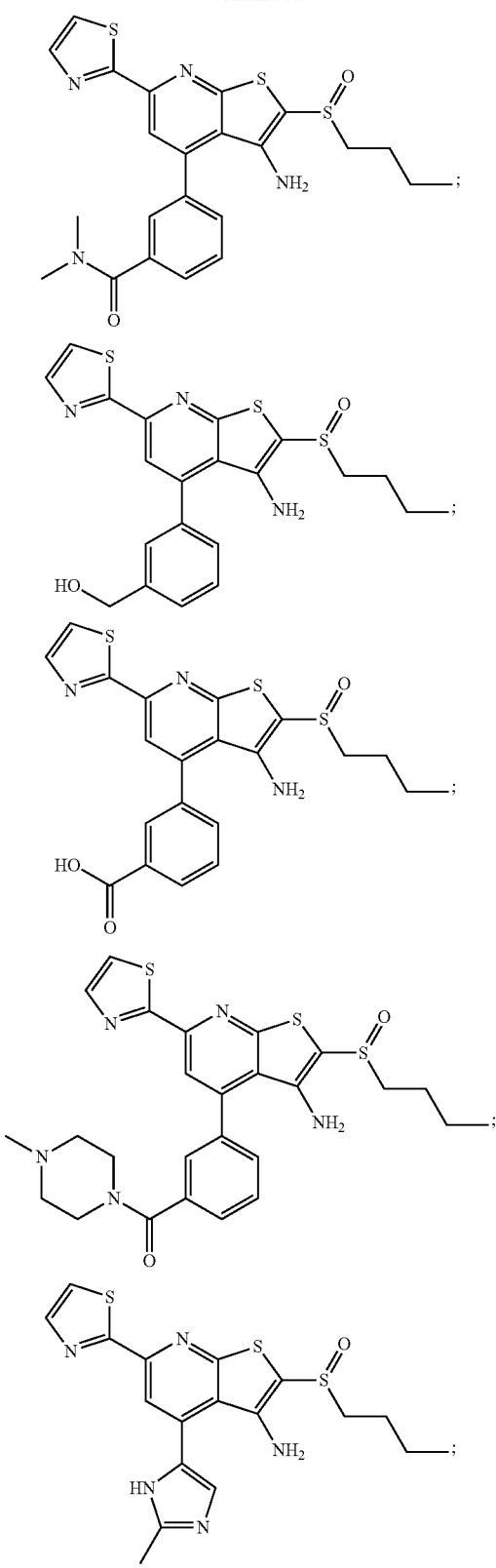
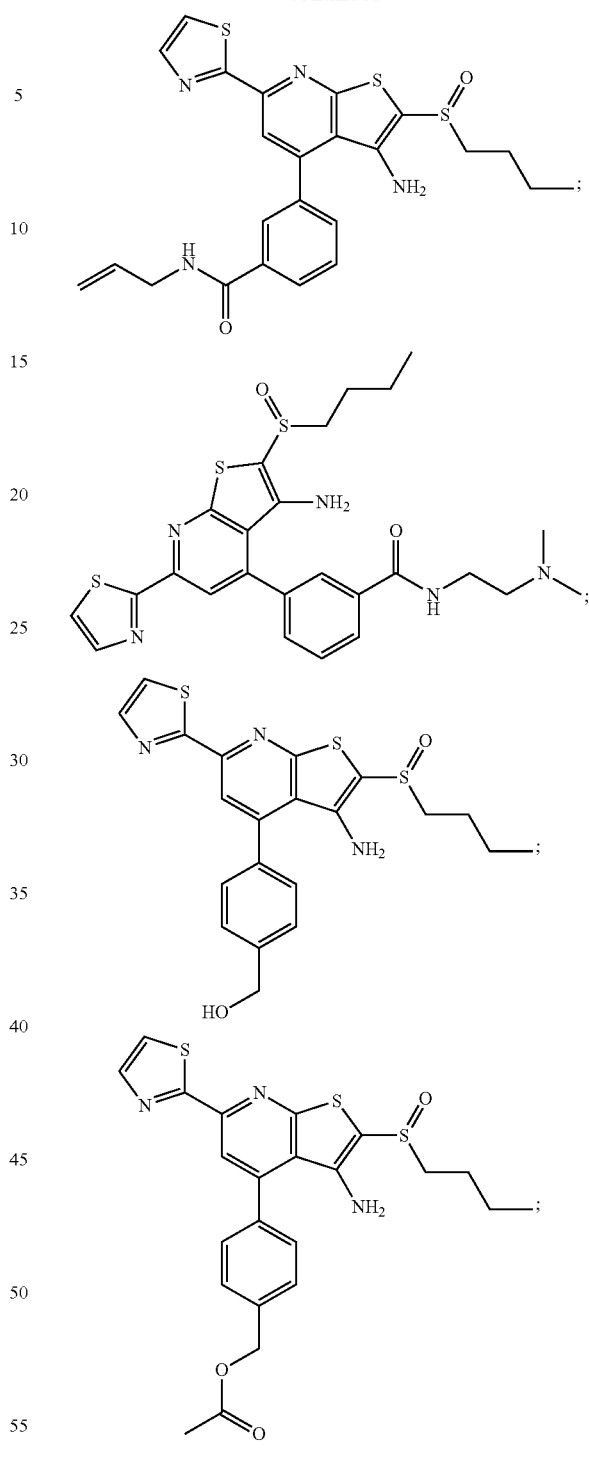

69
-continued
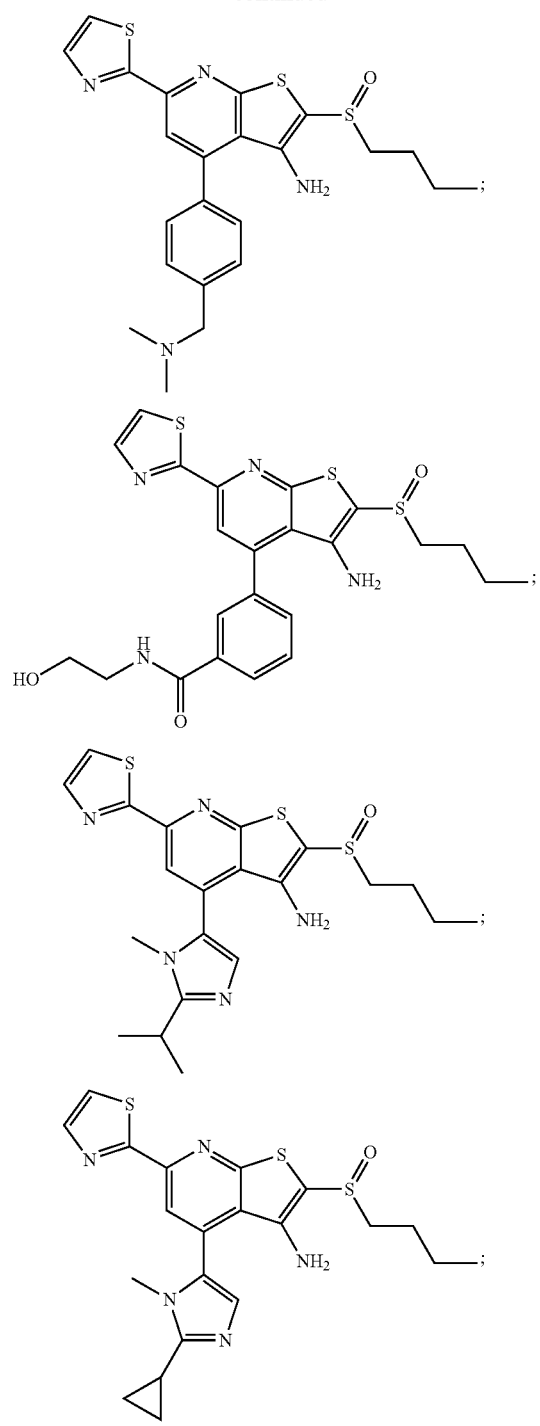
70
-continued
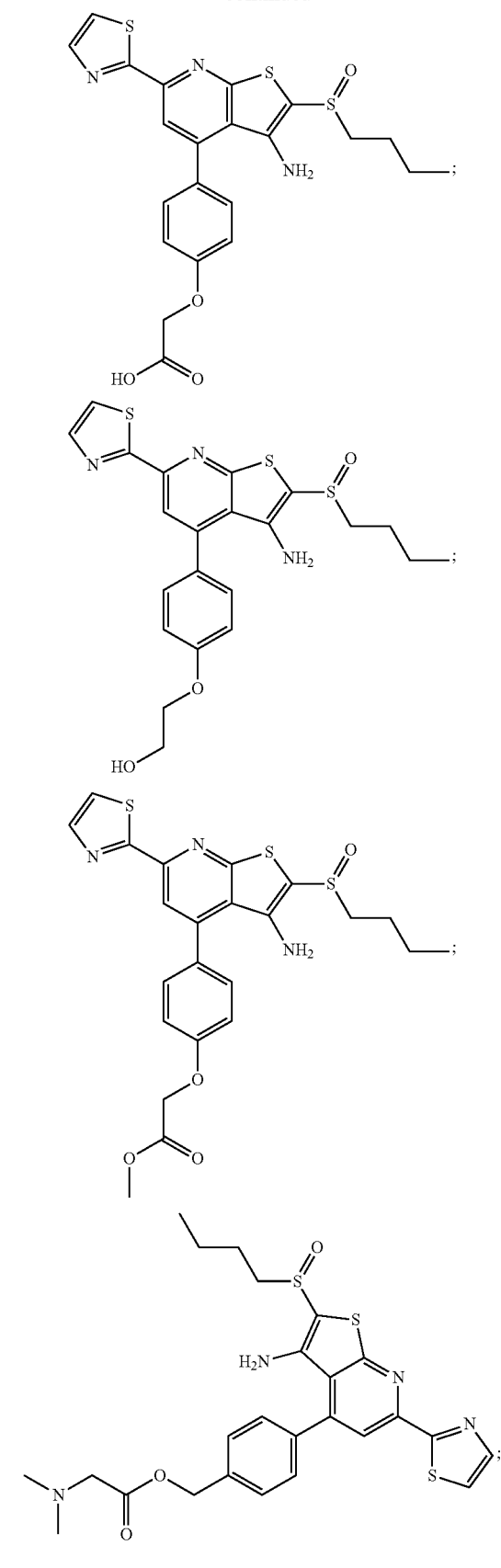

-continued
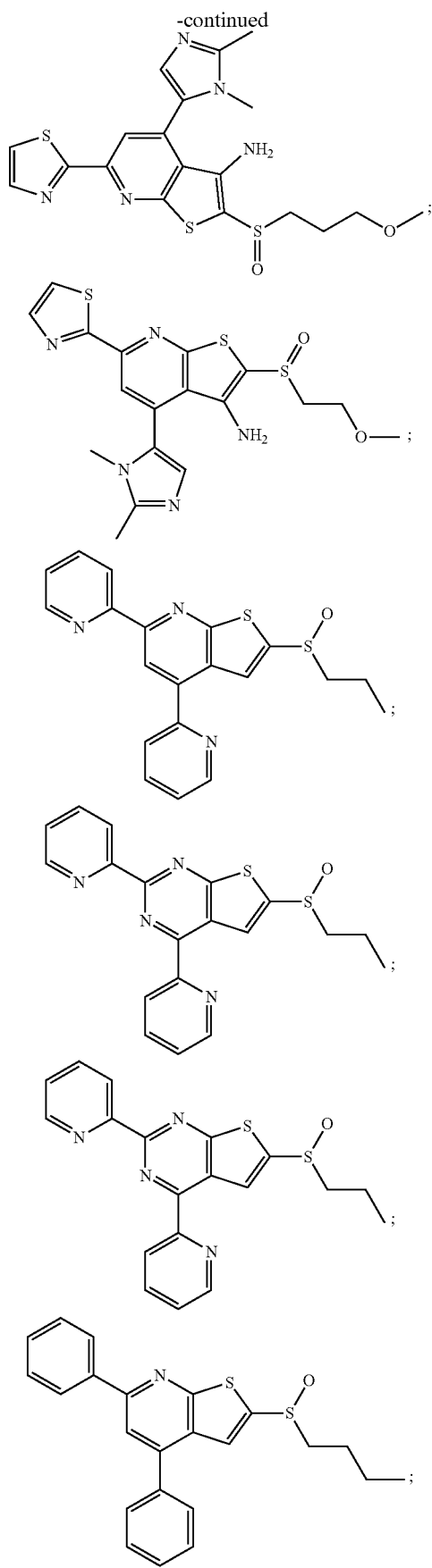
-continued
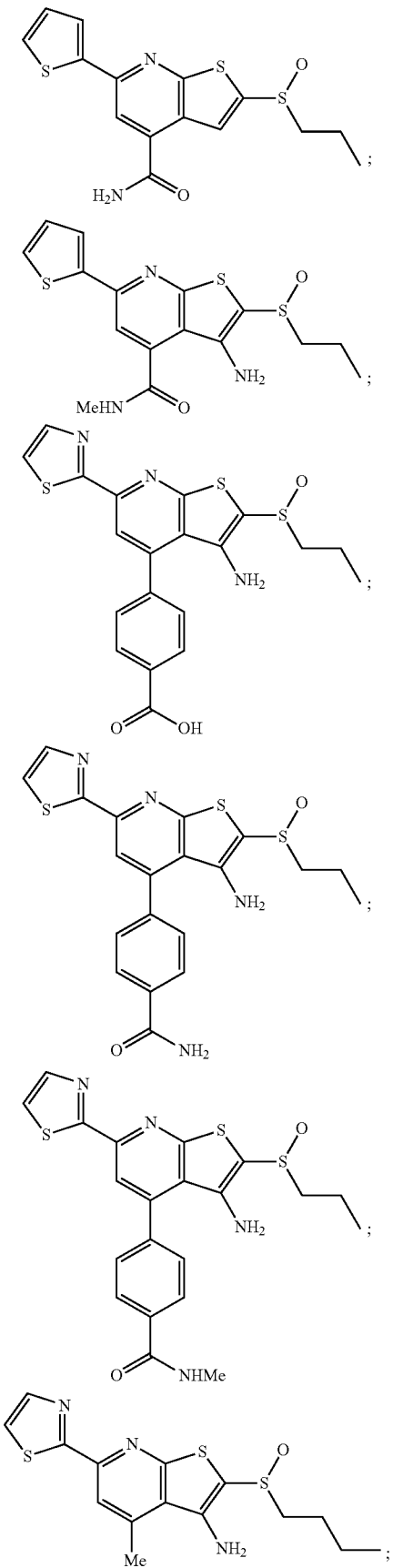

-continued
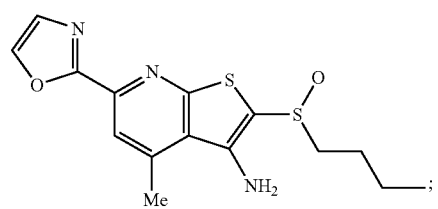
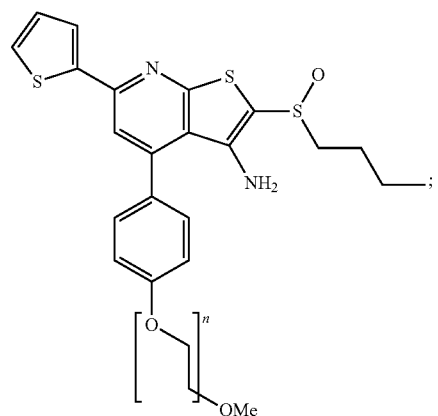
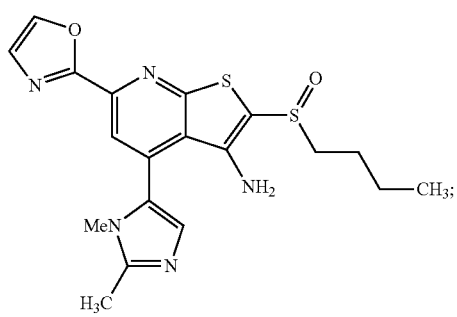
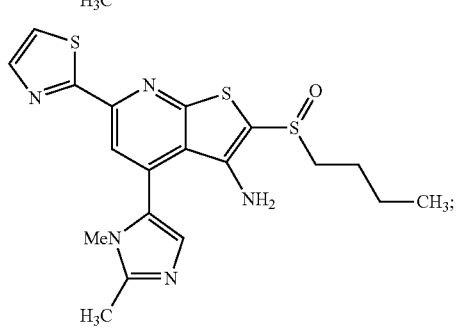
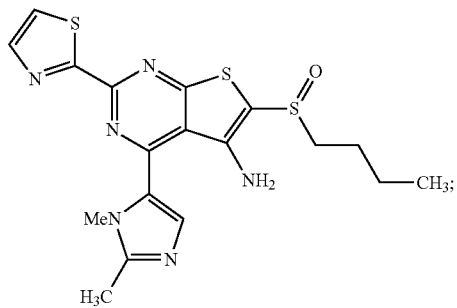
-continued
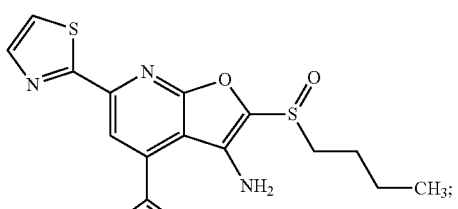
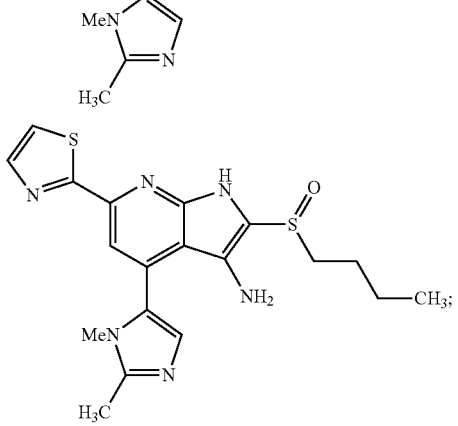
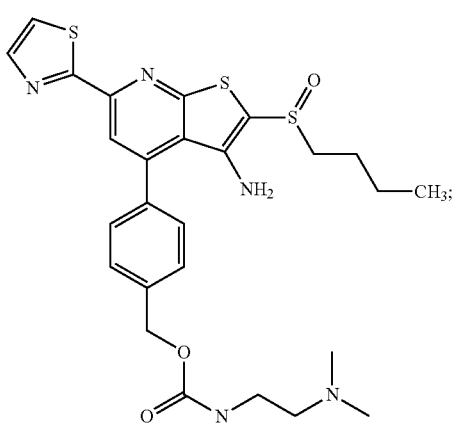
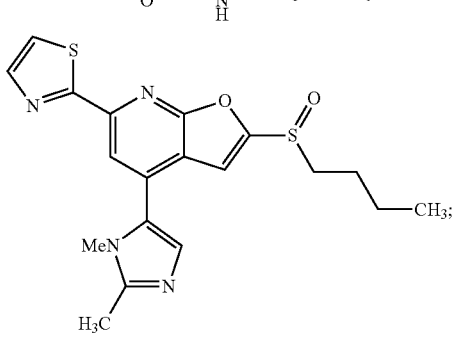
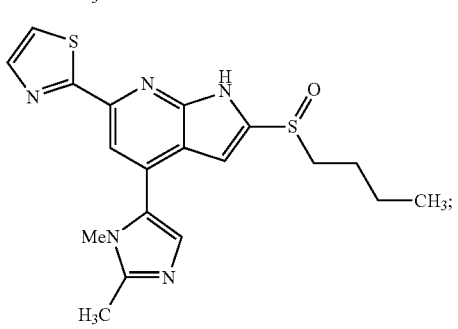

75
-continued
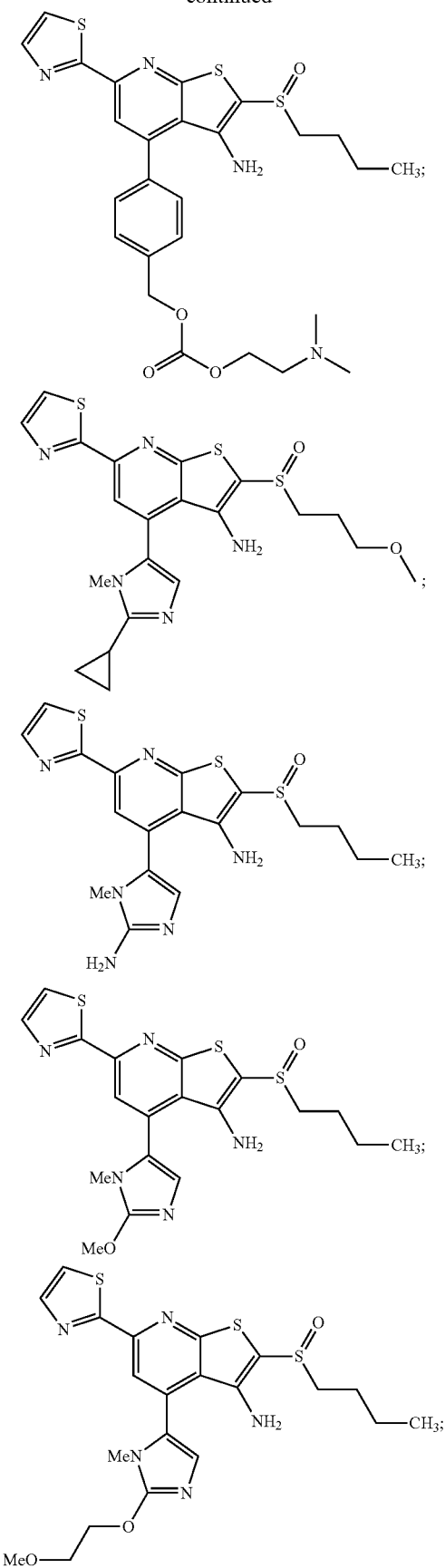
76
-continued
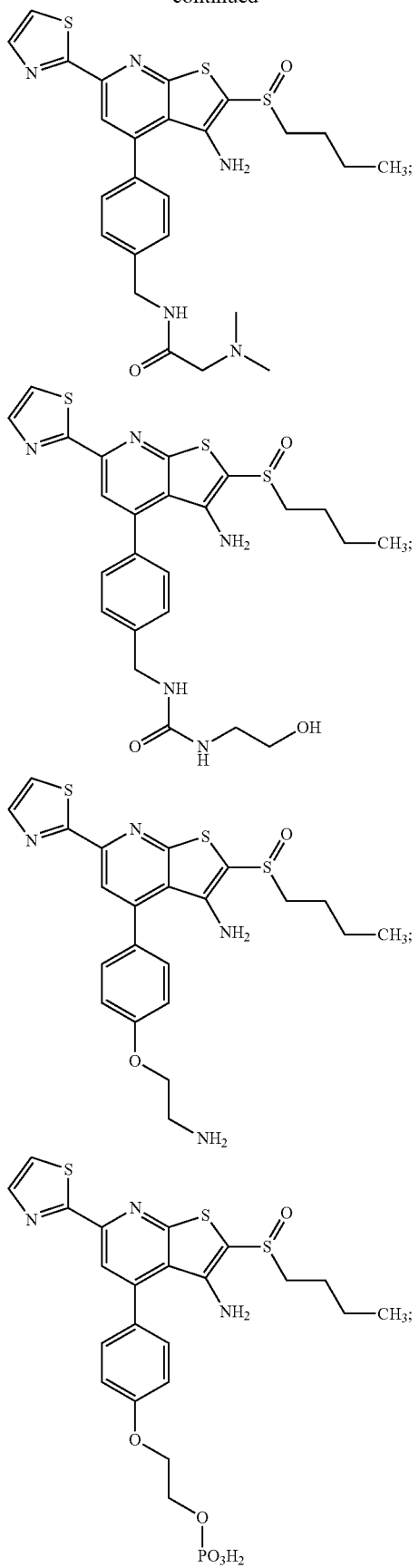

77
-continued
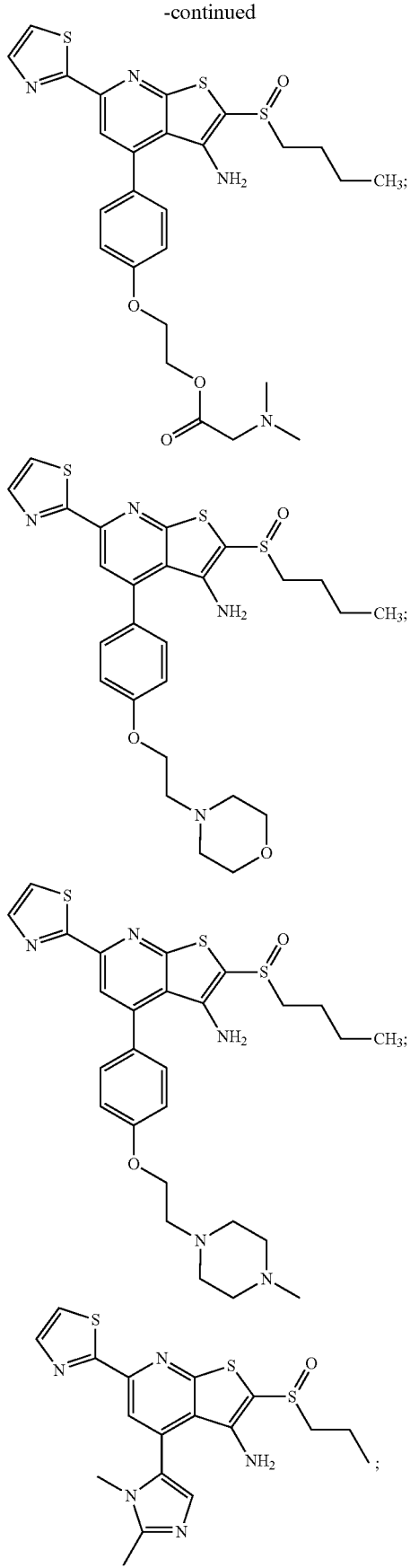
78
-continued
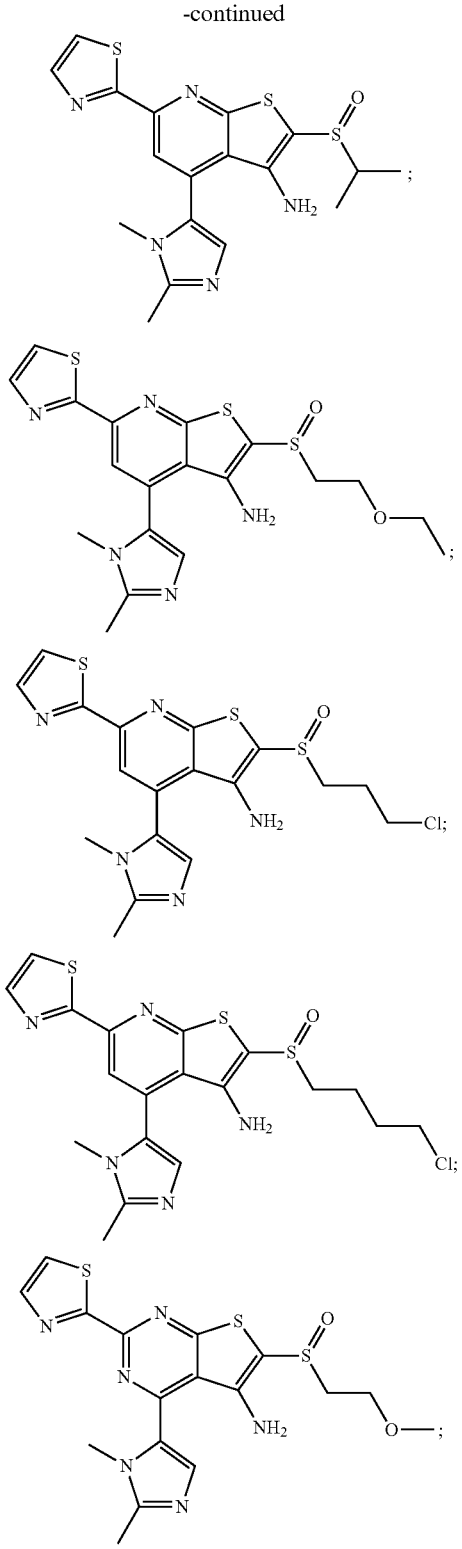

-continued
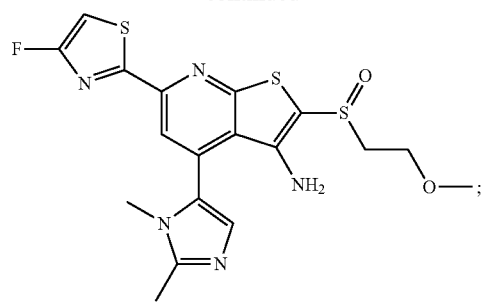
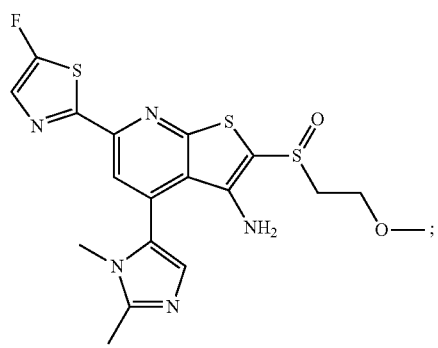
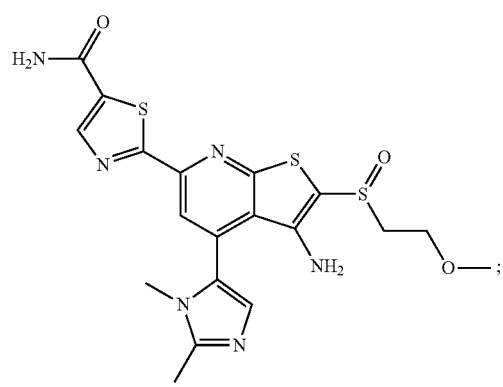
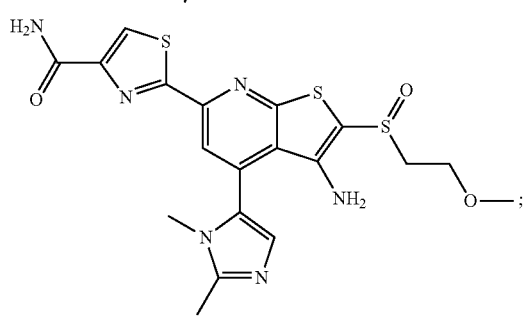
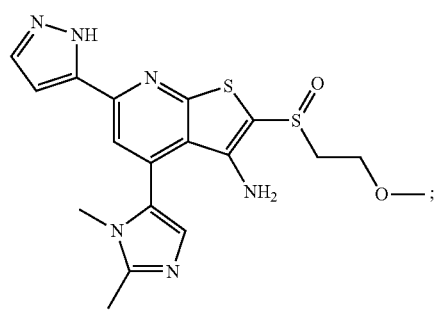
-continued
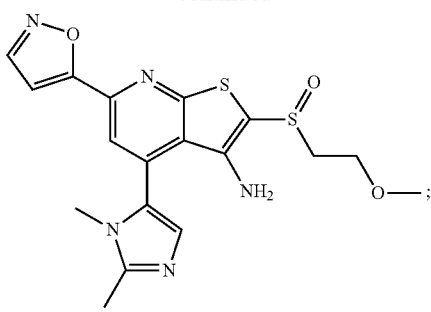
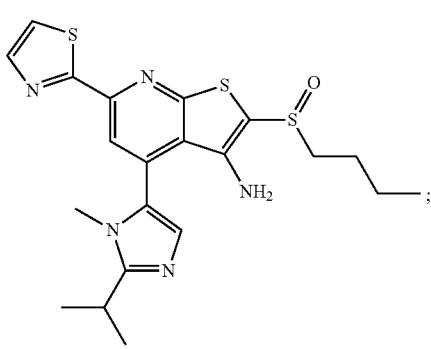
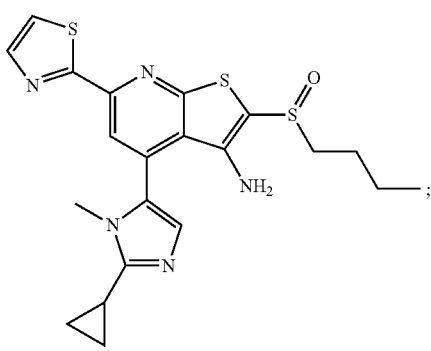
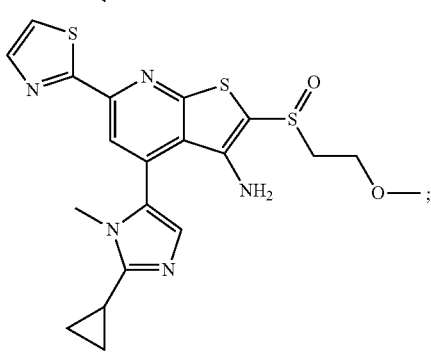
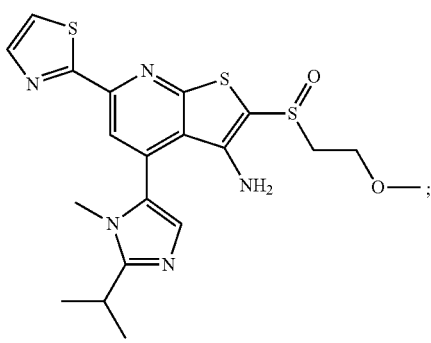

-continued
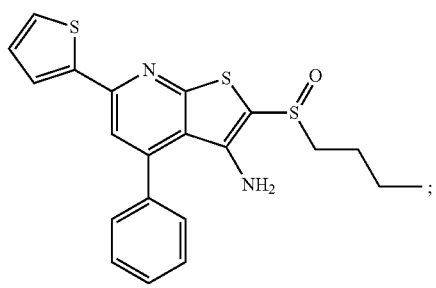
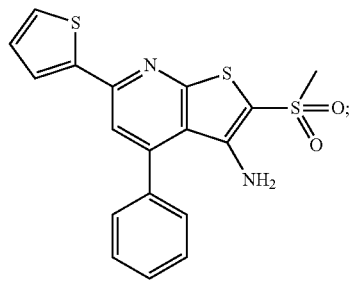
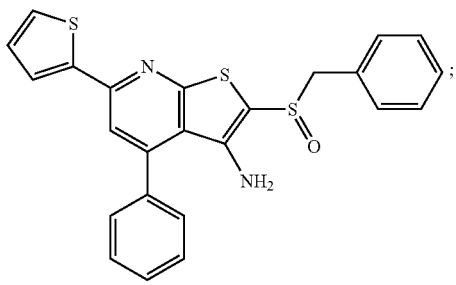
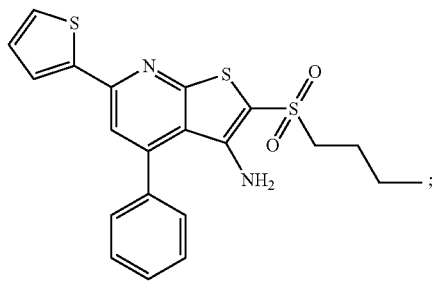
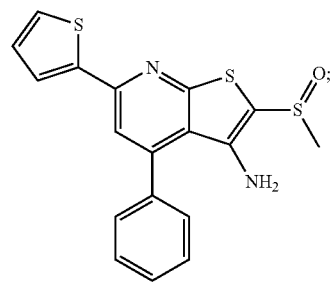
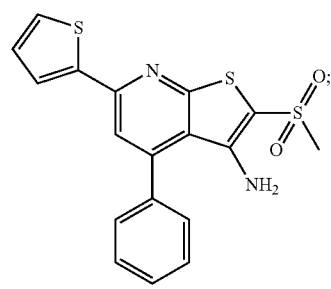
-continued
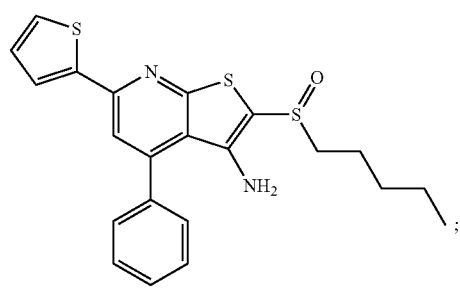
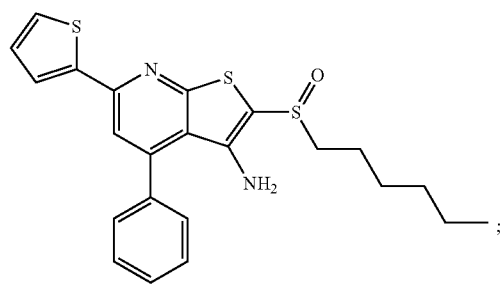
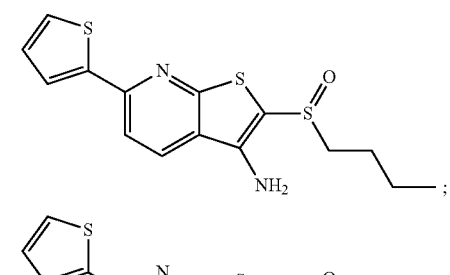
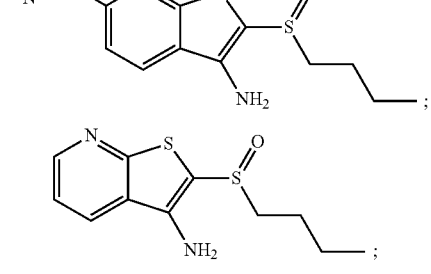
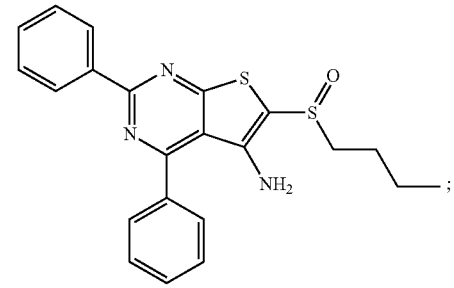
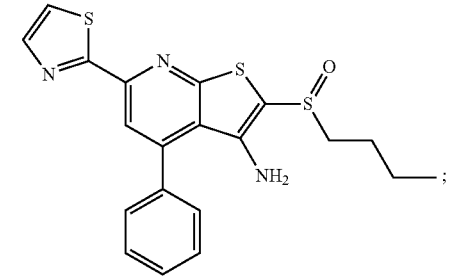

-continued

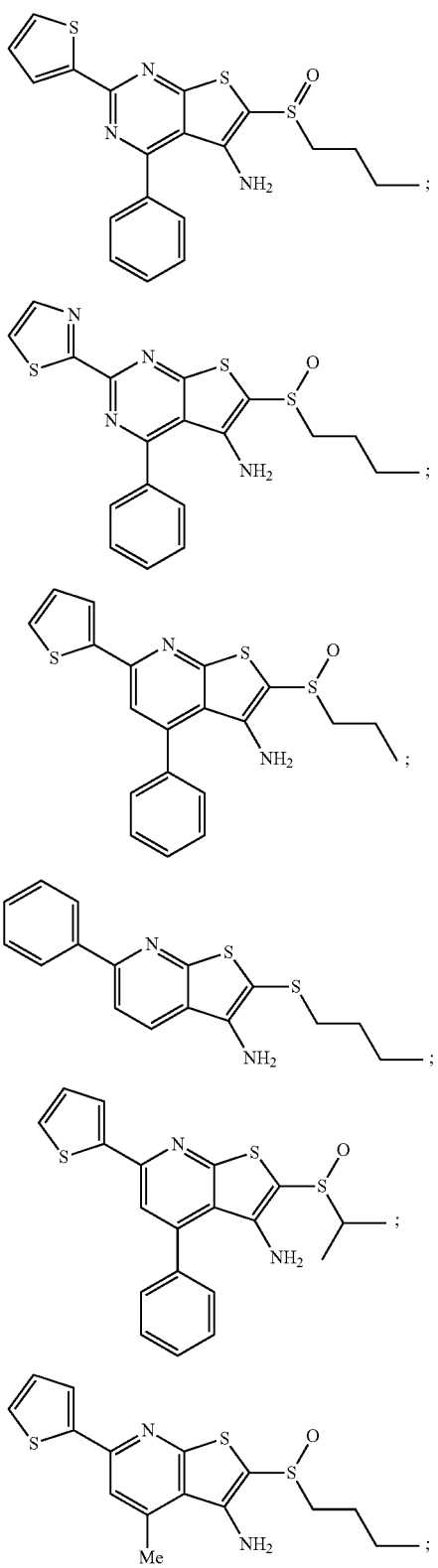

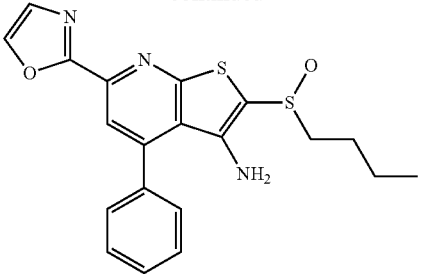

and pharmaceutically acceptable salts thereof.

In certain embodiments, the 15-PGDH inhibitor having formula (I), (II), (III), (IV), (V), (VI), and (VII) can be selected that can ia) at 2.5 μM concentration, stimulate a Vaco503 reporter cell line expressing a 15-PGDH luciferase fusion construct to a luciferase output level of greater than 70 (using a scale on which a value of 100 indicates a doubling of reporter output over baseline); iia) at 2.5 μM concentration stimulate a V9m reporter cell line expressing a 15-PGDH luciferase fusion construct to a luciferase output level of greater than 75; iiia) at 7.5 μM concentration stimulate a LS174T reporter cell line expressing a 15-PGDH luciferase fusion construct to a luciferase output level of greater than 70; and iva) at 7.5 μM concentration, does not activate a negative control V9m cell line expressing TK-renilla luciferase reporter to a level greater than 20; and va) inhibits the enzymatic activity of recombinant 15-PGDH protein at an $IC_{50}$ of less than 1 μM.

In other embodiments, the 15-PGDH inhibitor can ib) at 2.5 μM concentration, stimulate a Vaco503 reporter cell line expressing a 15-PGDH luciferase fusion construct to increase luciferase output; iib) at 2.5 μM concentration stimulate a V9m reporter cell line expressing a 15-PGDH luciferase fusion construct to increase luciferase output; iiib) at 7.5 μM concentration stimulate a LS174T reporter cell line expressing a 15-PGDH luciferase fusion construct to increase luciferase output; ivb) at 7.5 μM concentration, does not activate a negative control V9m cell line expressing TK-renilla luciferase reporter to a luciferase level greater than 20% above background; and vb) inhibits the enzymatic activity of recombinant 15-PGDH protein at an $IC_{50}$ of less than 1 μM.

In other embodiments, the 15-PGDH inhibitor can inhibit the enzymatic activity of recombinant 15-PGDH at an $IC_{50}$ of less than 1 μM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

In other embodiments, the 15-PGDH inhibitor can increase the cellular levels of PGE-2 following stimulation of an A459 cell with an appropriate agent, for example IL1-beta.

In some embodiments, a 15-PGDH inhibitor can include a compound having the following formula (VIII):

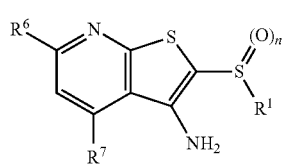

(VIII)

wherein n is 0-2;

R[1], R[6], and R[7] are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$) carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH2, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein R[6] and R[7] may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

15-PGDH inhibitors having formula (VIII) can be synthesized as shown:

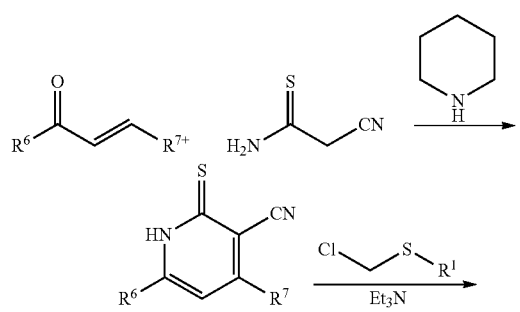

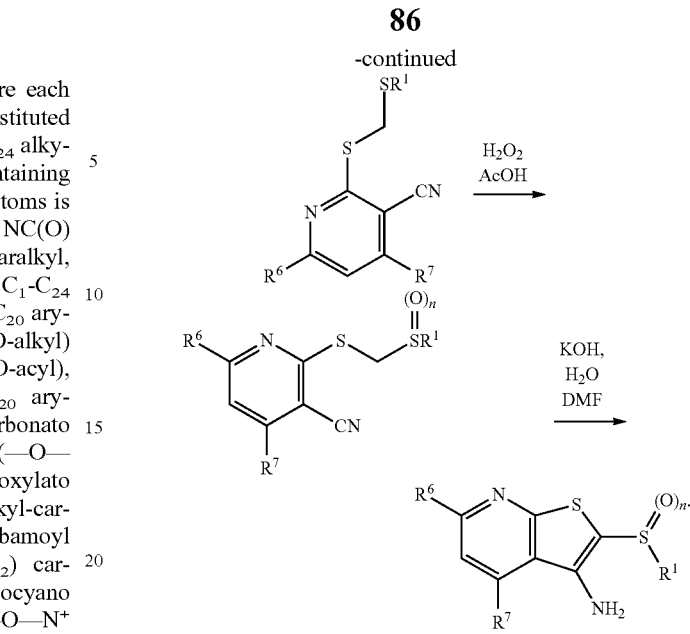

Any reaction solvent can be used in the above preparation process as long as it is not involved in the reaction. For example, the reaction solvent includes ethers such as diethyl ether, tetrahydrofuran and dioxane; halogenized hydrocarbons, such as dichloromethane and chloroform; amines such as pyridine, piperidine and triethylamine; alkylketones, such as acetone, methylethylketone and methylisobutyl; alcohols, such as methanol, ethanol and propanol; non-protonic polar solvent, such as N,N-dimethylformamide, N,N-dimethylacetamide, acetonitrile, dimethylsulfoxide and hexamethyl phosphoric acid triamide. Among non-reactive organic solvents that are ordinarily used in the organic synthesis, preferable solvents are those from which water generated in the reaction can be removed by a Dean-Stark trap. The examples of such solvents include, but are not limited to benzene, toluene, xylene and the like. The reaction product thus obtained may be isolated and purified by condensation, extraction and the like, which is ordinarily conducted in the field of the organic synthesis, if desired, by silica gel column chromatography. The individual enantiomers of PGDH inhibitors having the formula III can be separated by a preparative HPLC using chromatography columns containing chiral stationary phases.

Further, embodiments of this application include any modifications for the preparation method of the 15-PGDH inhibitors described above. In this connection, any intermediate product obtainable from any step of the preparation method can be used as a starting material in the other steps. Such starting material can be formed in situ under certain reaction conditions. Reaction reagents can also be used in the form of their salts or optical isomers.

Depending on the kinds of the substituents to be used in the preparation of the 15-PGDH inhibitors, and the intermediate product and the preparation method selected, novel 15-PGDH inhibitors can be in the form of any possible isomers such as substantially pure geometrical (cis or trans) isomers, optical isomers (enantiomers) and racemates.

In some embodiments, a 15-PGDH inhibitor having formula (VIII) can include a compound with the following formula (IX):

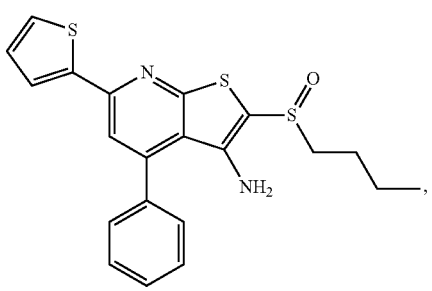

(IX)

and pharmaceutically acceptable salts thereof.

Advantageously, the 15-PDGH inhibitor having formula (IX) was found to: i) inhibit recombinant 15-PGDH at 1 nM concentration; ii) inhibit 15-PGDH in cell lines at 100 nM concentration, iii) increase $PGE_2$ production by cell lines; iv) is chemically stable in aqueous solutions over broad pH range; v) is chemically stable when incubated with hepatocyte extracts, vi) is chemically stable when incubated with hepatocyte cell lines; vii) shows 253 minutes plasma half-life when injected IP into mice; and viii) shows no immediate toxicity over 24 hours when injected IP into mice at 0.6 μmole/per mouse and at 1.2 μmole/per mouse and also no toxicity when injected IP into mice at 0.3 μmole/per mouse twice daily for 21 days.

In other embodiments, a 15-PGDH inhibitor having formula (IX) can include a compound with the following formula (IXa):

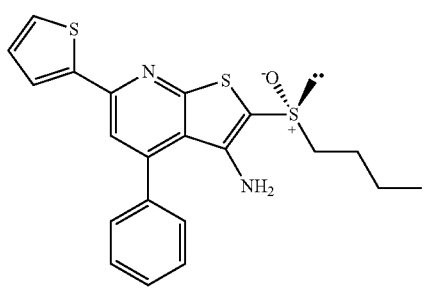

(IXa)

and pharmaceutically acceptable salts thereof.

In still other embodiments, a 15-PGDH inhibitor having formula (IX) can include a compound with the following formula (IXb):

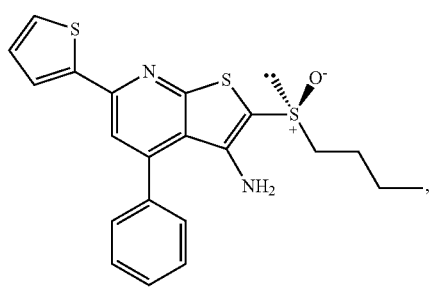

(IXb)

and pharmaceutically acceptable salts thereof.

In other embodiments, the 15-PDHG inhibitor can comprise a (+) or (−) optical isomer of a 15-PGDH inhibitor having formula (IX). In still other embodiments, the 15-PDHG inhibitor can comprise a mixture at least one of a (+) or (−) optical isomer of a 15-PGDH inhibitor having formula (IX). For example, the 15-PGDH inhibitor can comprise a mixture of: less than about 50% by weight of the (−) optical isomer of a 15-PGDH inhibitor having formula (IX) and greater than about 50% by weight of the (+) optical isomer of a 15-PGDH inhibitor having formula (IX), less than about 25% by weight of the (−) optical isomer of a 15-PGDH inhibitor having formula (IX) and greater than about 75% by weight of the (+) optical isomer of a 15-PGDH inhibitor having formula (IX), less than about 10% by weight of the (−) optical isomer of a 15-PGDH inhibitor having formula (IX) and greater than about 90% by weight of the (+) optical isomer of a 15-PGDH inhibitor having formula (IX), less than about 1% by weight of the (−) optical isomer of a 15-PGDH inhibitor having formula (IX) and greater than about 99% by weight of the (+) optical isomer of a 15-PGDH inhibitor having formula (IX), greater than about 50% by weight of the (−) optical isomer of a 15-PGDH inhibitor having formula (IX) and less than about 50% by weight of the (+) optical isomer of a 15-PGDH inhibitor having formula (IX), greater than about 75% by weight of the (−) optical isomer of a 15-PGDH inhibitor having formula (IX) and less than about 25% by weight of the (+) optical isomer of a 15-PGDH inhibitor having formula (IX), greater than about 90% by weight of the (−) optical isomer of a 15-PGDH inhibitor having formula (IX) and less than about 10% by weight of the (+) optical isomer of a 15-PGDH inhibitor having formula (IX), or greater than about 99% by weight of the (−) optical isomer of a 15-PGDH inhibitor having formula (IX) and less than about 1% by weight of the (+) optical isomer of a 15-PGDH inhibitor having formula (IX).

In a still further embodiment, the 15-PDGH inhibitor can consist essentially of or consist of the (+) optical isomer of a 15-PGDH inhibitor having formula (IX). In yet another embodiment, the PDGH inhibitor can consist essentially of or consist of the (−) optical isomer of a 15-PGDH inhibitor having formula (IX).

In other embodiments, a 15-PGDH inhibitor having formula (VIII) can include a compound with the following formula (X):

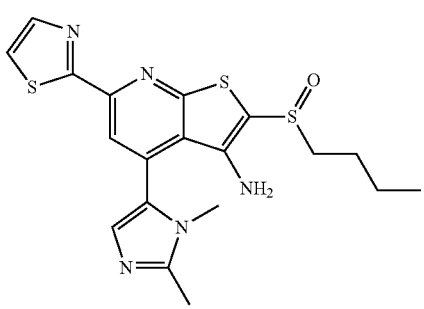

(X)

and pharmaceutically acceptable salts thereof.

Advantageously, the 15-PDGH inhibitor having formula (X) was found to: i) inhibit recombinant 15-PGDH at 3 nM concentration; ii) increase $PGE_2$ production by cell lines at 20 nM; iii) is chemically stable in aqueous solutions over broad pH range; iv) is chemically stable when incubated with mouse, rat and human liver extracts, v) shows 33 minutes plasma half-life when injected IP into mice; viii)

shows no immediate toxicity over 24 hours when injected IP into mice at 50 mg/kg body weight, and ix) is soluble in water (pH=3) at 1 mg/mL.

In other embodiments, a 15-PGDH inhibitor having formula (X) can include a compound with the following formula (Xa):

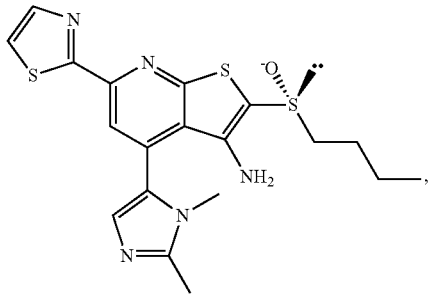

(Xa)

and pharmaceutically acceptable salts thereof.

In still other embodiments, a 15-PGDH inhibitor having formula (X) can include a compound with the following formula (Xb):

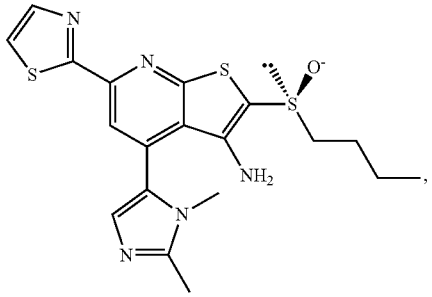

(Xb)

and pharmaceutically acceptable salts thereof.

In other embodiments, the 15-PDHG inhibitor can comprise a (+) or (−) optical isomer of a 15-PGDH inhibitor having formula (X). In still other embodiments, the 15-PDHG inhibitor can comprise a mixture at least one of a (+) or (−) optical isomer of a 15-PGDH inhibitor having formula (X). For example, the 15-PGDH inhibitor can comprise a mixture of: less than about 50% by weight of the (−) optical isomer of a 15-PGDH inhibitor having formula (X) and greater than about 50% by weight of the (+) optical isomer of a 15-PGDH inhibitor having formula (X), less than about 25% by weight of the (−) optical isomer of a 15-PGDH inhibitor having formula (X) and greater than about 75% by weight of the (+) optical isomer of a 15-PGDH inhibitor having formula (X), less than about 10% by weight of the (−) optical isomer of a 15-PGDH inhibitor having formula (X) and greater than about 90% by weight of the (+) optical isomer of a 15-PGDH inhibitor having formula (X), less than about 1% by weight of the (−) optical isomer of a 15-PGDH inhibitor having formula (X) and greater than about 99% by weight of the (+) optical isomer of a 15-PGDH inhibitor having formula (X), greater than about 50% by weight of the (−) optical isomer of a 15-PGDH inhibitor having formula (X) and less than about 50% by weight of the (+) optical isomer of a 15-PGDH inhibitor having formula (X), greater than about 75% by weight of the (−) optical isomer of a 15-PGDH inhibitor having formula (X) and less than about 25% by weight of the (+) optical isomer of a 15-PGDH inhibitor having formula (X), greater than about 90% by weight of the (−) optical isomer of a 15-PGDH inhibitor having formula (X) and less than about 10% by weight of the (+) optical isomer of a 15-PGDH inhibitor having formula (X), or greater than about 99% by weight of the (−) optical isomer of a 15-PGDH inhibitor having formula (X) and less than about 1% by weight of the (+) optical isomer of a 15-PGDH inhibitor having formula (X).

In a still further embodiment, the 15-PDGH inhibitor can consist essentially of or consist of the (+) optical isomer of a 15-PGDH inhibitor having formula (X). In yet another embodiment, the PDGH inhibitor can consist essentially of or consist of the (−) optical isomer of a 15-PGDH inhibitor having formula (X).

It will be appreciated that the other 15-PGDH inhibitors can be used in the methods described herein. These other 15-PGDH inhibitors can include known 15-PGDH inhibitors including, for example, tetrazole compounds of formulas (I) and (II), 2-alkylideneaminooxyacetamide compounds of formula (I), heterocyclic compounds of formulas (VI) and (VII), and pyrazole compounds of formula (III) described in U.S. Patent Application Publication No. 2006/0034786 and U.S. Pat. No. 7,705,041; benzylidene-1,3-thiazolidine compounds of formula (I) described in U.S. Patent Application Publication No. 2007/0071699; phenylfurylmethylthiazolidine-2,4-dione and phenylthienylmethylthiazolidine-2,4-dione compounds described in U.S. Patent Application Publication No. 2007/0078175; thiazolidenedione derivatives described in U.S. Patent Application Publication No. 2011/0269954; phenylfuran, phenylthiophene, or phenylpyrrazole compounds described in U.S. Pat. No. 7,294,641, 5-(3,5-disubstituted phenylazo)-2-hydroxybenzene-acetic acids and salts and lactones described in U.S. Pat. No. 4,725,676, and azo compounds described in U.S. Pat. No. 4,889,846.

The 15-PGDH inhibitors described herein can be provided in a pharmaceutical composition or cosmetic composition depending on the pathological or cosmetic condition or disorder being treated. A pharmaceutical composition containing the 15-PGDH inhibitors described herein as an active ingredient may be manufactured by mixing the derivative with a pharmaceutically acceptable carrier(s) or an excipient(s) or diluting the 15-PGDH inhibitors with a diluent in accordance with conventional methods. The pharmaceutical composition may further contain fillers, anticohesives, lubricants, wetting agents, flavoring agents, emulsifying agents, preservatives and the like. The pharmaceutical composition may be formulated into a suitable formulation in accordance with the methods known to those skilled in the art so that it can provide an immediate, controlled or sustained release of the 15-PGDH inhibitors after being administered into a mammal.

In some embodiments, the pharmaceutical composition may be formulated into a parenteral or oral dosage form. The solid dosage form for oral administration may be manufactured by adding excipient, if necessary, together with binder, disintegrants, lubricants, coloring agents, and/or flavoring agents, to the 15-PGDH inhibitors and shaping the resulting mixture into the form of tablets, sugar-coated pills, granules, powder or capsules. The additives that can be added in the composition may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, and polyethylene glycol may be used as a lubricant; and sucrose, bitter orange peel, citric acid, tartaric acid, may be used as a flavoring agent. In some embodiments, the pharmaceutical composition can be made into aerosol formulations (e.g., they can be nebulized) to be administered via inhalation.

The 15-PGDH inhibitors described herein may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

In some embodiments, the 15-PGDH inhibitors described herein may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

In other embodiments, the 15-PGDH inhibitors described herein may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The pharmaceutical composition may be formulated into various dosage forms as discussed above and then administered through various routes including an oral, inhalational, transdermal, subcutaneous, intravenous or intramuscular route. The dosage can be a pharmaceutically or therapeutically effective amount.

Therapeutically effective dosage amounts of the 15-PGDH inhibitor may be present in varying amounts in various embodiments. For example, in some embodiments, a therapeutically effective amount of the 15-PGDH inhibitor may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the 15-PGDH inhibitor is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the 15-PGDH inhibitor is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage may be a dosage of 10 µg/kg/day, 50 µg/kg/day, 100 µg/kg/day, 250 µg/kg/day, 500 µg/kg/day, 1000 µg/kg/day or more. In various embodiments, the amount of the 15-PGDH inhibitor or pharmaceutical salt thereof is sufficient to provide a dosage to a patient of between 0.01 µg/kg and 10 µg/kg; 0.1 µg/kg and 5 µg/kg; 0.1 µg/kg and 1000 µg/kg; 0.1 µg/kg and 900 µg/kg; 0.1 µg/kg and 900 µg/kg; 0.1 µg/kg and 800 µg/kg; 0.1 µg/kg and 700 µg/kg; 0.1 µg/kg and 600 µg/kg; 0.1 µg/kg and 500 µg/kg; or 0.1 µg/kg and 400 µg/kg.

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

Various embodiments may include differing dosing regimen. In some embodiments, the 15-PGDH inhibitor can be administered via continuous infusion. In some embodiments, the continuous infusion is intravenous. In other embodiments, the continuous infusion is subcutaneous. Alternatively or additionally, in some embodiments, the 15-PGDH inhibitor can be administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

For topical application, the composition can be administered in the form of aqueous, alcoholic, aqueous-alcoholic or oily solutions or suspensions, or of a dispersion of the lotion or serum type, of emulsions that have a liquid or semi-liquid consistency or are pasty, obtained by dispersion of a fatty phase in an aqueous phase (O/W) or vice versa (W/O) or multiple emulsions, of a free or compacted powder to be used as it is or to be incorporated into a physiologically acceptable medium, or else of microcapsules or microparticles, or of vesicular dispersions of ionic and/or nonionic type. It may thus be in the form of a salve, a tincture, milks, a cream, an ointment, a powder, a patch, an impregnated pad, a solution, an emulsion or a vesicular dispersion, a lotion, aqueous or anhydrous gels, a spray, a suspension, a shampoo, an aerosol or a foam. It may be anhydrous or aqueous. It may also comprise solid preparations constituting soaps or cleansing cakes.

Pharmaceutical compositions including the 15-PGDH inhibitor described herein can additionally contain, for example, at least one compound chosen from prostaglandins, in particular prostaglandin $PGE_1$, $PGE_2$, their salts, their esters, their analogues and their derivatives, in particular those described in WO 98/33497, WO 95/11003, JP 97-100091, JP 96-134242, in particular agonists of the prostaglandin receptors. It may in particular contain at least one compound such as the agonists (in acid form or in the form of a precursor, in particular in ester form) of the prostaglandin $F_2\alpha$ receptor, such as for example latanoprost, fluprostenol, cloprostenol, bimatoprost, unoprostone, the agonists (and their precursors, in particular the esters such as travoprost) of the prostaglandin $E_2$ receptors such as 17-phenyl $PGE_2$, viprostol, butaprost, misoprostol, sulprostone, 16,16-dimethyl $PGE_2$, 11-deoxy $PGE_1$, 1-deoxy $PGE_1$, the agonists and their precursors, in particular esters, of the prostacycline (IP) receptor such as cicaprost, iloprost, isocarbacycline, beraprost, eprostenol, treprostinil, the agonists and their precursors, in particular the esters, of the prostaglandin $D_2$ receptor such as BW245C ((4S)-3-[(3R,S)-3-cyclohexyl-3-isopropyl]-2,5-dioxo)-4-imidazolidinehept-anoic acid), BW246C ((4R)-(3-[(3R,S)-3-cyclohexyl-3-isopropyl]-2,5-dioxo)-4-imidazolidinehept-anoic acid), the agonists and their precursors, in particular the esters, of the receptor for the thromboxanes A2 (TP) such as I-BOP ([1S-[1a,2a(Z), 3b(1E,3S),4a]]-7-[3-[3-hydroxy-4-[4-(iodo-phenoxy)-1-butenyl]-7-oxabicyclo-[2.2.1]hept-2-yl]-5-heptenoic acid).

Advantageously, the composition can include at least one 15-PGDH inhibitor as defined above and at least one prostaglandin or one prostaglandin derivative such as for example the prostaglandins of series 2 including in particular $PGF_2\alpha$ and $PGE_2$ in saline form or in the form of precursors, in particular of the esters (example isopropyl esters), their derivatives such as 16,16-dimethyl $PGE_2$, 17-phenyl $PGE_2$ and 16,16-dimethyl $PGF_{2\alpha}$ 17-phenyl $PGF_{2\alpha}$, prostaglandins of series 1 such as 11-deoxyprostaglandin E1, 1-deoxyprostaglandin E1 in saline or ester form, is their analogues, in particular latanoprost, travoprost, fluprostenol, unoprostone, bimatoprost, cloprostenol, viprostol, butaprost, misoprostol, their salts or their esters.

The invention is further illustrated by the following examples, which is not intended to limit the scope of the claims.

Example 1

Analysis of Effect of SW033291 on Bone Marrow Function

This Example shows effects of SW033291 on bone marrow function.

FIGS. 1(A-C) show analysis of bone marrow of wild-type mice versus mice that are homozygous genetic knockouts for 15-PGDH (PGDH−/− mice). Total bone marrow cellularity and percent of Sca1+/c-Kit+ cells in lineage negative (SKL) cells are the same in both sets of mice. However, bone marrow from 15-PGDH−/− mice shows an approximately 50% increase in numbers of hematopoietic colonies generated when marrow is plated into methylcelluose. 15-PGDH knockout mice are denoted by label PGDH mice and by label 15-PGDH. WT denotes wild-type mice.

Figure 2:
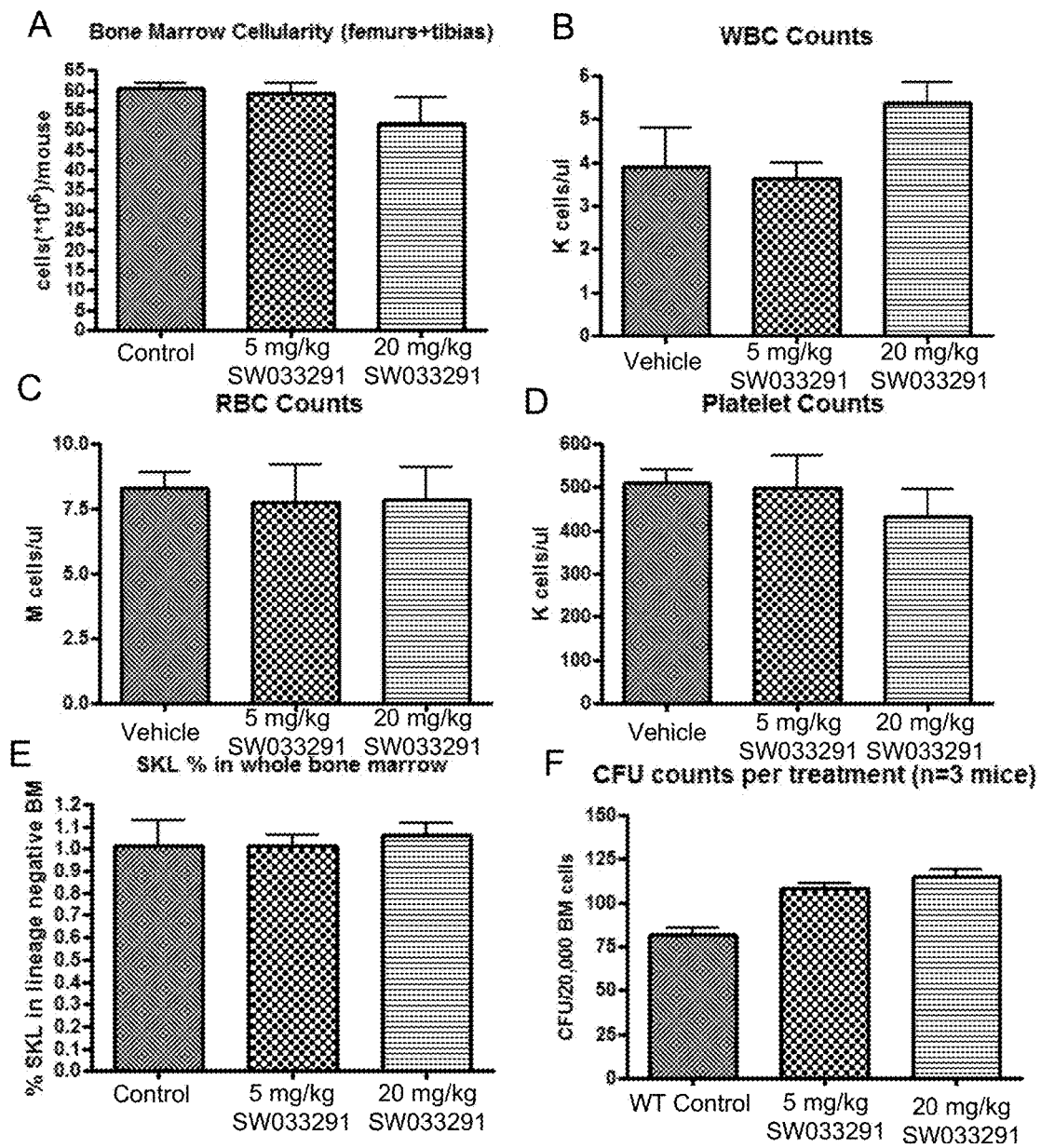
FIGS. 2(A-F) illustrate graphs showing: (A) bone marrow cellularity of mice treated with SW033291; (B) white blood cell (WBC) counts in mice treated SW033291; (C) red blood cell (RBC) counts in mice treated SW033291; (D) platelet counts in mice treated SW033291; (E) SKL % in whole bone marrow of mice treated with SW033291; and (F) CFU counts in mice treated SW033291.

FIGS. 2(A-F) shows assays in which bone marrow is harvested from a wild-type mouse, and incubated ex vivo on ice for 2 hours with either SW033291 (0.5 µM), or 1 µM PGE2 or 1 µM 16,16-dimethyl PGE2 (dmPGE2). Treated marrow is again then plated into methylcellulose for counting of hematopoietic colonies. SW033291 treated marrow again shows an approximately 50% increase in the number of bone marrow derived colonies generated. Under these conditions, a lesser increase is seen in marrow treated with PGE2, and a slightly greater increase is seen in marrow treated with dmPGE2.

Figure 3:
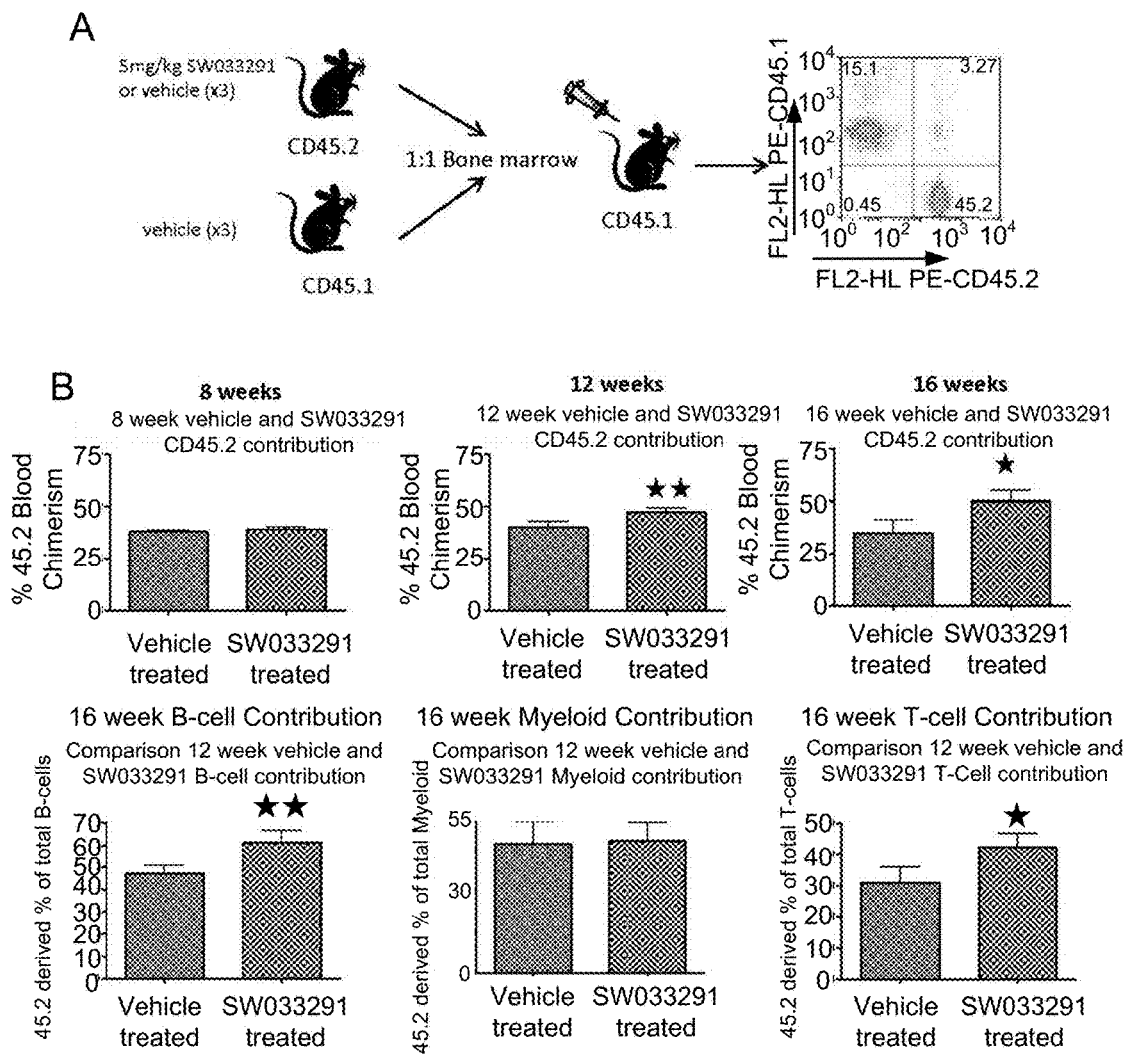
FIGS. 3(A-B) illustrate: (A) a schematic diagram following CD45.2 antigen marked cells in lethally irradiated C57BL/6J mice rescued with a bone marrow transplant from donor mice treated with SW033291 or with vehicle; and (B) graphs showing chimerism, of donor B-Cells, myeloid cells, and T-Cells after such treatment.

FIGS. 3(A-C) show a study of C57BL/6J mice treated with IP SW033291 administered in a vehicle of 10% Ethanol, 5% Cremophor EL, 85% D5W at a dose of 5 mg/kg or 20 mg/kg. Panel A shows mouse bone marrow cellularity, white blood count (wbc), red blood count (rbc) and platelets counts. Panel B shows percent of Scal+/c-Kit+ cells in lineage negative (SKL) cells are unchanged in SW033291 treated mice. Panel C shows that marrow from SW033291 treated mice gives rise to approximately 30% increase in numbers of hematopoietic colonies generated when marrow is plated into methylcelluose. Experimental conditions are noted on the figure.

Figure 4:
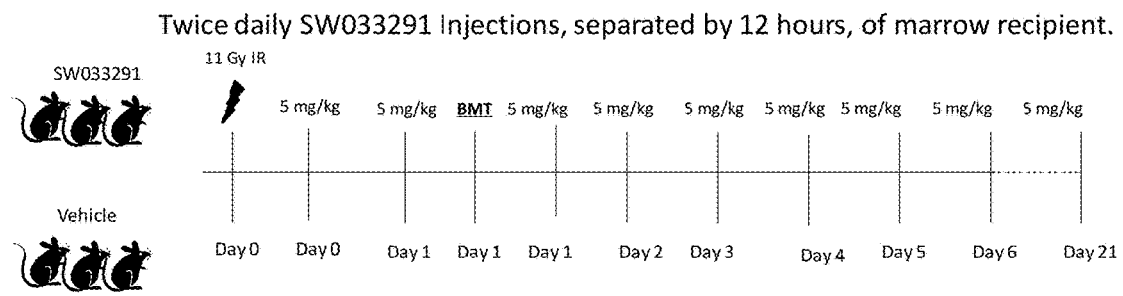
FIG. 4 illustrates a schematic diagram showing schema of a study in which C57BL/61 mice are irradiated with 11GY on day 0 and followed by treatment with SW033291.
Figure 5A:
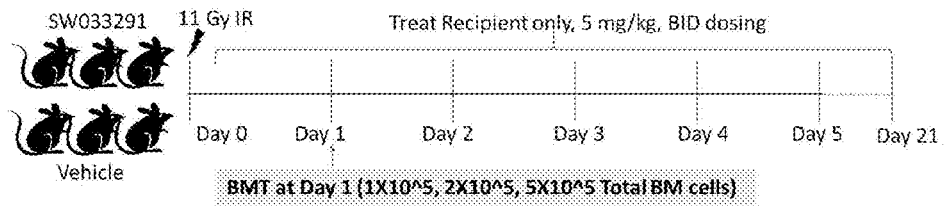
FIGS. 5(A-D) illustrate: (A) a schematic illustration showing the design of a study of enhanced survival in mice receiving a bone marrow transplant and also administered the 15-PGDH inhibitor SW033291; (B) graphical survival curves for mice transplanted with 100,000 donor cells; (C) graphical survival curves for mice transplanted with 200,000 donor cells; and (D) graphical survival curves for mice transplanted with 500,000 donor cells.
Figure 5B:
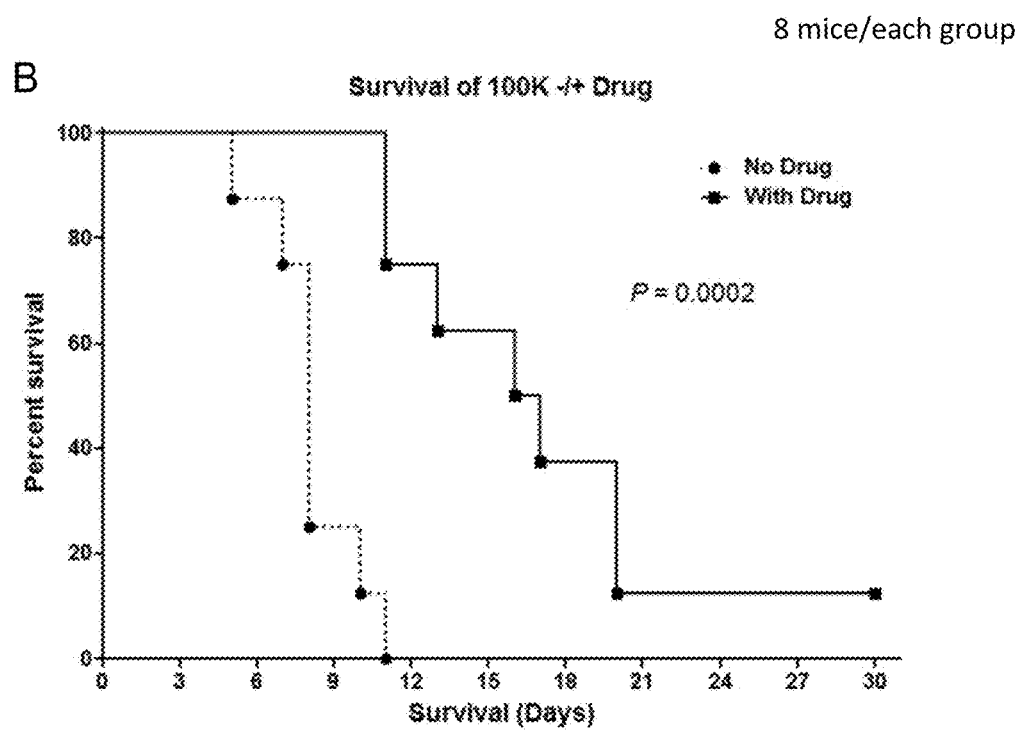
Figure 5C:
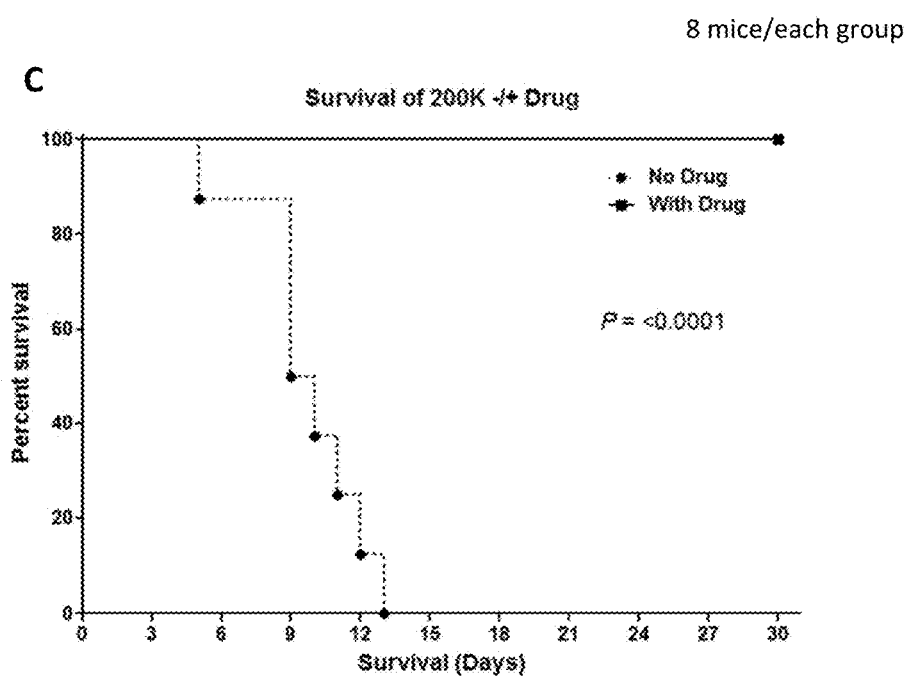
Figure 5D:
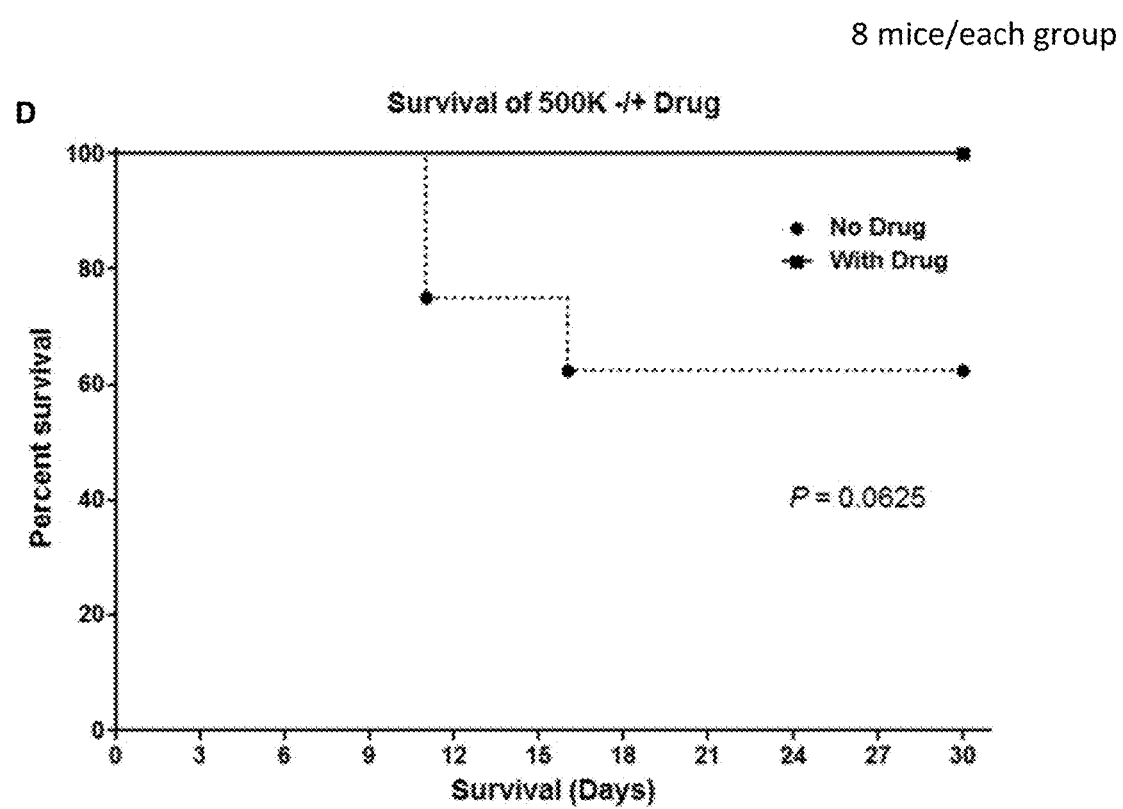

FIGS. 4(A-B) show analysis of marrow from CD45.2 antigen marked C57BL/6J mice that were treated with SW033291 5 mg/kg IP daily for 3 doses in a vehicle of 10% Ethanol, 5% Cremophor EL, 85% D5W or that were treated with vehicle alone. On day 3 mice were sacrificed, marrow flushed and mixed at a 1:1 ratio with vehicle treated CD45.1 marrow. 2 million whole BM cells were injected into the tail vein of lethally irradiated CD45.1 mice and percent chimerism measured via flow cytometry at weeks 8, 12, 16. As shown, at weeks 12 and 16 the percent blood chimerism of CD45.2 marked cells was significantly increased in recipient mice whose CD45.2 marked marrow was harvested from SW033291 treated donor mice, as opposed to vehicle control treated donor mice. In other words, marrow from SW033291 treated mice demonstrated long term increased fitness in competition with control marrow. In particular, at week 16 CD45.2 harvested from SW033291 treated mice show a significant increase in contribution to B and T cell populations, suggesting marrow from SW033291 treated mice promotes earlier reconstitution of lymphoid populations and earlier return to immune competence.

presumed to have full hematopoietic reconstitution. Thus treatment with the 15-PGDH inhibitor SW033291 promoted survival of mice receiving a bone marrow transplant, an observation consistent with SW033291 enabling more rapid and complete hematopoietic reconstitution in the transplanted mice. Other 15-PGDH inhibitors with activity similar to SW033291 would be predicted to have similar activity in supporting hematopoietic reconstitution. Treatment with SW033291 also enabled mice to be successfully transplanted with a smaller inoculum of donor bone marrow than the 1,000,000 cells that are standardly needed. These observations suggest SW033291, as well as other similar 15-PGDH inhibitors, is able to support successful transplantation with smaller numbers of donor stem cells. Such activity would be of particular utility in settings, such as transplantation with umbilical cord stem cells, in which donor cell numbers are limited. Improved survival of transplanted mice treated with SW033291 suggests efficacy of SW033291, and of similar 15-PGDH inhibitors, as replacements for, or in enabling decreased use of, other treatments or growth factors commonly employed in support of patients receiving bone marrow, hematopoietic stem cell, and cord blood stem cell transplants. Improved survival of transplanted mice treated with SW033291 is consistent with SW033291, and by extension other similar 15-PGDH inhibitors, having activity in reducing infections in the transplanted mice, and/or in promoting recovery of mice intestines from damage by radiation, and/or in reducing pulmonary toxicity from radiation.

TABLE 1

| Treatment | Mouse survival Cell number | 13-Mar Day 0 | 14-Mar Day 1 | 15-Mar Day 2 | 16-Mar Day 3 | 17-Mar Day 4 | 18-Mar Day 5 | 19-Mar Day 6 | 20-Mar Day 7 | 21-Mar Day 8 | 22-Mar Day 9 | 23-Mar Day 10 | 24-Mar Day 11 | 25-Mar Day 12 | 26-Mar Day 13 | 1-Apr Day 19 |
|---|---|---|---|---|---|---|---|---|---|---|---|---|---|---|---|---|
| Control | $1 \times 10^5$ | 3 | 3 | 3 | 2 | 0 | | | | | | | | | | |
| Control | $2 \times 10^5$ | 3 | 3 | 3 | 3 | 3 | 2 | 1 | 0 | | | | | | | |
| Control | $5 \times 10^5$ | 3 | 3 | 3 | 3 | 3 | 3 | 2 | 1 | 1 | 1 | 1 | 1 | 1 | 0 | |
| SW033291 | $1 \times 10^5$ | 3 | 3 | 3 | 3 | 2 | 1 | 0 | | | | | | | | |
| SW033291 | $2 \times 10^5$ | 3 | 3 | 3 | 3 | 3 | 3 | 2 | 2 | 2 | 2 | 2 | 2 | 1 | 0 | |
| SW033291 | $5 \times 10^5$ | 3 | 3 | 3 | 3 | 3 | 3 | 3 | 3 | 2 | 2 | 2 | 2 | 2 | 2 | ... 2 |

In an additional study, C57BL/6J mice are irradiated with 11Gy on day 0, followed by treatment with SW033291 5 mg/kg IP twice daily (bid) in a vehicle of 10% Ethanol, 5% Cremophor EL, 85% D5W, or with vehicle only for 21 days. Mice treated with vehicle or with SW033291 all receive an allograft of marrow from a donor C57BL/6J mouse at a dose of either 100,000 cells, 200,000 cells, 500,000 cells. 3 control and 3 SW033291 mice are assessed under each condition. The experimental design is depicted in FIG. 50.

Table 1 shows the number of surviving mice in each cohort over the first 19 days of study. Under the conditions of the mouse colony during this study, control mice receiving 100,000-500,000 cells are all dead between days 4-13 of study. In contrast, two SW033291 treated mice receiving 500,000 cells remain alive on day 19 of the study and are Example 2

Analysis of Effect of SW033291 on Radiation Survival

This Example shows studies of the effect of SW033291 in mice receiving whole body irradiation.

Table 2 shows the results of a study of 15 week old C57BL/6J female mice irradiated with 7Gy, 9Gy, or 11Gy, and receiving daily SW033291 5 mg/kg IP in a vehicle of 10% Ethanol, 5% Cremophor EL, 85% D5W for 7 doses, or receiving vehicle alone. The table shows the number of mice surviving on sequential days of the study. Under the conditions of the mouse colony during this experiment, mice receiving a lethal dose of 11Gy lived 48 hours longer if treated with SW033291 than if receiving vehicle control, with control mice all dead on day 8; whereas SW033219 treated mice were all dead on day 10.

TABLE 2

| Radiation Dose | Treatment Arm | 10/2 Day 0 | 10/3 Day 1 | 10/4 Day 2 | 10/5 Day 3 | 10/6 Day 4 | 10/7 Day 5 | 10/8 Day 6 | 10/9 Day 7 | 10/10 Day 8 | 10/11 Day 9 | 10/12 Day 14 | 10/13 Day 15 | Day 16 | 10/23 Day 25 |
|---|---|---|---|---|---|---|---|---|---|---|---|---|---|---|---|
| 7 Gy | Saline | 3 | 3 | 3 | 3 | 3 | 3 | 3 | 3 | 3 | 3 | 3 | 3 | | Looks Healthy |
| | SW033291 | 3 | 3 | 3 | 3 | 3 | 3 | 3 | 3 | 3 | 3 | 3 | 3 | | Looks Healthy |
| 9 Gy | Saline | 3 | 3 | 3 | 3 | 3 | 3 | 3 | 3 | 2 | 1 | 1 | 0 | | |
| | SW033291 | 3 | 3 | 3 | 3 | 3 | 3 | 3 | 3 | 2 | 2 | 1 | 0 | | |
| 11 Gy | Saline | 3 | 3 | 3 | 2 | 0 | | | | | | | | | |
| | SW033291 | 3 | 3 | 3 | 3 | 3 | 2 | 0 | | | | | | | |

Table 3 shows the number of mice surviving on sequential days of a study of mice treated at 11Gy treated with either vehicle control or with SW033291 IP, in a vehicle of 10% Ethanol, 5% Cremophor EL, 85% D5W, with SW033291 administered either at 5 mg/kg daily for 7 days, 5 mg/kg daily throughout the study, or at 5 mg/kg twice daily for 7 days. Again mice treated with SW033291 on any of these dosing schedules live on average 1-2 days longer than mice receiving vehicle control. The activity of SW033291 in promoting resistance to toxic effects of radiation may extend to SW033291 and other similar 15-PGDH inhibitors in promoting resistance to other similar toxic insults including but not limited to Cytoxan, fludarabine, chemotherapy and immunosuppressive therapy.

TABLE 3

| Treatment Conditions | Friday 12-Oct Day 0 | Wed. 17-Oct Day 5 | Thurs. 18-Oct Day 6 | Friday 19-Oct Day 7 | Saturday 20-Oct Day 8 | Sunday 21-Oct Day 9 | Monday 22-Oct Day10 |
|---|---|---|---|---|---|---|---|
| 11 Gy Saline (7 days, 1 dose daily) | 2 | 2 | 2 | 2 | 0 | | |
| 11 Gy SW033291 (1 dose/daily) for 7 days | 3 | 3 | 3 | 3 | 2 | 1 | 0 |
| 11 Gy SW033291 (1 dose/daily, continuous every day) | 3 | 3 | 3 | 3 | 3 | 2 | 0 |
| 11 Gy Saline (7 days, 2 dose/daily) | 3 | 3 | 3 | 2 | 1 | 0 | 0 |
| 11 Gy SW033291 (7 days, 2 dose daily) | 3 | 3 | 3 | 3 | 3 | 2 | 0 |

Example 3

Analysis of Effect of SW033291 on Survival of Mice Following Bone Marrow Transplant FIG. 5 shows enhanced survival in mice receiving a bone marrow transplant and also administered the 15-PGDH inhibitor SW033291. FIG. 5A shows the design of the study. Mice were irradiated with a bone marrow ablative dose of 11Gy on day 0, followed by administration of SW033291 in 5 mg/kg twice daily by intraperitoneal injection in a vehicle of 10% Ethanol, 5% Cremophor EL, 85% D5W at a concentration of 125 µg/200 µl. A matched control cohort received injections with vehicle only. On day one mice received an infusion of donor marrow at doses of 100,000 cells; 200,000 cells; or 500,000 cells. FIG. 5B shows graphical survival curves for mice transplanted with 100,000 donor cells. FIG. 5C shows graphical survival curves for mice transplanted with 200,000 donor cells. FIG. 5D shows graphical survival curves for mice transplanted with 500,000 donor cells. Table 4 shows tabular survival data for all mice in the study on study day 30. Among mice receiving 100,000 donor cells, all mice succumb, but SW033291 treated mice show an approximate doubling of median survival. Among mice receiving 200,000 donor cells, all control mice were dead by day 12. In contrast, all mice receiving 200,000 donor cells plus SW033291 survived at 30 days of observation and were successfully engrafted. Among mice receiving 500,000 donor cells, control mice showed a 37.5% mortality; whereas, mice receiving SW033291 again all survived.

TABLE 4

| Dose | Vehicle Survival | SW033291 Survival |
|---|---|---|
| 1 * 10$^5$ | 0/8 | 1/8 |
| 2 * 10$^5$ | 0/8 | 8/8 |
| 5 * 10$^5$ | 5/8 | 8/8 |

Figure 6A:
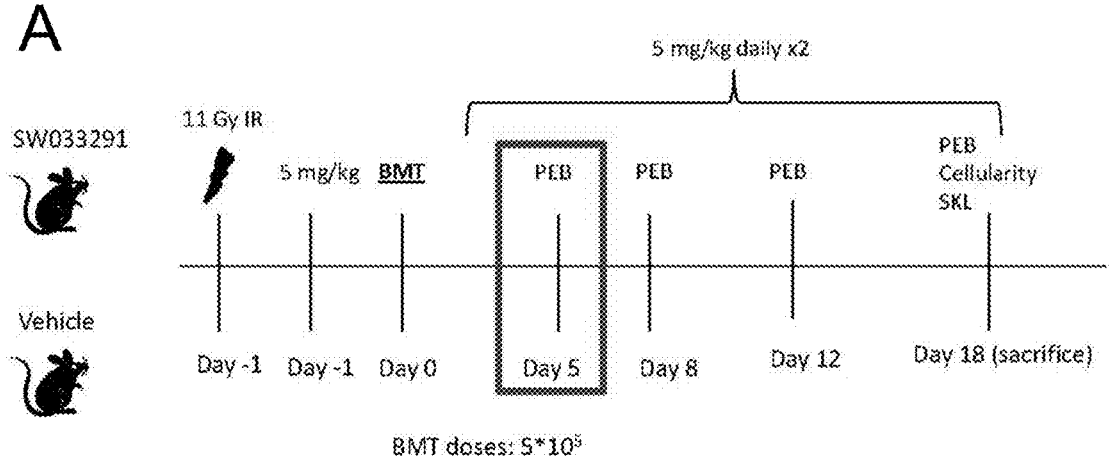
FIGS. 6(A-C) illustrate: (A) a schematic illustration showing measurements on blood and bone marrow on day 5 after transplant; (B) a graph showing that SW033291 treated mice have significantly higher total white count; (C) a graph showing that SW033291 treated mice have significantly higher total platelet count. The star symbol denotes $P<0.05$.
Figure 6B:
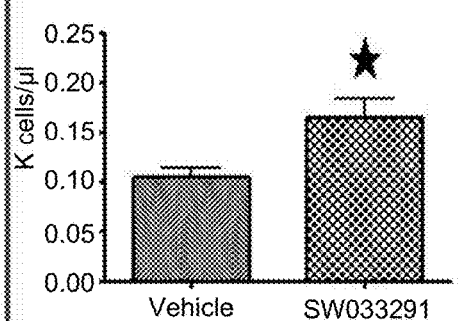
Figure 6C:
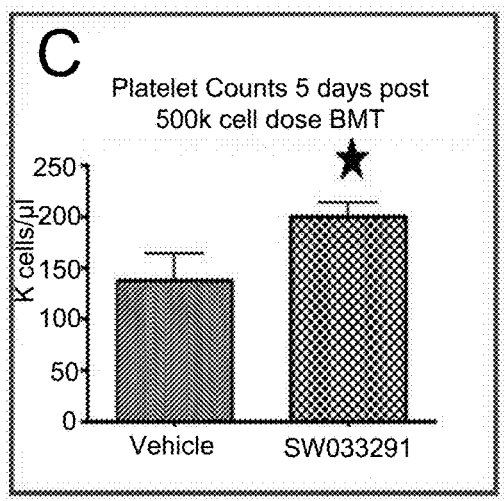

FIG. 6 shows a set of studies conducted on lethally irradiated mice that received 500,000 donor marrow cells and were treated with either SW033291 at 5 mg/kg intraperitoneal dose twice daily or with vehicle control, in a design otherwise identical to that used for the studies of FIG. 5. FIG. 6A shows measurements on blood and bone marrow on day 5 after transplant, with FIG. 6B showing that SW033291 treated mice have significantly higher total white count and FIG. 6C showing that SW033291 treated mice have significantly higher total platelet count. The star symbol denotes $P<0.05$.

Figure 7A:
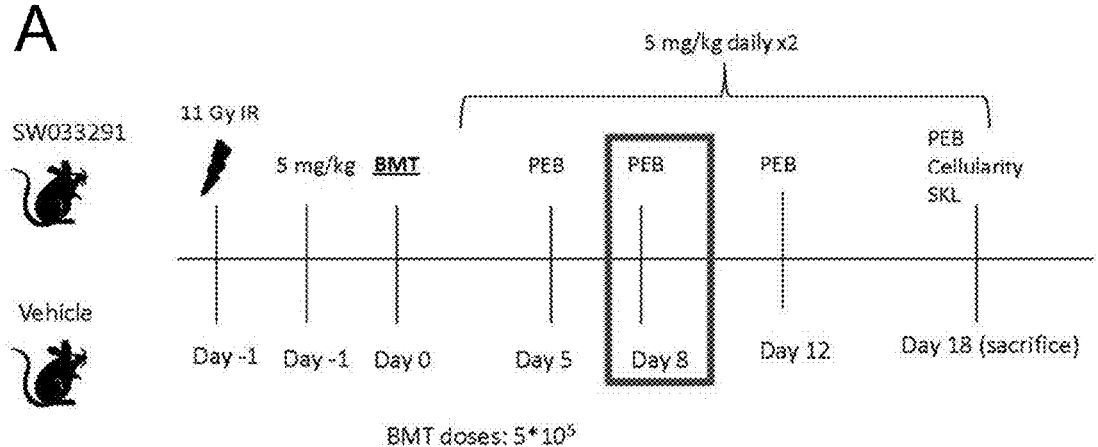
FIGS. 7(A-B) illustrate: (A) a schematic illustration showing measurements on blood and bone marrow on day 8 after transplant; and (B) a graph showing that SW033291 treated mice have significantly higher platelet count than control, with drug treated mice having 77,000 platelets compared to control mice having 39,500 platelets. The star symbol denotes $P<0.05$.
Figure 7B:
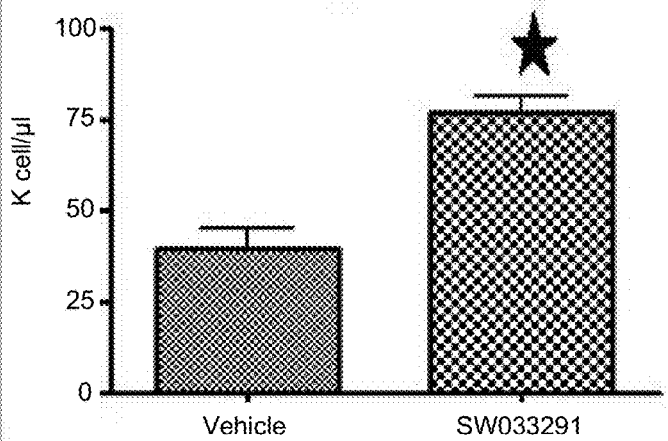

FIG. 7A shows measurements on blood and bone marrow on day 8 after transplant. FIG. 7B shows that SW033291 treated mice have significantly higher platelet count than control, with drug treated mice having 77,000 platelets compared to control mice having 39,500 platelets. The star symbol denotes $P<0.05$.

FIG. 8A shows measurements on blood and bone marrow on day 12 after transplant. FIG. 8B shows that SW033291 treated mice have significantly higher neutrophil counts, with drug treated mice having 332 neutrophils compared to control mice having 125 neutrophils. FIG. 8C shows that on day 12 after transplant, SW033291 treated mice have significantly higher hemoglobin count than controls, with drug treated mice having hemoglobin level of 11.58 and control mice having hemoglobin level of 8.3. Additionally, FIG. 8D shows SW033291 treated mice also have significantly greater total white counts than control mice. The star symbol denotes $P<0.05$.

FIG. 9A shows measurements on blood and bone marrow on day 18 after transplant. SW033291 treated mice have significantly higher total white count (FIG. 9B), lymphocyte count (FIG. 9C), and neutrophil count (FIG. 9D), with drug treated mice having 835 neutrophils and control mice having 365 neutrophils (FIG. 9D). In comparison with counts on day 12, administration of SW033291 accelerates recovery of neutrophil counts by nearly 6 days (FIG. 8B versus FIG. 9D). FIG. 8E also shows that on day 18 drug treated mice have significantly higher platelet counts than control mice. Last, day 18, drug treated mice have nearly 4-fold increased percentage (FIG. 8F) and total numbers (FIG. 9G) of SKL marked bone marrow stem cells than do control mice, with drug treated mice having a mean of 4127 SKL marked bone marrow cells compared to control mice having a mean of 967 SKL marked bone marrow cells. The star symbol denotes $P<0.05$.

FIG. 10(A) shows measurement of PGE2 (pg of PGE2/mg tissue protein) in 4 different mouse tissues (colon, bone marrow, liver, lung) across time following IP injection of SW033291 at 10 mg/kg. Blue bar represents baseline at time 0, and red bars represent time course of PGE2 concentration from 1-12 hours following SW033291 injection. FIG. 10(B) shows time course of PGE2 in control mice injected with vehicle only.

FIG. 11 shows a schema of an experiment in which mice are lethally irradiated (IR) and 12 hours later receive a transplant (BMT) with CFSE dye labeled bone marrow cells (BM), and the numbers of transplanted cells that home and survive in the bone marrow of the recipient mice are then determined by FACS at 16 hours post-transplant. In different arms of the experiment mice are treated with vehicle, with SW033291 (10 mg/kg IP), or with SW033291 (10 mg/kg IP) plus Indomethacin. Drugs are administered following radiation, following the transplant, and again at 8 hours after the transplant.

Figure 12:
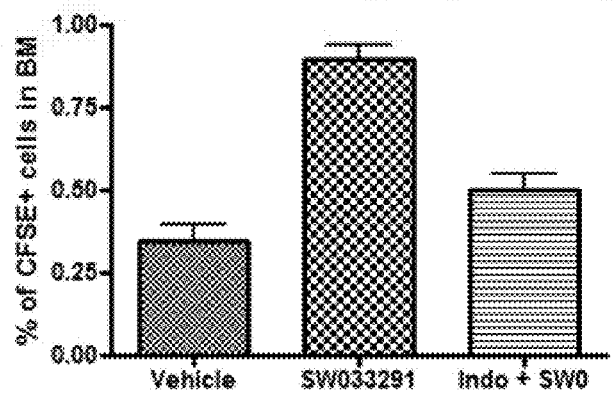
FIG. 12 illustrates a graph showing the percent of CFSE dye labeled cells that have homed to the bone marrow of mice treated as illustrated in FIG. 11.

FIG. 12 shows a graph illustrating the percent of CFSE dye labeled cells that have homed to the bone marrow of mice treated as per the schema described in FIG. 11. Treating mice with SW033291 concurrent with and following the bone marrow transplant increases numbers of homed cells in the recipient mouse bone marrow 3-fold. The figure further shows that the effect of SW033291 is near completely blocked by indomethacin (Indo+SW0), an inhibitor of COX enzymes that produce prostaglandins. This is consistent with the effect of SW033291 being mediated through the inhibition of 15-PGDH and through the resulting increase in tissue prostaglandins.

Figure 13:
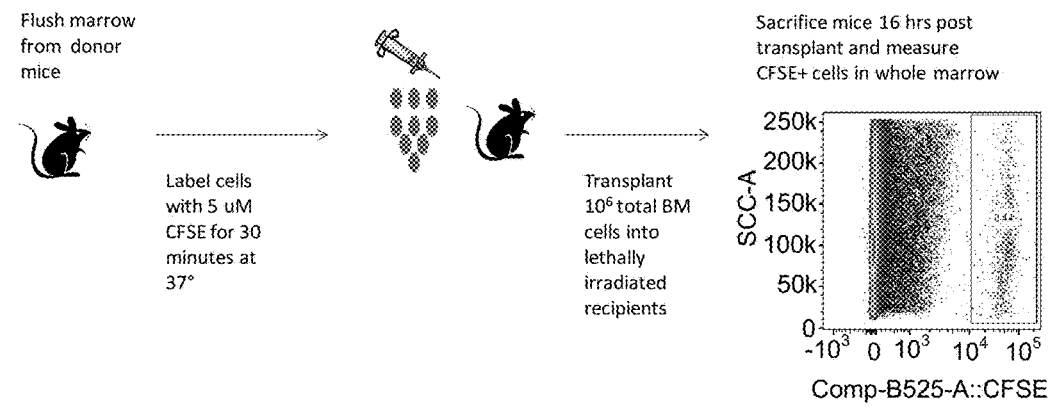
FIG. 13 is a schematic illustration showing an experiment in which mice are lethally irradiated (IR) and 12 hours later receive a transplant (BMT) with CFSE dye labeled bone marrow cells (BM), and numbers of transplanted cells that home and survive in the bone marrow of the recipient mice are then determined by FACS at 16 hours post-transplant.

FIG. 13 shows a schema of an experiment in which mice are lethally irradiated (IR) and 12 hours later receive a transplant (BMT) with CFSE dye labeled bone marrow cells (BM), and numbers of transplanted cells that home and survive in the bone marrow of the recipient mice are then determined by FACS at 16 hours post-transplant. In different arms of the experiment mice are treated with vehicle, with SW033291 (10 mg/kg IP), with SW033291 (10 mg/kg IP) plus an antagonist of PGE2 receptor EP2 (PF-04418948), or with SW033291 (10 mg/kg IP) plus an antagonist of PGE2 receptor EP4 (L-161,982). Drugs are administered following radiation, following the transplant, and again at 8 hours after the transplant.

Figure 14:
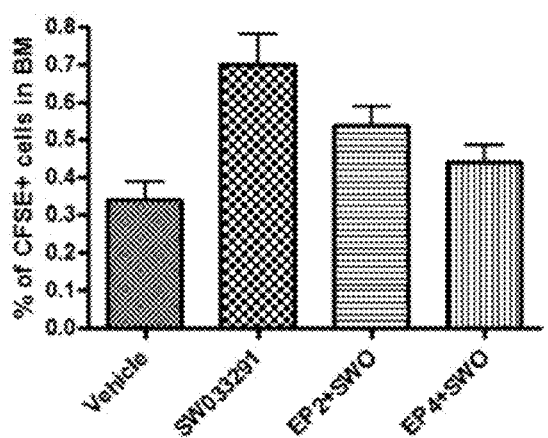
FIG. 14 illustrates a graph showing the percent of CFSE dye labeled cells that have homed to the bone marrow of mice treated as illustrated in FIG. 13.

FIG. 14 shows a graph illustrating the percent of CFSE dye labeled cells that have homed to the bone marrow of mice treated as per the schema described in FIG. 13. Treating mice with SW033291 concurrent with and following the bone marrow transplant increases numbers of homed cells in the recipient mouse bone marrow 2-fold. The figure further shows that the effect of SW033291 is near completely blocked by an antagonist to the EP4 receptor (EP4+SW0), and is partially blocked by an antagonist of the EP2 receptor (EP2+SW0). This is consistent with the effect of SW033291 being mediated through the inhibition of 15-PGDH and through the resulting increase of tissue prostaglandins, including PGE2.

In another experiment, mice were injected with SW033291 twice daily IP at 10 mg/kg for 5 doses. 2 hours following the last dose bone marrow is harvested and sorted into SKL marked cells that are hematopoietic stem cell enriched and into CD45 (−) cells that are bone marrow stroma cells. RNA was extracted and gene expression determined relative to levels in mice injected with vehicle control.

FIGS. 15(A-B) show graph illustrating induction of gene expression in bone marrow SKL cells and bone marrow stromal cells of SW033291 treated mice. Mice administered SW033291 show a 3 fold induction in RNA expression of CXCL12 and SCF in bone marrow SKL cells, and show a greater than 4-fold induction of CXCL12 and SCF in CD45(−) bone marrow stromal cells.

Figure 16:
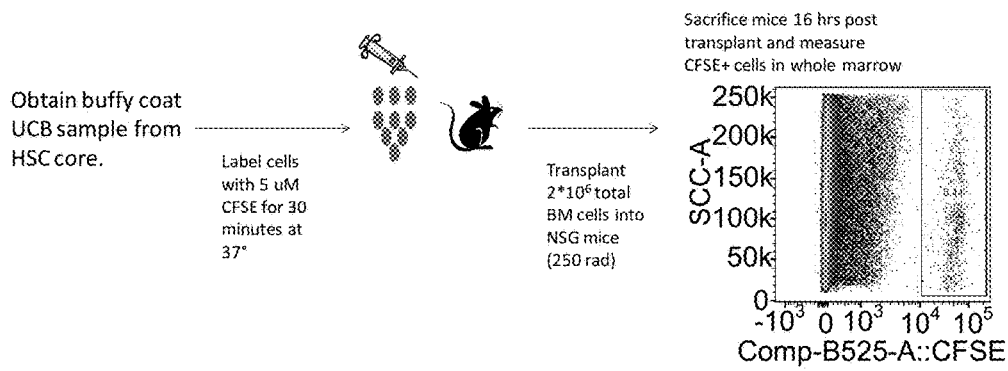
FIG. 16 is a schematic illustration showing an experiment in which immune deficient NSG mice are lethally irradiated (IR) and 12 hours later receive a transplant with CFSE dye labeled buffy coat cells from human umbilical cord blood (UCB), and number of transplanted cells that home and survive in the bone marrow of the recipient mice are then determined by FACS at 16 hours post-transplant.

FIG. 16 illustrates a schema of an experiment in which immune deficient NSG mice are lethally irradiated (IR) and 12 hours later receive a transplant with CFSE dye labeled buffy coat cells from human umbilical cord blood (UCB), and number of transplanted cells that home and survive in the bone marrow of the recipient mice are then determined by FACS at 16 hours post-transplant. In different arms of the experiment mice are treated with vehicle or with SW033291. Drugs are administered following radiation, following the transplant, and again at 8 hours after the transplant.

Figure 17:
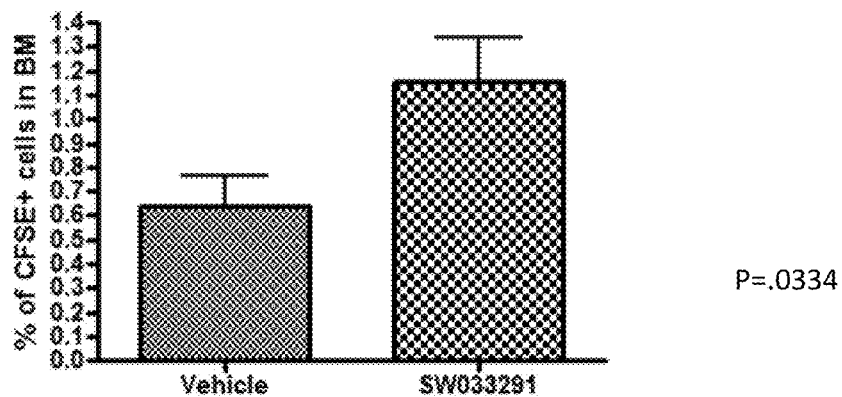
FIG. 17 illustrates a graph showing the percent of CFSE dye labeled human umbilical cord buffy coat cells that have homed to the bone marrow of mice treated as per the schema above.
Figure 18:
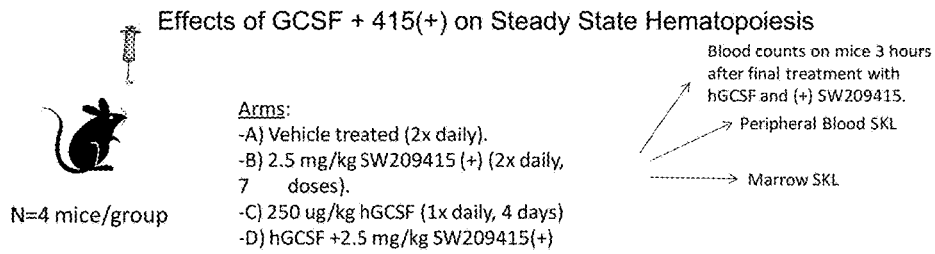
FIG. 18 illustrates a schematic diagram showing the design of a study in which 4 groups of mice (4 mice per group) were administered either A) vehicle control; B) 2.5 mg/kg of 15-PGDH inhibitor (+) SW209415 twice daily IP for 7 doses; c) recombinant human G-CSF 250 μg/kg subcutaneously once daily for 4 doses or d) the combination of 2.5 mg/kg of 15-PGDH inhibitor (+) SW209415 twice daily IP for 7 doses plus recombinant human G-CSF 250 μg/kg subcutaneously once daily for 4 doses (with the daily dose of G-CSF being administered coincident with a dose of (+) SW209415).

FIG. 17 illustrates a graph showing the percent of CFSE dye labeled human umbilical cord buffy coat cells that have homed to the bone marrow of mice treated as per the schema described in FIG. 18. Treating mice with SW033291 at the time of and following the transplant with buffy coat from human umbilical cord blood (UCB) increases numbers of homed human cells in the recipient mouse bone marrow nearly 2-fold.

Example 3

FIG. 18 shows the design of a study in which 4 groups of mice (4 mice per group) were administered either;
a) vehicle control,
b) 2.5 mg/kg of 15-PGDH inhibitor (+) SW209415 twice daily IP for 7 doses,
c) recombinant human G-CSF 250 ug/kg subcutaneously once daily for 4 doses
d) the combination of 2.5 mg/kg of 15-PGDH inhibitor (+) SW209415 twice daily IP for 7 doses plus recombinant human G-CSF 250 ug/kg subcutaneously once daily for 4 doses (with the daily dose of G-CSF being administered coincident with a dose of (+) SW209415) 3 hours following the last drug dose mice were sacrificed for analysis.

Figure 19:
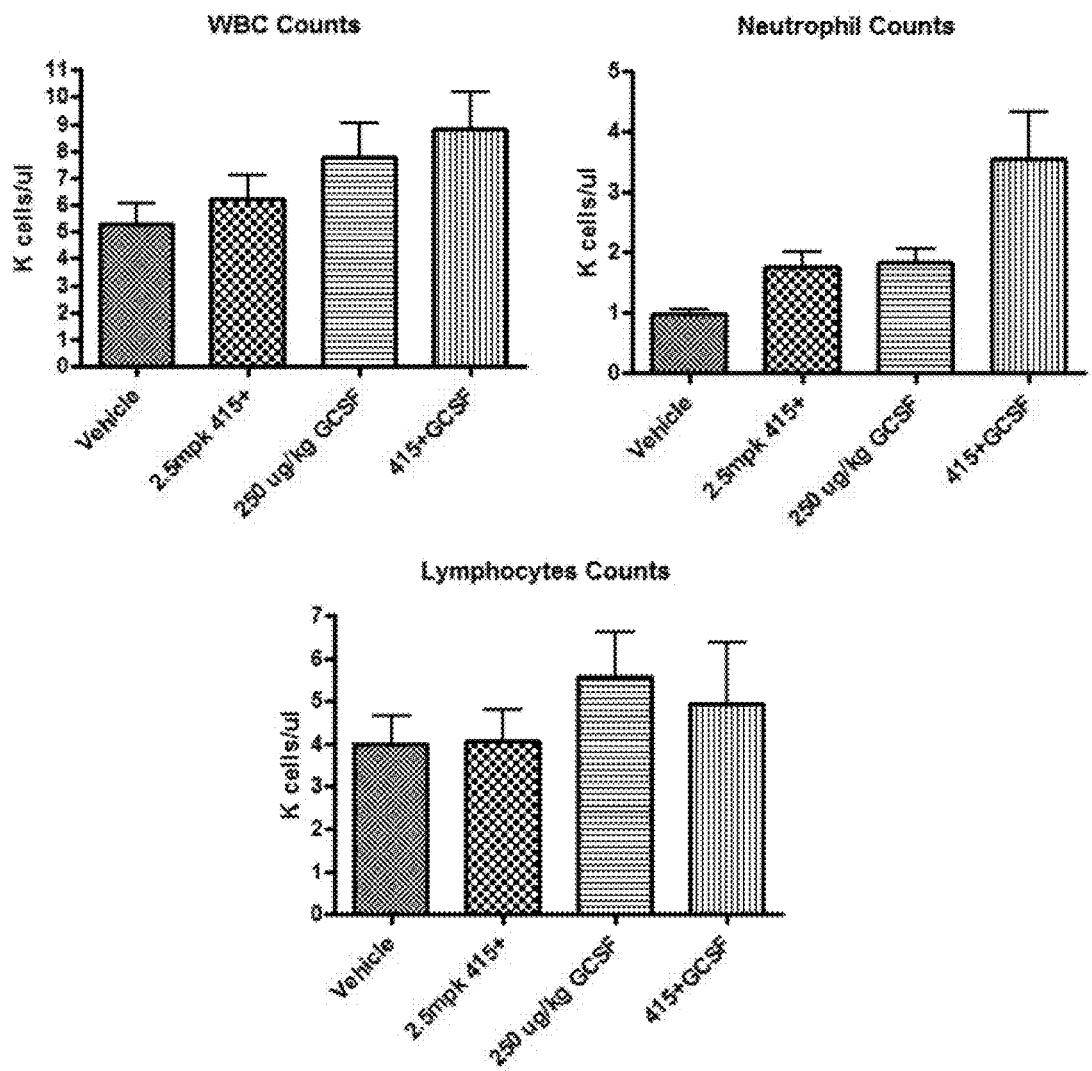
FIG. 19 illustrates graphs showing total counts of white blood cells, neutrophils, and lymphocytes of mice administered 15-PGDH inhibitor (+) SW209415 and/or G-CSF as described in FIG. 18.

FIG. 19 shows results in each arm for measurement of total white cells, neutrophils, and lymphocytes.

Neutrophil counts approximately double following administration of G-CSF, approximately doubled following administration of (+) SW209415, and increased 3 to 4-fold after administration of the combination of G-CSF plus (+) SW209415.

FIG. 20 shows results in each arm for measurement of red cells, hematocrit, hemoglobin, and platelets.

Figure 21:
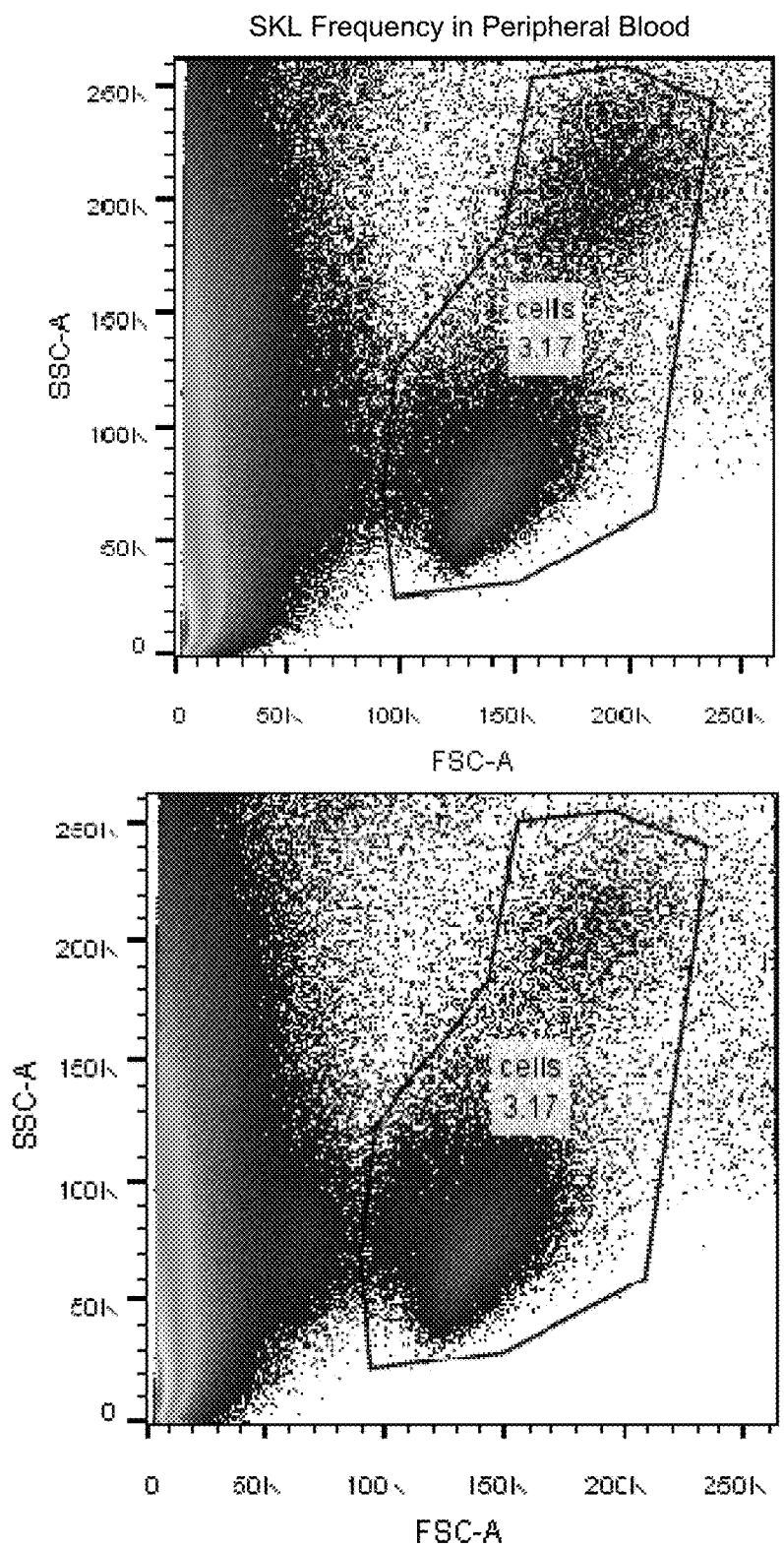
FIG. 21 illustrates graphs showing the percent and number of circulating SKL (Sca-1+; C-kit+; Lin−) marked cells in peripheral blood of mice administered 15-PGDH inhibitor (+) SW209415 and/or G-CSF as described in FIG. 18.
Figure 21:
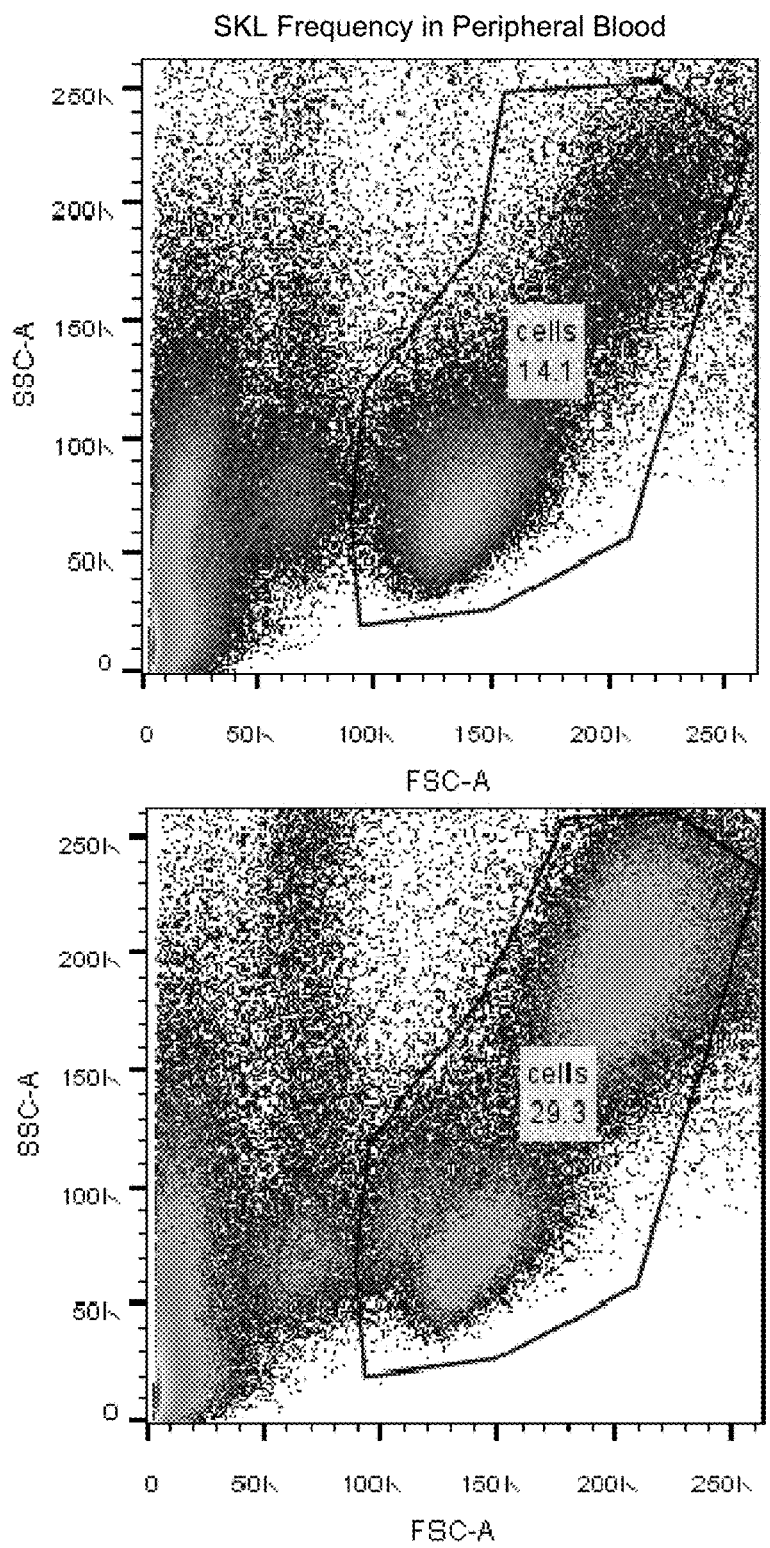
Figure 21:
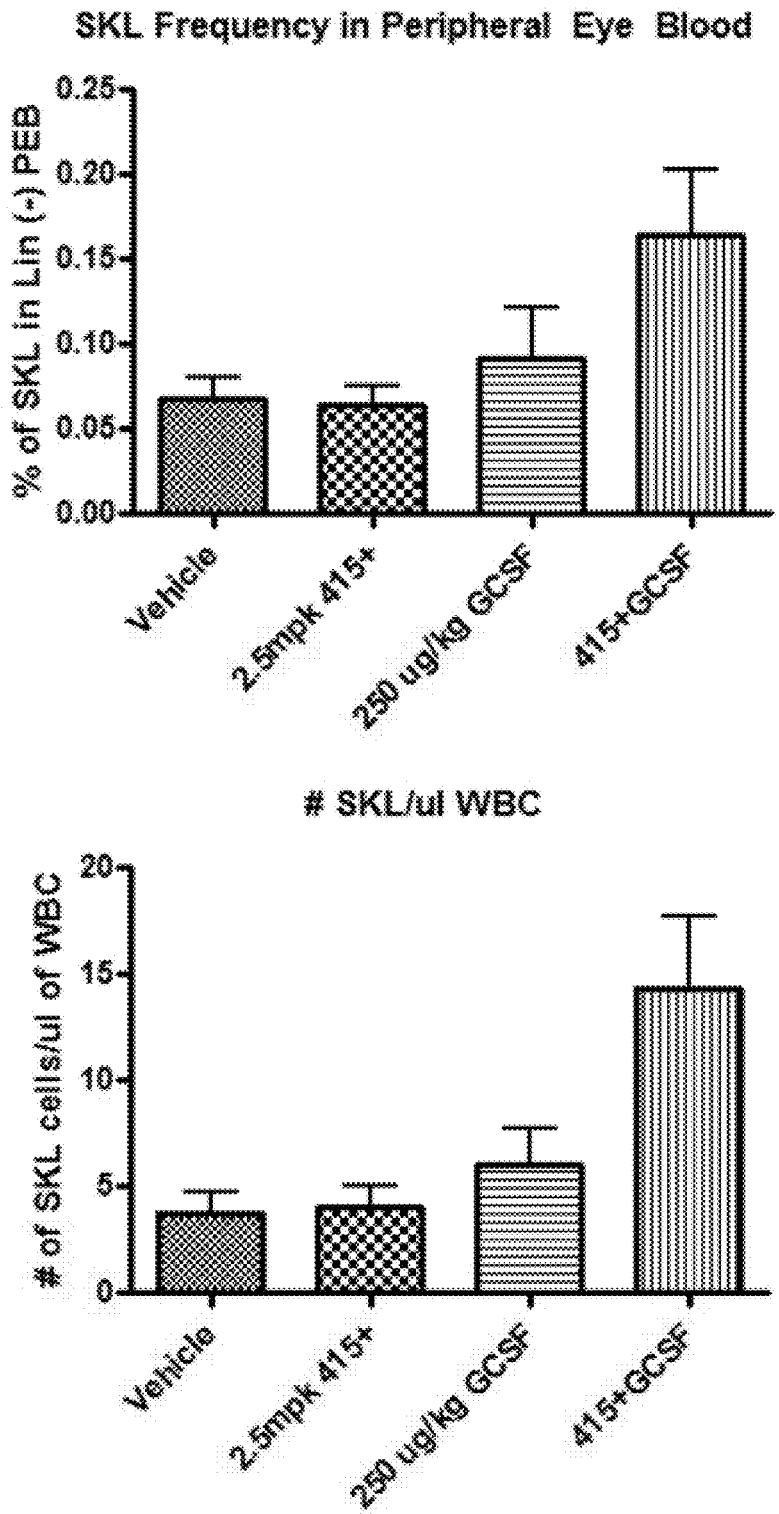

FIG. 21 shows results in each arm for measurement in peripheral blood of circulating SKL (Sca-1+; C-kit+; Lin−) marked cells that are enriched for hematopoietic stem cells. The results show first that in this study G-CSF increased the frequency of peripheral blood SKL cells (in Lin− cells) by 33%. (+) SW209415 when administered alone showed no effect on frequency of peripheral blood stem cells. However, the combination of G-CSF plus (+) SW209415 increased by 2 to 3-fold the frequency of peripheral blood SKL cells (in Lin− cells). This result understates the absolute magnitude of this effect, as the combination of G-SCF plus (+) SW209415 also increases the total white count, and hence the absolute number of the Lin− population. Thus, G-CSF increased the number of peripheral blood SKL cells by approximately 50%. (+) SW209415 when administered alone showed no effect on number of peripheral blood stem cells. However, the combination of G-CSF plus (+) SW209415 increased the number of peripheral blood SKL cells by approximately 3.5-fold, showing a marked increased effect of the combination.

Figure 22:
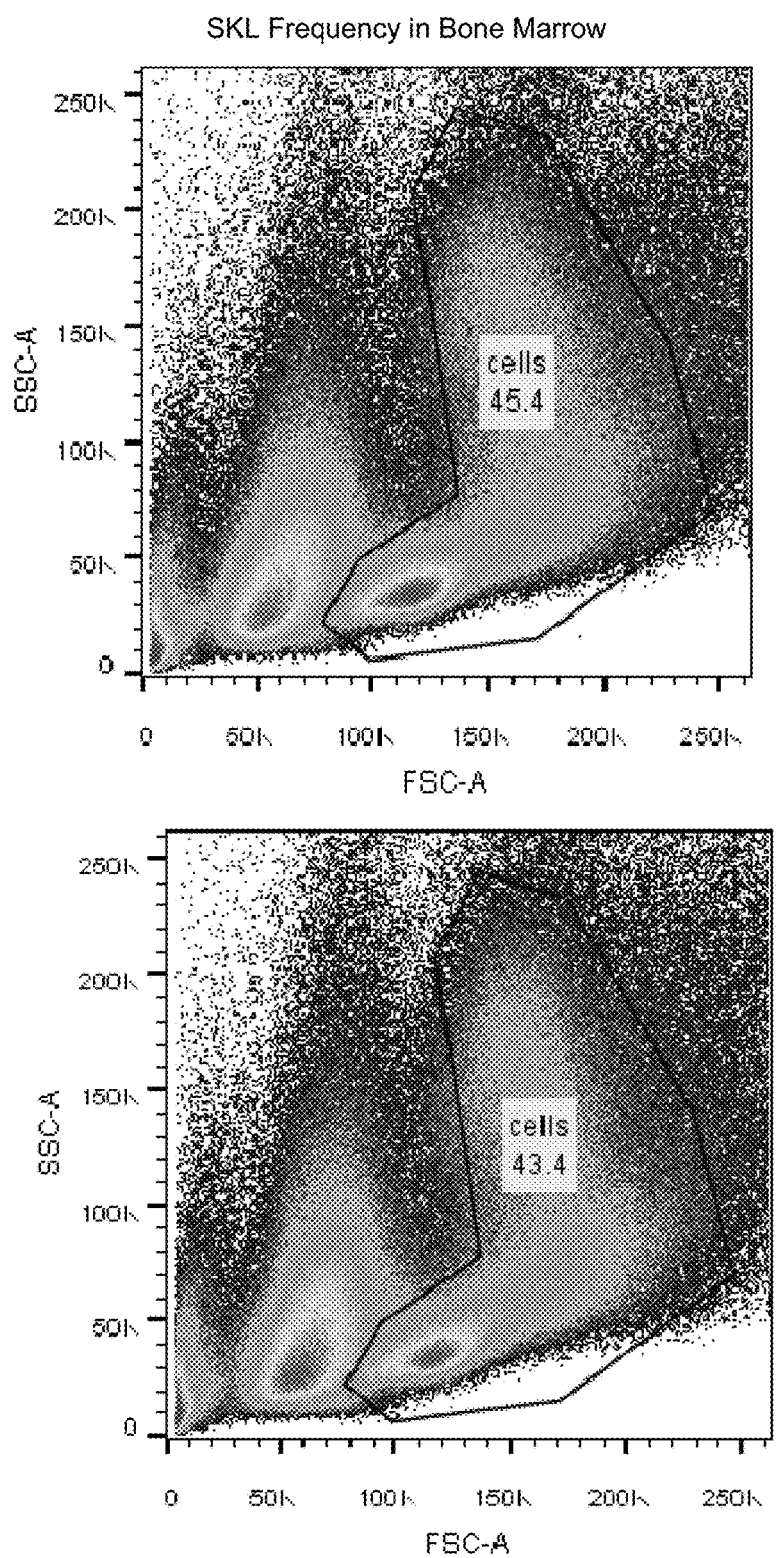
FIG. 22 illustrates graphs showing the percent and number of SKL (Sca-1+; C-kit+; Lin−) marked cells in bone marrow of mice administered 15-PGDH inhibitor (+) SW209415 and/or G-CSF as described in FIG. 18.
Figure 22:
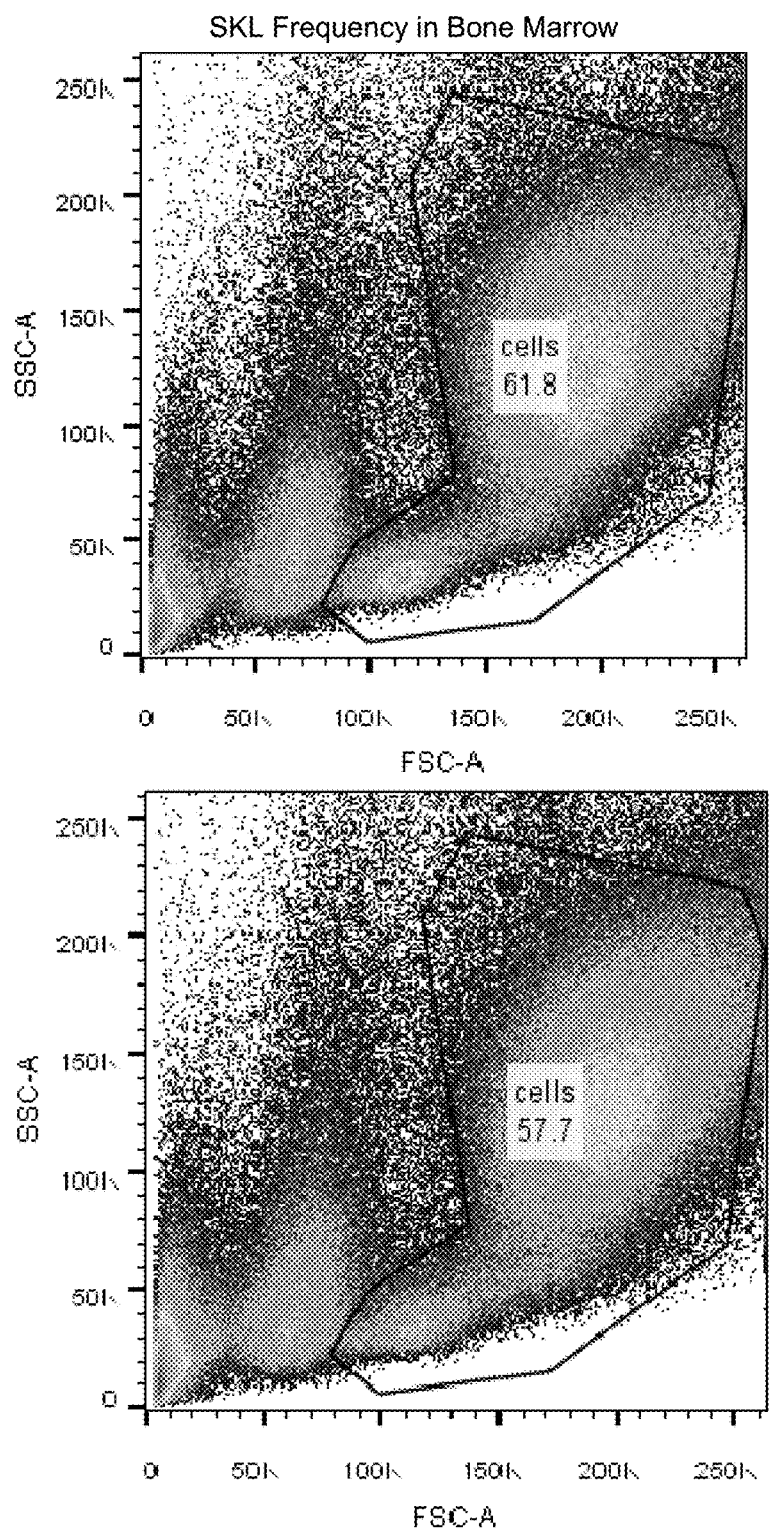
Figure 23A:
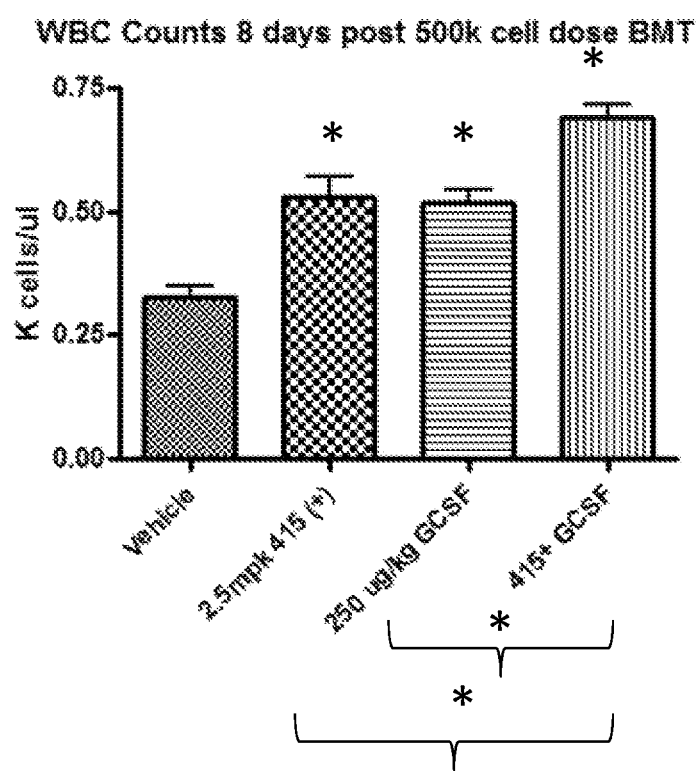
FIGS. 23(A-G) illustrate graphs showing (A) WBC counts, (B) neutrophil counts, (C) lymphocyte counts, (D) RBC counts, (E) hemoglobin counts, (F) hematocrit counts, and (G) platelet counts in peripheral blood of recipient mice lethally irradiated followed by bone marrow transplantation (BMT) treated with vehicle, G-CSF, SW209415, and SW209415 in combination with G-CSF at day 8 following BMT.
Figure 23B:
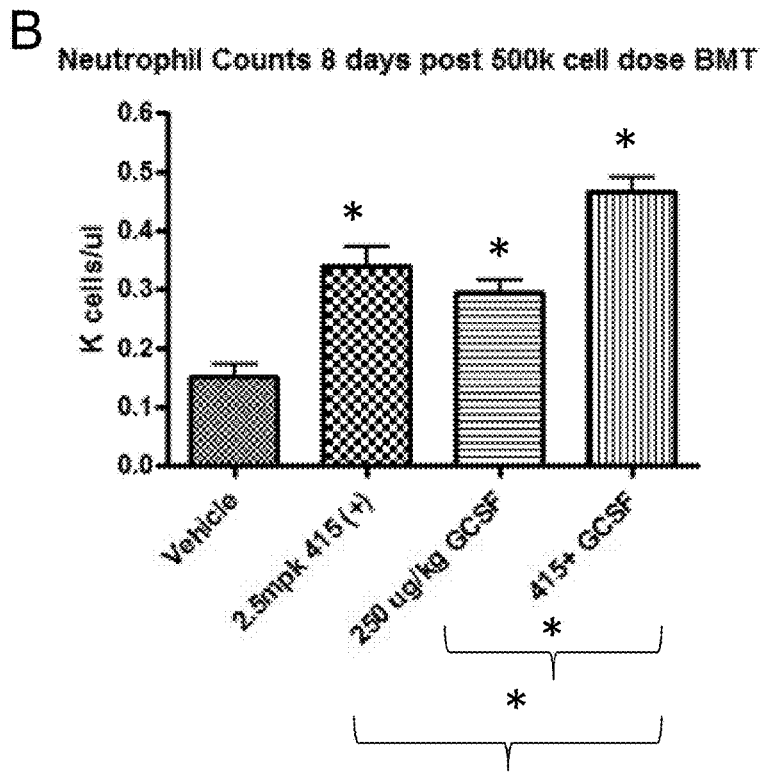
Figure 23C:
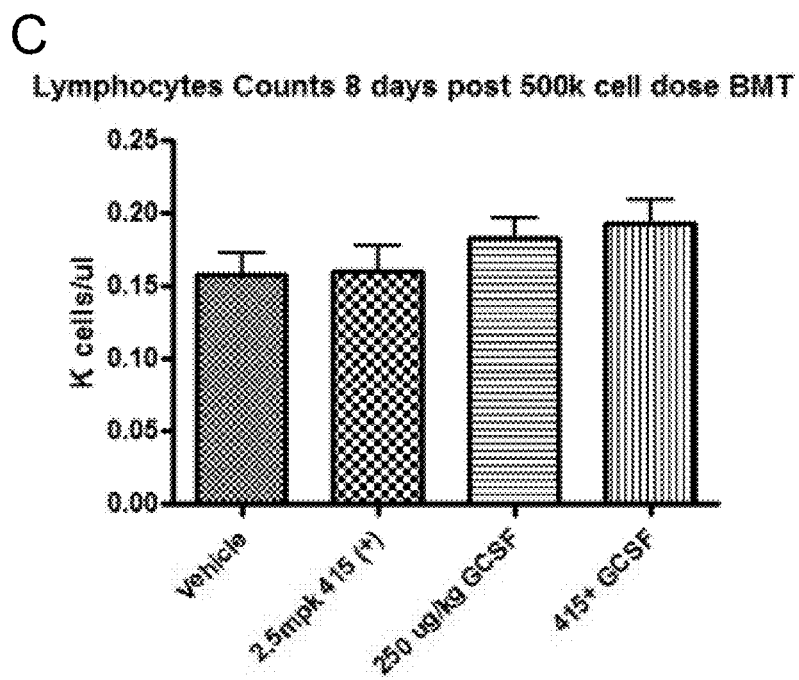
Figure 23D:
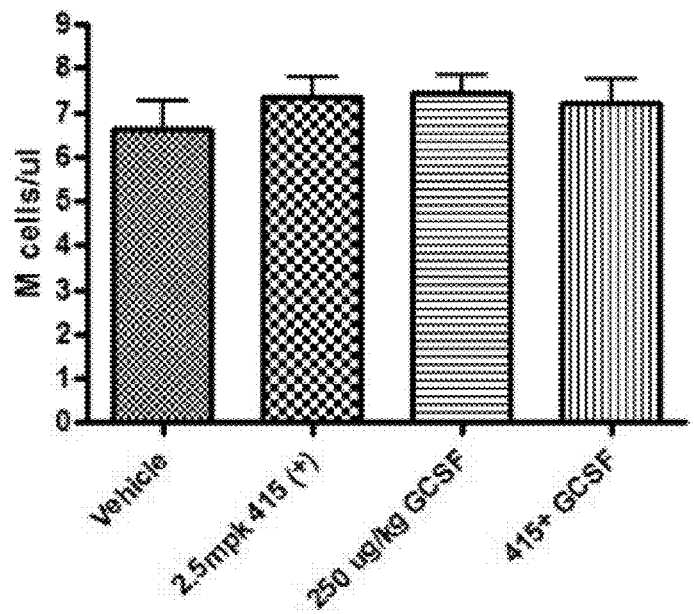
Figure 23E:
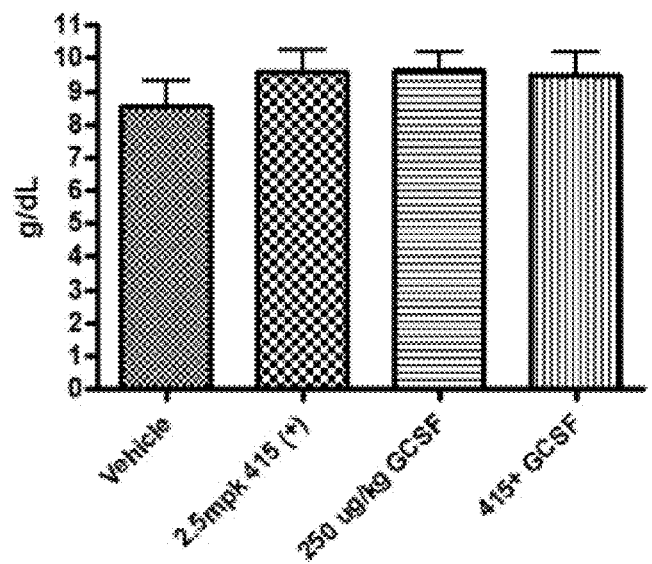
Figure 23F:
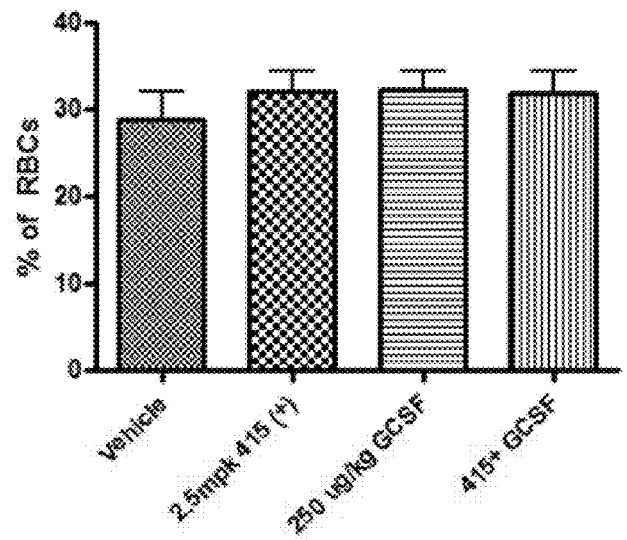
Figure 23G:
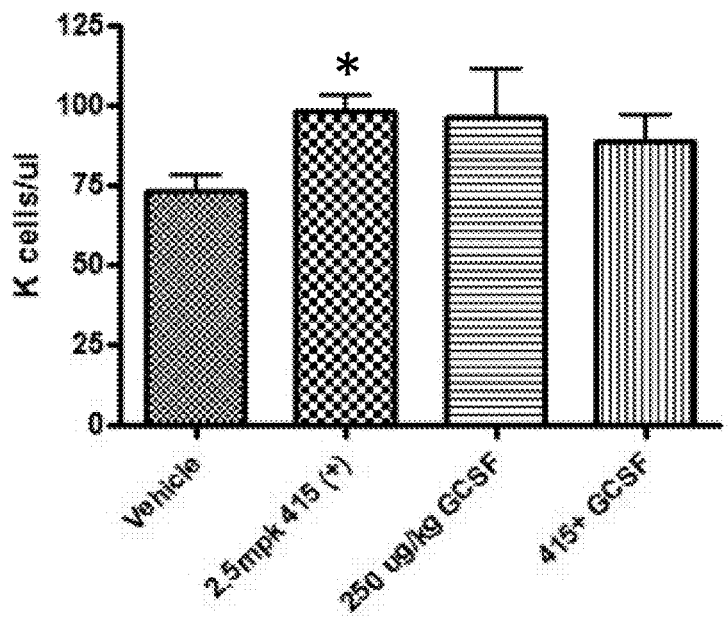
Figure 24A:
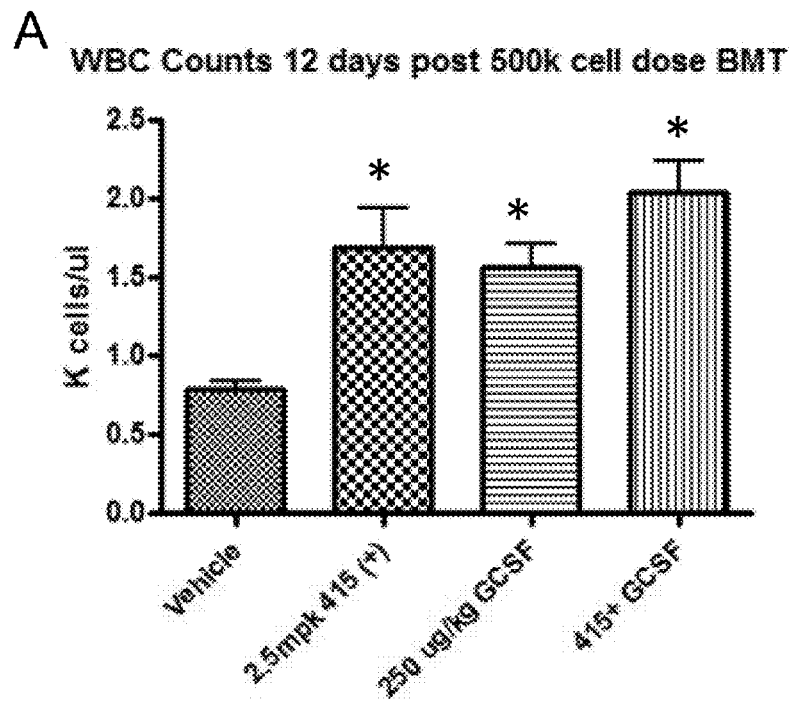
FIGS. 24(A-G) illustrate graphs showing (A) WBC counts, (B) neutrophil counts, (C) lymphocyte counts, (D) RBC counts, (E) hemoglobin counts, (F) hematocrit counts, and (G) platelet counts in peripheral blood of recipient mice lethally irradiated followed by bone marrow transplantation (BMT) treated with vehicle, G-CSF, SW209415, and SW209415 in combination with G-CSF at day 12 following BMT.
Figure 24B:
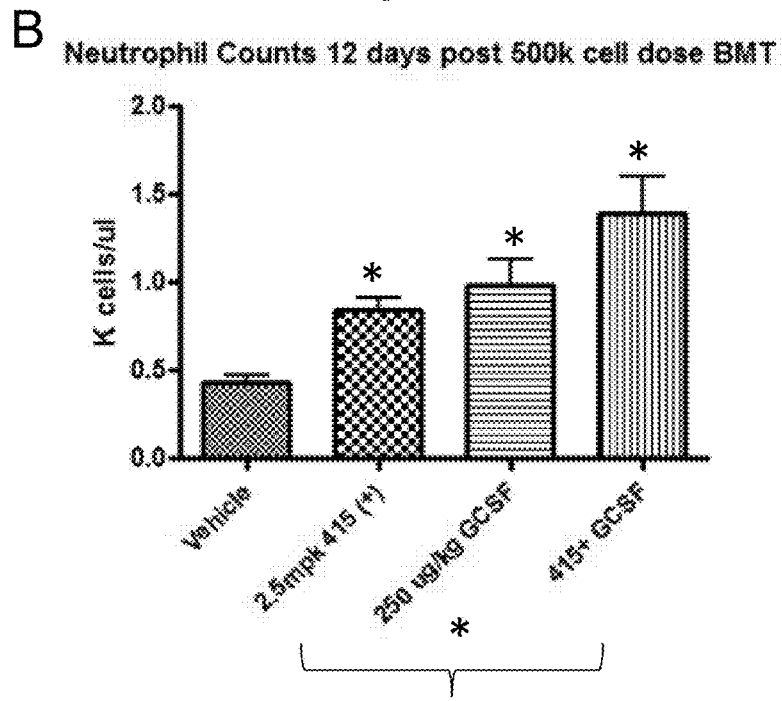
Figure 24C:
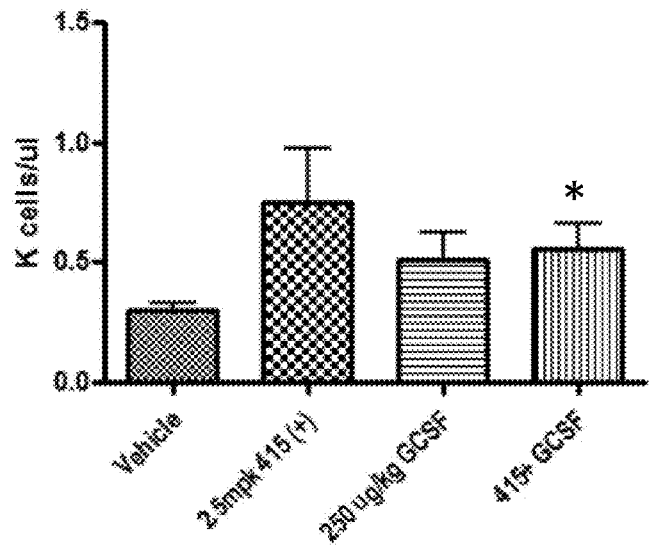
Figure 24D:
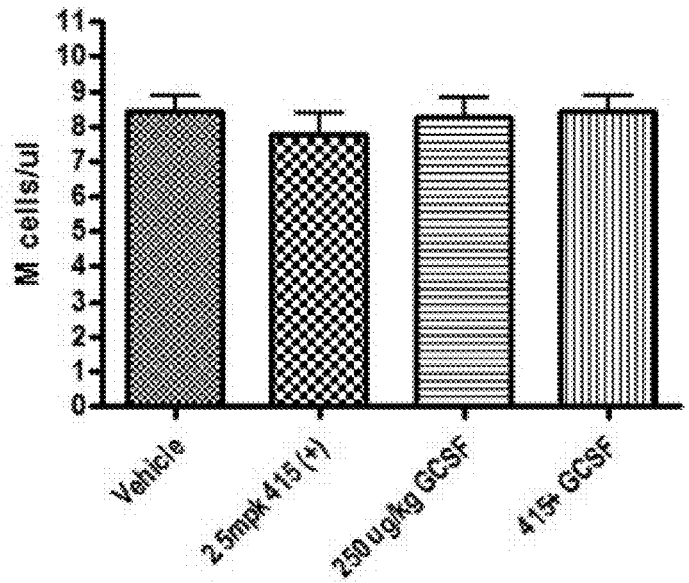
Figure 24E:
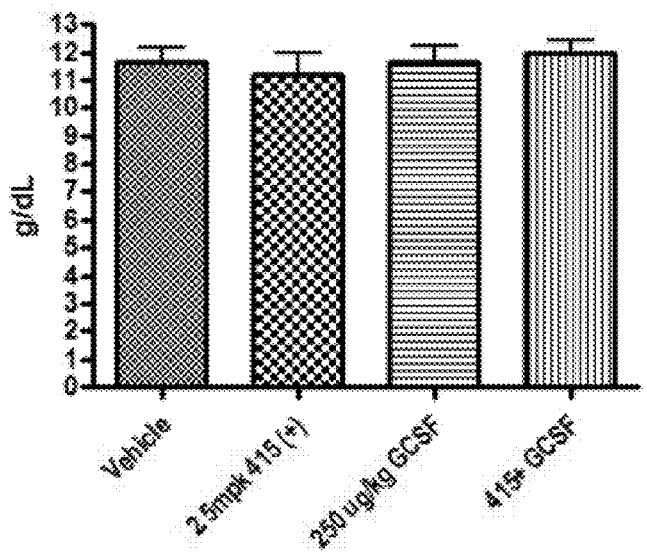
Figure 24F:
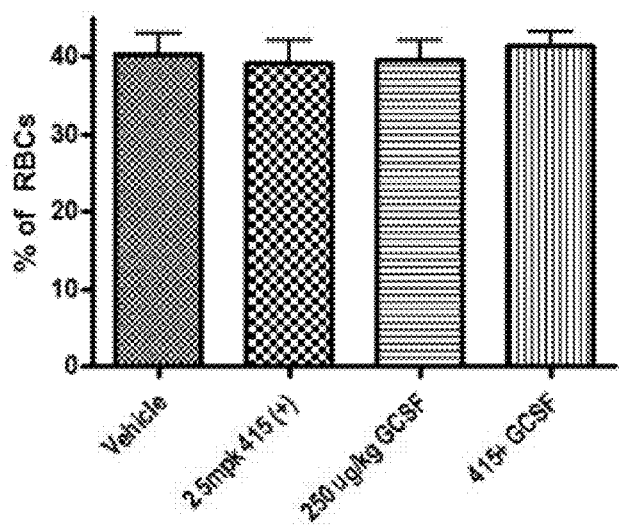
Figure 24G:
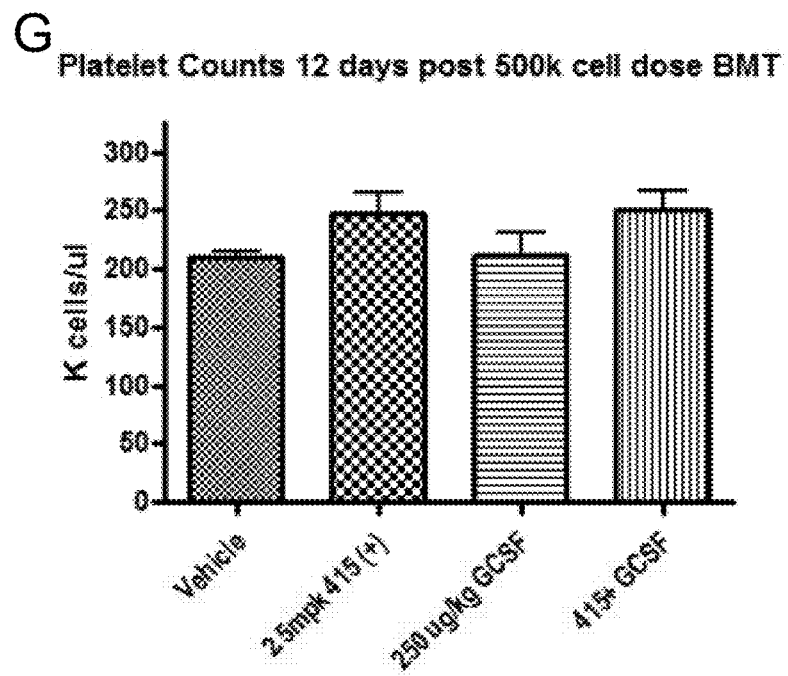
Figure 25A:
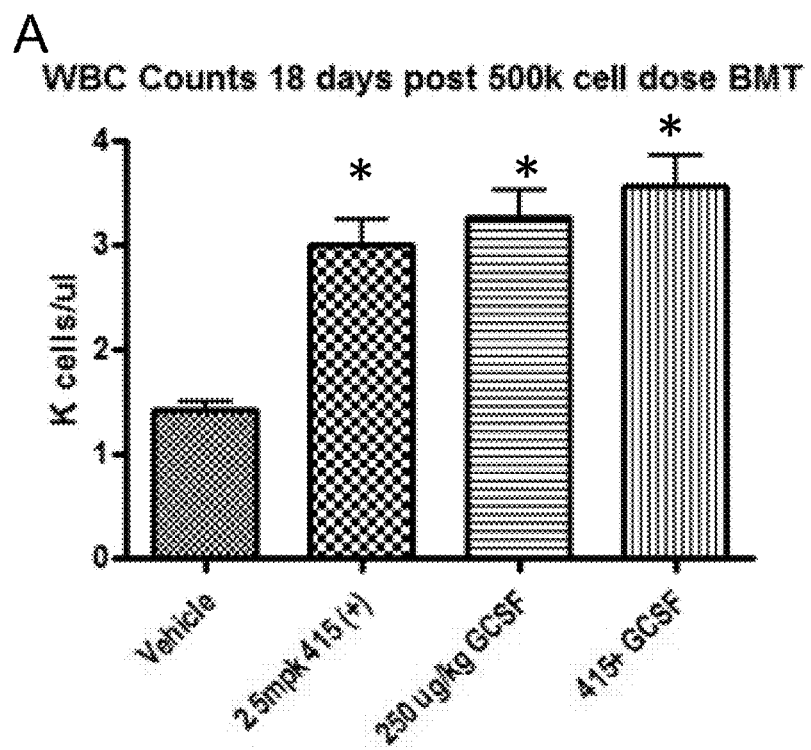
FIGS. 25(A-G) illustrate graphs showing (A) WBC counts, (B) neutrophil counts, (C) lymphocyte counts, (D) RBC counts, (E) hemoglobin counts, (F) hematocrit counts, and (G) platelet counts in peripheral blood of recipient mice lethally irradiated followed by bone marrow transplantation (BMT) treated with vehicle, G-CSF, SW209415, and SW209415 in combination with G-CSF at day 18 following BMT.
Figure 25B:
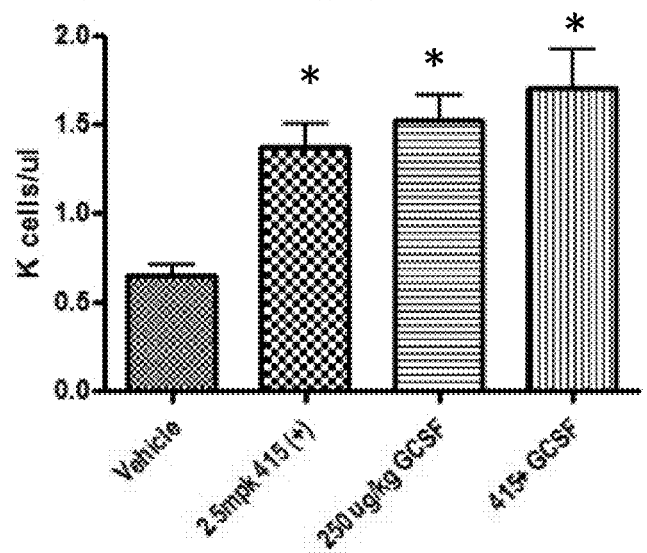
Figure 25C:
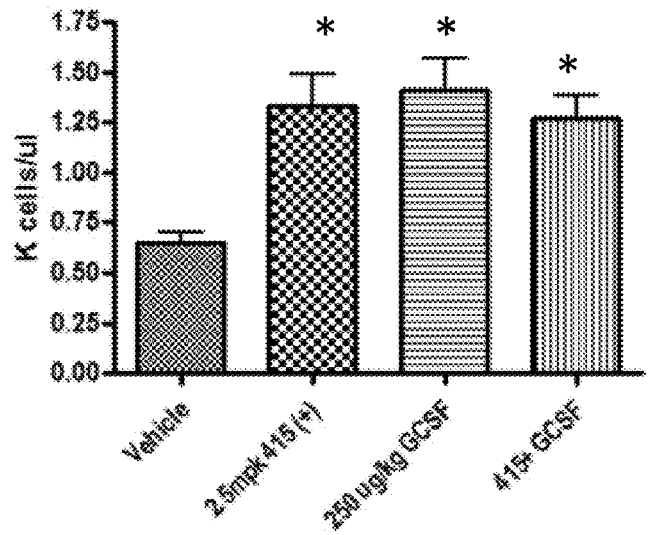
Figure 25D:
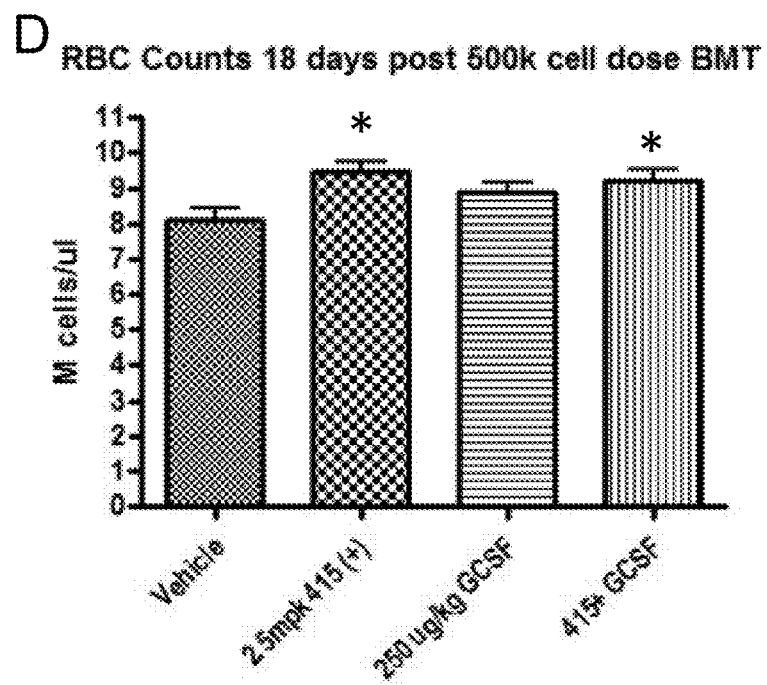
Figure 25E:
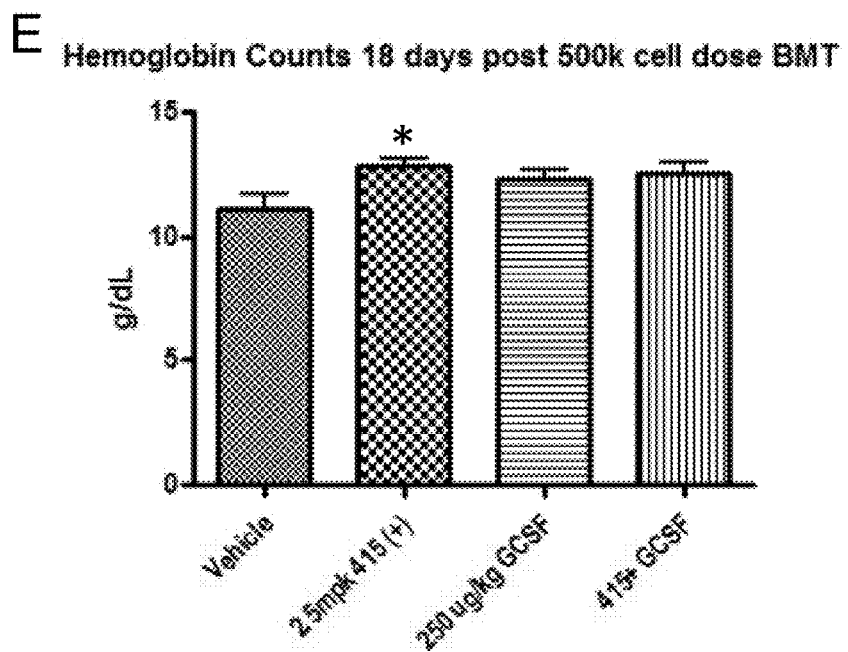
Figure 25F:
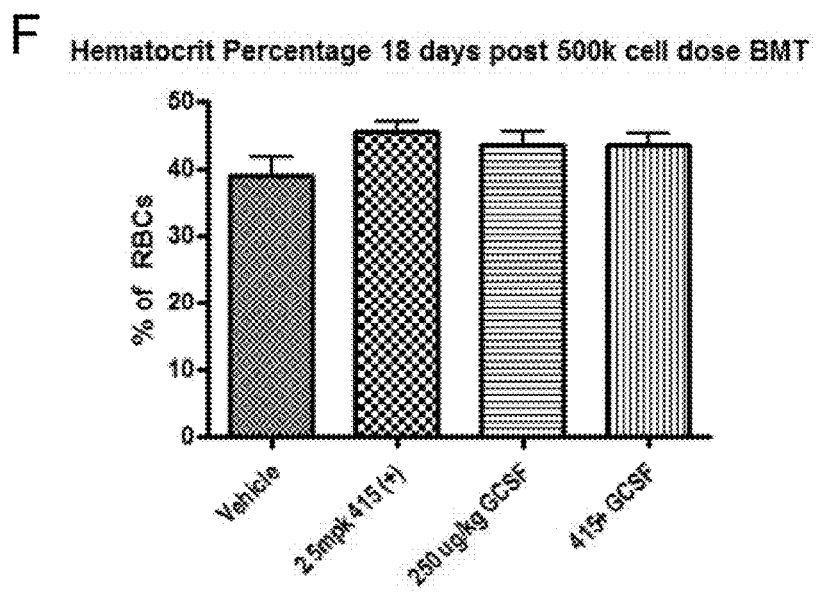
Figure 25G:
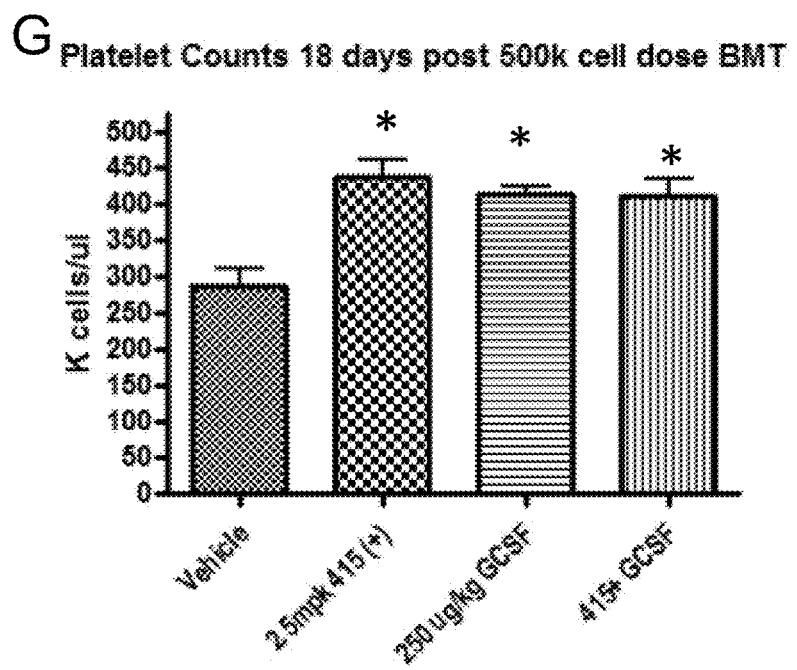

FIG. 22 shows results in each arm for measurement of SKL cells in mice bone marrow. The show that bone marrow SKL marked cells are increased by (+) SW209415, further increased by G-CSF, and further increased by the combination of (+) SW209415 plus G-CSF.

Example 4

In this Example, recipient mice lethally irradiated (11 Gy) followed by BMT (500 k total cells) 16 hours post IR were administered either:
a) Vehicle treated (2× daily).
b) 250 μg/kg GCSF (1× daily, subcutaneous administration, starting 24 hours post BMT)
c) 2.5 mg/kg SW209415 (+) (2× daily, 18 days, starting post IR).
d) 250 μg/kg hGCSF (lx daily, 17 days)+2.5 mg/kg SW209415(+) (2× daily, 18 days).

Figure 26A:
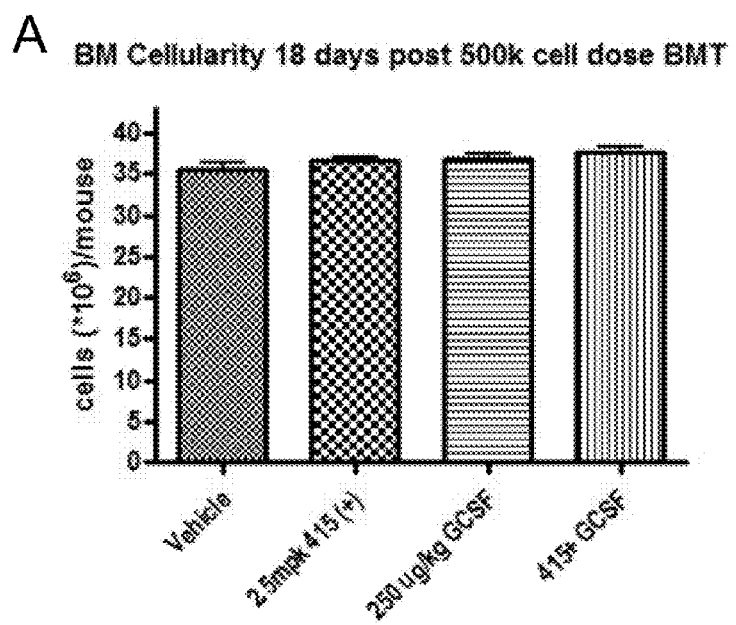
FIGS. 26(A-C) illustrate graphs showing (A) BM cellularity 18 days post 500 k cell does BMY, (B) SKL levels 18 days post 500 k cell dose BMT, and (C) SKL/mouse 18 days post 500 k cell dose BMT treated with vehicle, G-CSF, SW209415, and SW209415 in combination with G-CSF at day 18 following BMT.
Figure 26B:
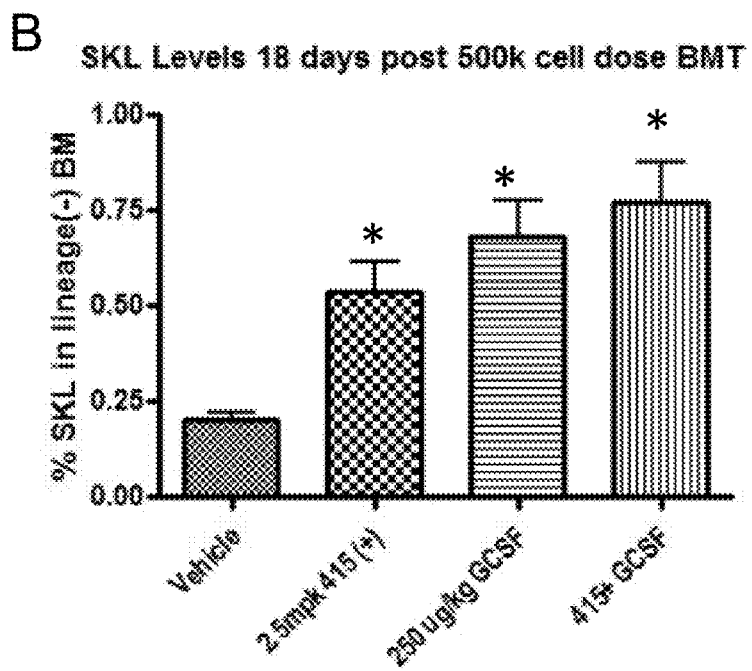
Figure 26C:
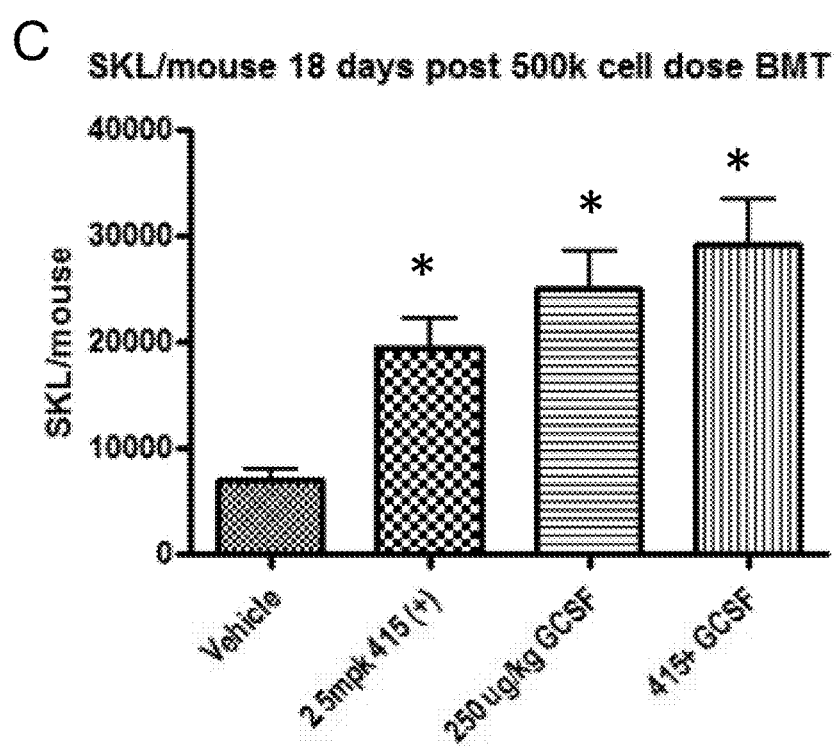

Mice were bled via submandibular vein at days 8, 12, and 18 post transplant for CBC using the Hemavet 850 fs and sacrificed at day 18 to assess marrow cellularity and SKL frequency. Blood counts were tabulated graphically as illustrated in FIGS. 24-26 with error bars corresponding to standard error of the means and compared using 2-tailed t-tests.

SW209415 is Synergistic with GCSF in Promoting Hematopoietic Recovery after BMT

Granulocyte colony stimulating factor (G-CSF, clinical names Lenograstim and Filgrastim) is an FDA approved glycoprotein used both pre-transplantation for stem cell priming purposes, and post transplantation to enhance stem cell engraftment and minimize mortality associated with prolonged neutropenia. Its use has been shown to accelerate granulocyte engraftment by 1-6 days following BMT compared to control. G-CSF occurs naturally and is responsible for mounting the neutrophil activation in response to stress or infection by binding to its receptor G-CSFR. Several tissues can produce G-CSF upon stimulation by inflammatory mediators such as LPS, TNF-α, and IL-17, resulting in G-CSF release into the bloodstream which stimulates neutrophil production within, and mobilization from the bone marrow. In addition to neutrophil mobilization, G-CSF has been implication in mobilizing HSCs from marrow.

The use of SW209415 clinically in recipients of BMT would need validation in clinical models in comparison and in combination with GCSF. To determine SW209415's ability to promote hematopoietic recovery following BMT independently as well as synergistically with GCSF, we established the bone marrow transplant model described above in which recipient mice receiving 500 k total bone marrow cells were assessed for peripheral blood recovery at 3 time points post transplant. FIGS. 23-26 show that compared to vehicle treatment, W209415, GCSF, and the combination treatment recovered neutrophils significantly faster at Days 8, 12, and 18 post BMT, but that the combination treatment demonstrated a synergistic effect. Neutrophil counts at Day 8-150 (Veh), 339(415), 295(GCSF), 466-(4+G), Day 12-427(Veh) 839 (415), 982 (GCSF), 1390 (4+G), and Day 18-649 (Veh), 1370 (415), 1518 (GCSF), 1703 (4+G) all demonstrated an enhanced effect when the agents were used in combination, showing the two compounds promote recovery via independent mechanisms. Additionally we showed the frequency of SKL cells (enriched for true HSCs) was higher in the combination treated group compared to either therapeutic alone.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

The following is claimed:

1. A method of increasing neutrophils in a subject in need thereof, the method comprising administering to the subject a 15-PGDH inhibitor, wherein the 15-PGDH inhibitor has the following formula (V):

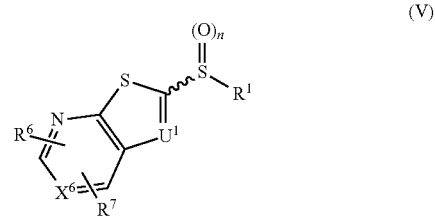

(V)

wherein n is 0-2
$X^6$ is independently N or $CR^c$
$R^1$, $R^6$, $R^7$, and $R^c$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_4$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, and phosphate esters, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}OR'$ (wherein n1=1, 2, or 3), $CF_3$, $CH_2$—$CH_2X$, $CH_2$—$CH_2$—$CH_2X$, (wherein X=H, F, Cl, Br, or I), CN, (C=O)—R', (C=O)N(R')$_2$, COOR' (wherein R' is H or a lower alkyl group), and $R^3$ or $R^4$ may be absent;

and pharmaceutically acceptable salts thereof.

2. The method of claim 1, further comprising administering in combination with the 15-PGDH inhibitor at least one hematopoietic cytokine or cell mobilization agent.

3. The method of claim 1, wherein the hematopoietic cytokine or cell mobilization agent comprises at least one of G-CSF or Plerixafor.

4. The method of claim 1, wherein the subject has or is at risk of at least one of neutropenia, thrombocytopenia, anemia, or cytopenia.

5. The method of claim 4, wherein the subject has received a hematopoietic stem cell transplant, bone marrow transplant, chemotherapy, a myelosuppressive therapy, radiation therapy, and/or viral therapy, and/or has a bone marrow disease, cancer, viral infection, aplastic anemia, myelodysplasia, and/or myelofibrosis.

6. The method of claim 1, wherein the 15-PGDH inhibitor has the following formula (VI):

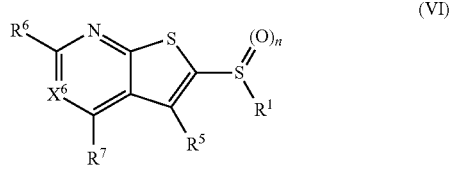

(VI)

wherein n=0-2;
$X^6$ is N or $CR^c$;
$R^1$ is selected from the group consisting of branched or linear alkyl, —$(CH_2)n_1CH_3$ ($n_1$=0-7),

wherein $n_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

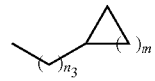

($n_3$=0-5, m=1-5), and

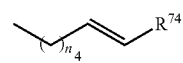

($n_4$=0-5);

$R^5$ is selected from the group consisting of H, Cl, F, $NH_2$, and $N(R^{76})_2$;

$R^6$ and $R^7$ can each independently be one of the following:

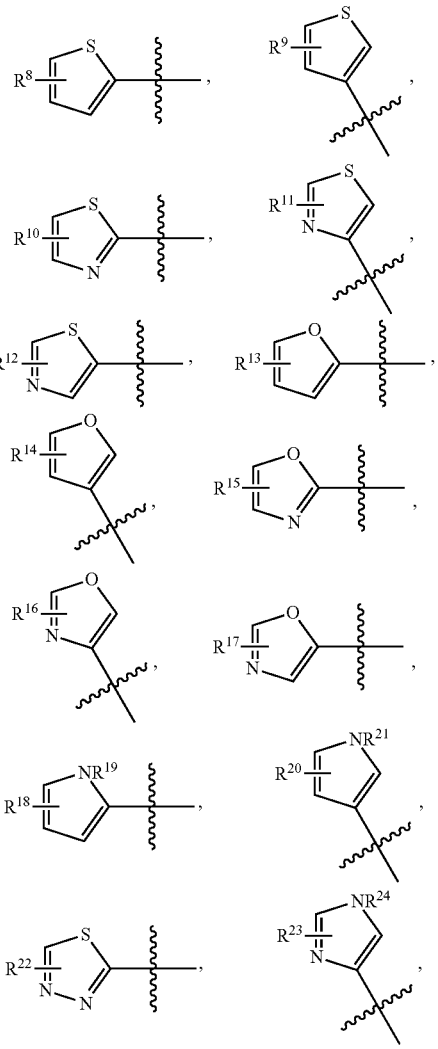

-continued

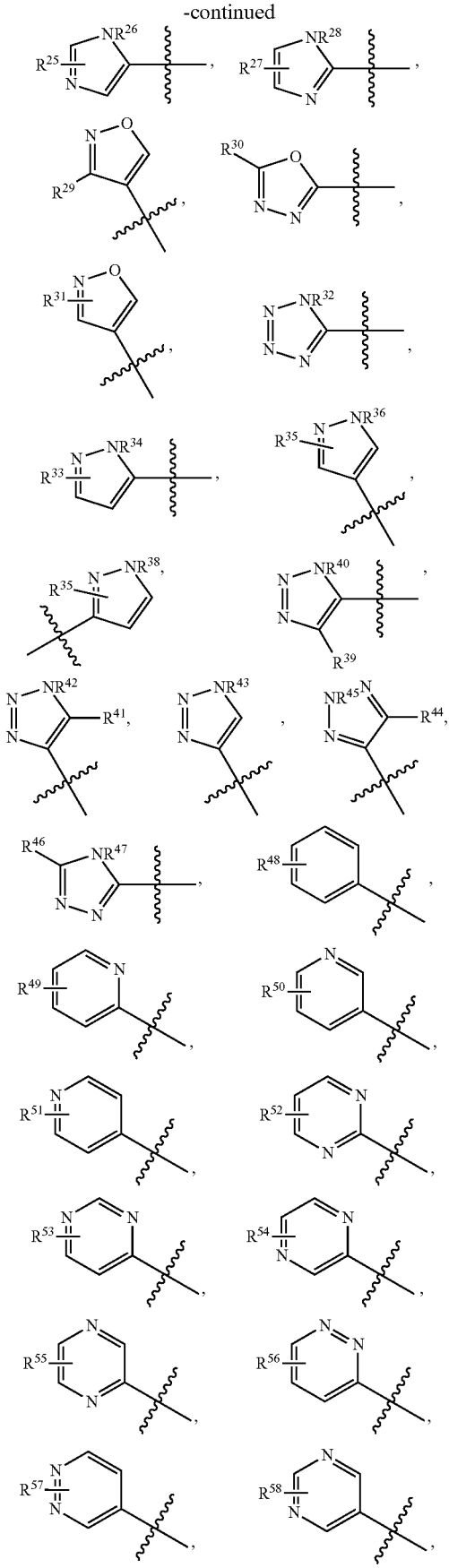

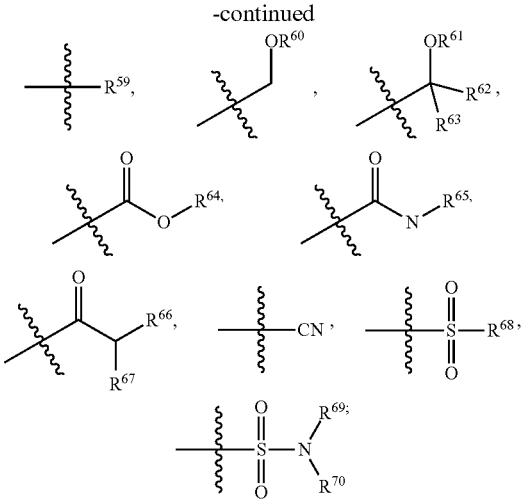

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{76}$, and $R^c$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, and pharmaceutically acceptable salts thereof.

7. The method of claim 1, wherein the 15-PGDH inhibitor has the following formula following formula:

(IX)

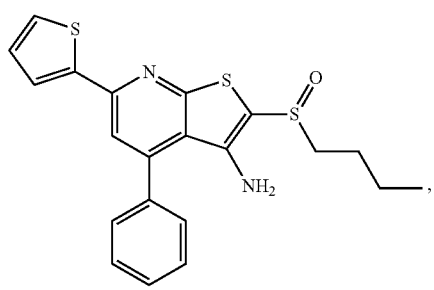

-continued

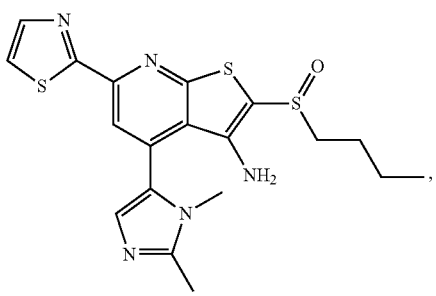

(X)

or pharmaceutically acceptable salts thereof.

8. A method increasing numbers of and/or of mobilizing peripheral blood hematopoietic stem cells in a subject in need thereof, the method comprising administering to the subject a 15-PGDH inhibitor, wherein the 15-PGDH inhibitor has the following formula (V):

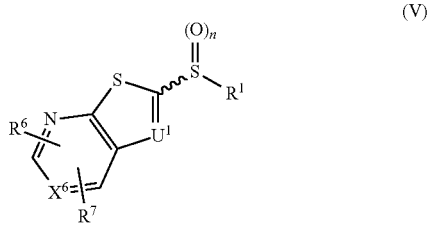

(V)

wherein n is 0-2
$X^6$ is independently is N or $CR^c$
$R^1$, $R^6$, $R^7$, and $R^c$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, and phosphate esters, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;
$U^1$ is N, C—$R^2$, or C—$NR^3R^4$, wherein $R^2$ is selected from the group consisting of a H, a lower alkyl group, O, $(CH_2)_{n1}OR'$ (wherein n1=1, 2, or 3), $CF_3$, $CH_2$—$CH_2X$, $CH_2$—$CH_2$—$CH_2X$, O—$CH_2$—$CH_2X$, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}OR'$ (wherein n1=1, 2, or 3), $CF_3$, $CH_2$—$CH_2X$, $CH_2$—$CH_2$—$CH_2X$, (wherein X=H, F, Cl, Br, or I), CN, (C=O)—R', (C=O)N(F)$_2$, COOR' (wherein R' is H or a lower alkyl group), and $R^3$ or $R^4$ may be absent;

and pharmaceutically acceptable salts thereof.

9. The method of claim 8, wherein the number of hematopoietic stem cells is increased in blood or bone marrow.

10. The method of claim 8, further comprising administering in combination with the 15-PGDH inhibitor at least one hematopoietic cytokine or cell mobilization agent.

11. The method of claim 10, wherein the hematopoietic cytokine or cell mobilization agent comprises at least one of G-CSF or Plerixafor.

12. The method of claim 8, wherein the subject has or is at risk of at least one of neutropenia, thrombocytopenia, anemia, or cytopenia.

13. The method of claim 12, wherein the subject has received a hematopoietic stem cell transplant, bone marrow transplant, chemotherapy, a myelosuppressive therapy, radiation therapy, viral therapy, and/or has a bone marrow disease, cancer, viral infection, aplastic anemia, myelodysplasia, and/or myelofibrosis.

14. The method of claim 8, wherein the 15-PGDH inhibitor has the following formula (VI):

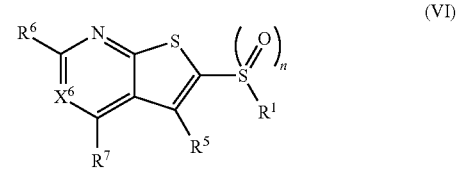

(VI)

wherein n=0-2;
$X^6$ is N or $CR^c$;
$R^1$ is selected from the group consisting of branched or linear alkyl —$(CH_2)n_1CH_3$ ($n_1$=0-7),

wherein $n_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

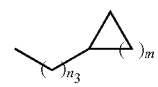

($n_3$=0-5, m=1-5), and

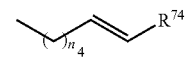

($n_4$=0-5);

$R^5$ is selected from the group consisting of H, Cl, F, $NH_2$, and $N(R^{76})_2$;
$R^6$ and $R^7$ can each independently be one of the following:
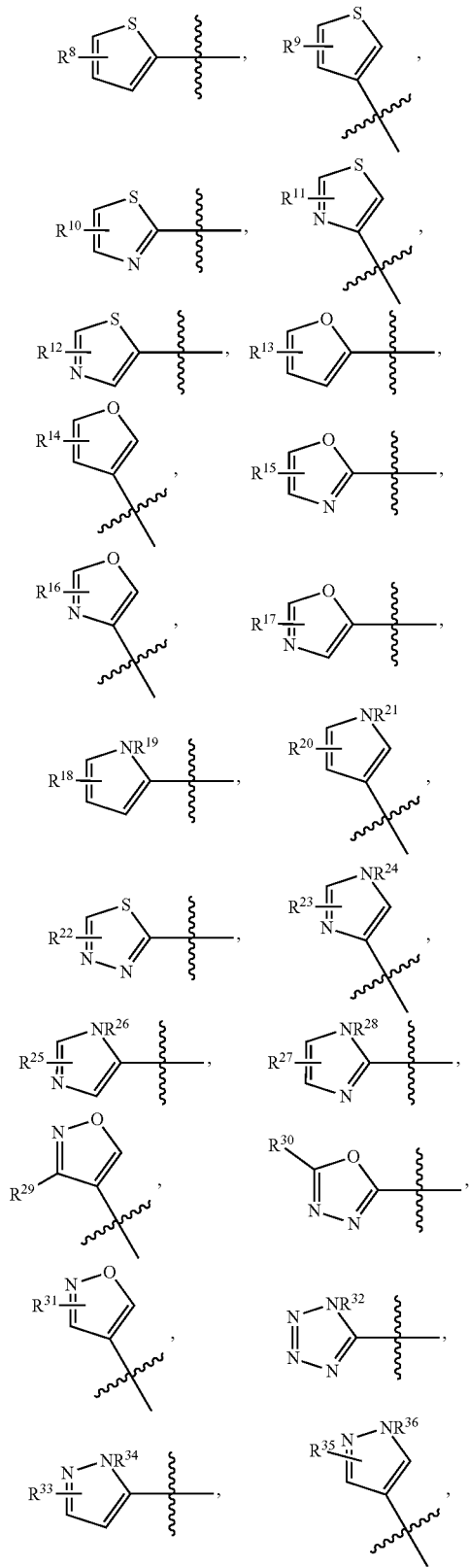
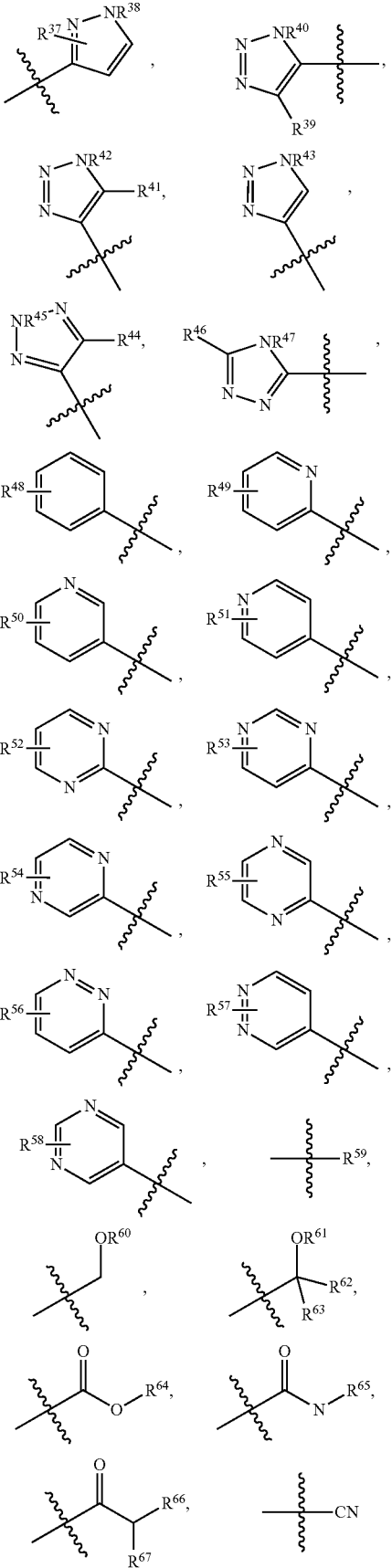

-continued

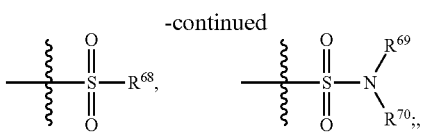

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{76}$, and $R^c$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, and pharmaceutically acceptable salts thereof.

15. The method of claim 8, wherein the 15-PGDH inhibitor has the following formula following formula:

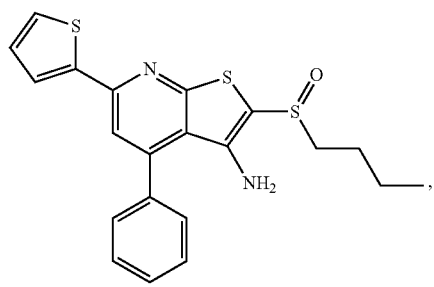

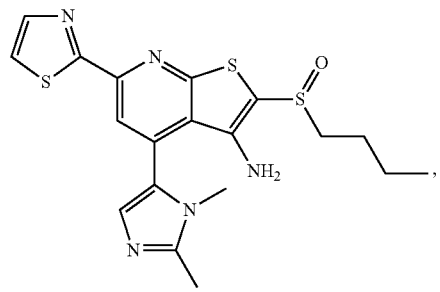

or pharmaceutically acceptable salts thereof.

16. A method of treating at least one of neutropenia, thrombocytopenia, anemia, or cytopenia in a subject in need thereof, the method comprising:

administering to the subject a 15-PGDH inhibitor, wherein the 15-PGDH inhibitor has the following formula (V):

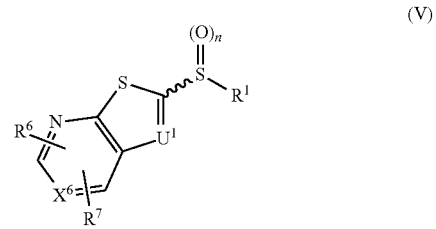

wherein n is 0-2

$X^6$ is independently is N or $CR^c$ $R^1$, $R^6$, $R^7$, and $R^c$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_4$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, and phosphates, phosphate esters, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}OR'$ (wherein n1=1, 2, or 3), $CF_3$, $CH_2$—$CH_2X$, $CH_2$—$CH_2$—$CH_2X$, (wherein X=H, F, Cl, Br, or I), CN, (C=O)—R', (C=O)N(F)$_2$, COOR' (wherein R' is H or a lower alkyl group), and $R^3$ or $R^4$ may be absent; and pharmaceutically acceptable salts thereof.

17. The method of claim 16, further comprising administering in combination with the 15-PGDH inhibitor at least one hematopoietic cytokine or cell mobilization agent.

18. The method of claim 17, wherein the hematopoietic cytokine or cell mobilization agent comprises at least one of G-CSF or Plerixafor.

19. The method of claim 16, wherein the subject has received a hematopoietic stem cell transplant, bone marrow transplant, chemotherapy, a myelosuppressive therapy, radiation therapy, and/or viral therapy, and/or has a bone marrow disease, cancer, viral infection, aplastic anemia, myelodysplasia, and/or myelofibrosis.

20. The method of claim 16, wherein the 15-PGDH inhibitor has the following formula (VI):

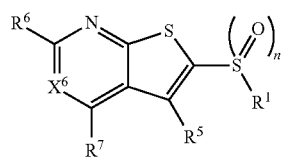

(VI)

wherein n=0-2;
$X^6$ is N or $CR^c$;
$R^1$ is selected from the group consisting of branched or linear alkyl, —$(CH_2)n_1CH_3$ ($n_1$=0-7),

wherein $n_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

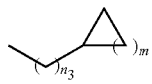

($n_3$=0-5, m=1-5), and

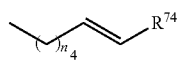

($n_4$=0-5);
$R^5$ is selected from the group consisting of H, Cl, F, $NH_2$, and $N(R^{76})_2$;
$R^6$ and $R^7$ can each independently be one of the following:

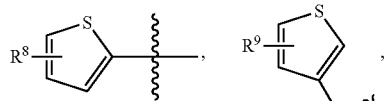
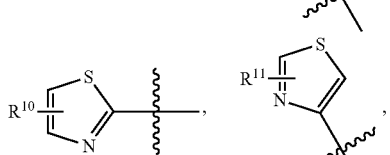

-continued

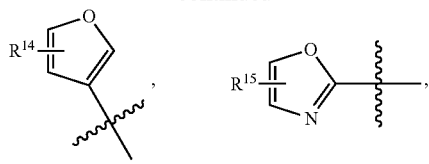
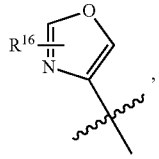 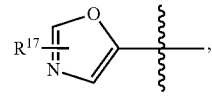
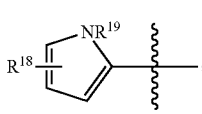 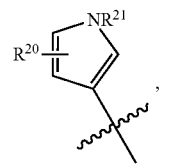
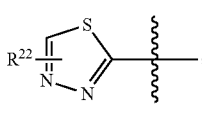 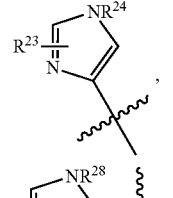
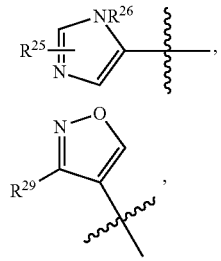 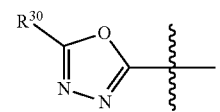
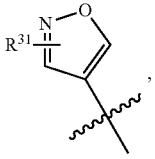 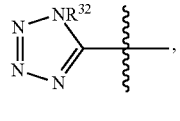
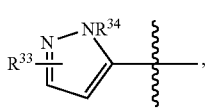 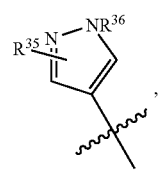
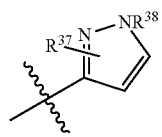 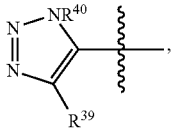
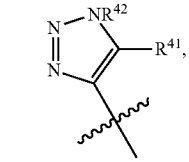 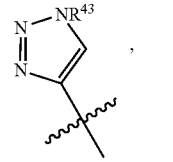
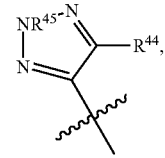 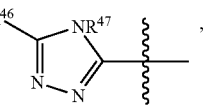

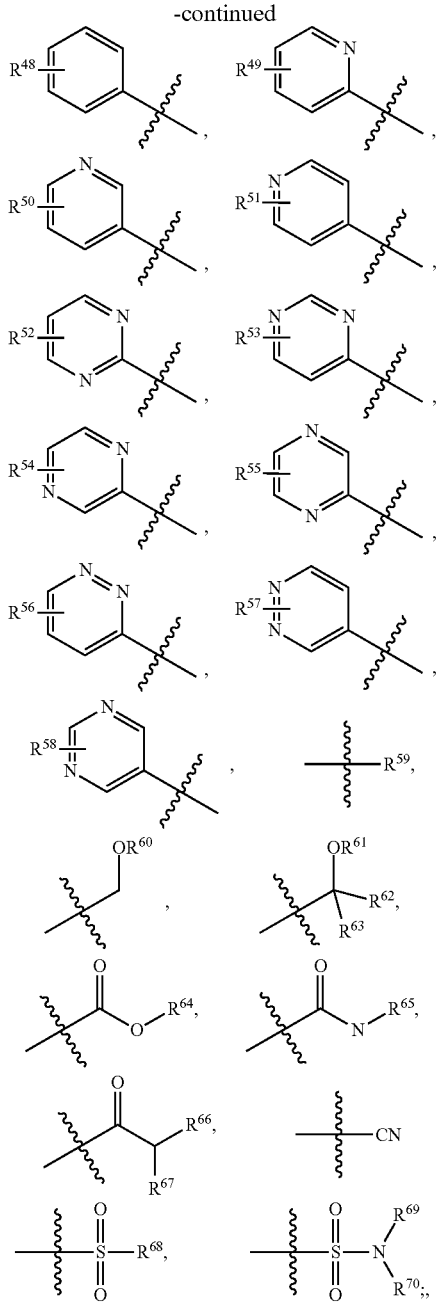

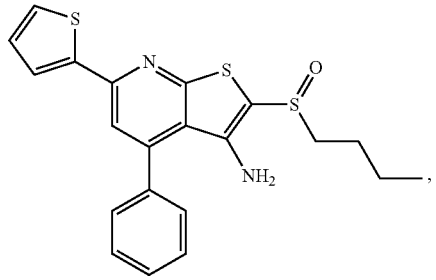

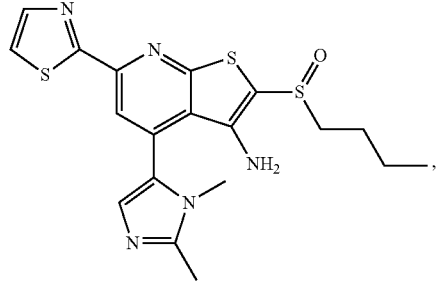

$R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{76}$, and $R^c$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, phosphate esters, and pharmaceutically acceptable salts thereof.

21. The method of claim 16, wherein the 15-PGDH inhibitor has the following formula following formula:

(IX)

(X)

or pharmaceutically acceptable salts thereof.

* * * * *

UNITED STATES PATENT AND TRADEMARK OFFICE
CERTIFICATE OF CORRECTION

PATENT NO. : 9,801,863 B2
APPLICATION NO. : 15/347587
DATED : October 31, 2017
INVENTOR(S) : Sanford Markowitz et al.

Page 1 of 1

It is certified that error appears in the above-identified patent and that said Letters Patent is hereby corrected as shown below:

In the Specification

Please replace the paragraph starting at Line 28, Column 1 with:
--GOVERNMENT FUNDING
This invention was made with government support under Grant Nos. CA127306, CA150964, and CA095471 awarded by The National Institutes of Health. The government has certain rights in the invention.--

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*